(12) United States Patent
Zhang et al.

(10) Patent No.: US 11,479,559 B2
(45) Date of Patent: *Oct. 25, 2022

(54) UREA-SUBSTITUTED AROMATIC RING-LINKED DIOXINOQUINOLINE COMPOUNDS, PREPARATION METHOD AND USES THEREOF

(71) Applicant: BEIJING SCITECH-MQ PHARMACEUTICALS LIMITED, Beijing (CN)

(72) Inventors: Qiang Zhang, Beijing (CN); Shannan Yu, Beijing (CN); Zhongxiang Wang, Beijing (CN); Shouye Feng, Beijing (CN); Yansheng Liu, Beijing (CN); Xingfu Li, Beijing (CN); Hongbo Zhang, Beijing (CN); Leifu Yang, Beijing (CN); Hailong Yang, Beijing (CN); Likai Zhou, Beijing (CN); Nanqiao Zheng, Beijing (CN); Chenming Hu, Beijing (CN); Zhanqiang Xu, Beijing (CN)

(73) Assignee: BEIJING SCITECH-MQ PHARMACEUTICALS LIMITED, Beijing (CN)

( * ) Notice: Subject to any disclaimer, the term of this patent is extended or adjusted under 35 U.S.C. 154(b) by 123 days.

This patent is subject to a terminal disclaimer.

(21) Appl. No.: 16/968,793

(22) PCT Filed: Jan. 25, 2019

(86) PCT No.: PCT/CN2019/073259
§ 371 (c)(1),
(2) Date: Aug. 10, 2020

(87) PCT Pub. No.: WO2019/154132
PCT Pub. Date: Aug. 15, 2019

(65) Prior Publication Data
US 2020/0399284 A1 Dec. 24, 2020

(30) Foreign Application Priority Data

Feb. 11, 2018 (WO) ............... PCT/CN2018/076232
Aug. 27, 2018 (CN) ..................... 201810982631.6

(51) Int. Cl.
| | | |
|---|---|---|
| C07D 491/056 | (2006.01) |
| A61K 31/4741 | (2006.01) |
| A61K 31/496 | (2006.01) |
| A61K 31/5377 | (2006.01) |
| A61K 31/54 | (2006.01) |
| A61K 45/06 | (2006.01) |

(52) U.S. Cl.
CPC ...... *C07D 491/056* (2013.01); *A61K 31/4741* (2013.01); *A61K 31/496* (2013.01); *A61K 31/5377* (2013.01); *A61K 31/54* (2013.01); *A61K 45/06* (2013.01)

(58) Field of Classification Search
CPC .............. A61K 31/4741; A61K 31/496; A61K 31/5377; A61K 31/54; A61K 45/06; A61K 31/519; A61K 31/4545; A61K 31/4738; C07D 491/056
See application file for complete search history.

(56) References Cited

U.S. PATENT DOCUMENTS

| | | |
|---|---|---|
| 6,821,987 B2 | 11/2004 | Kubo et al. |
| 9,730,937 B2 | 8/2017 | Abraham et al. |
| 10,106,508 B2 | 10/2018 | Sheng et al. |
| 2011/0118245 A1 | 5/2011 | Abraham et al. |

(Continued)

FOREIGN PATENT DOCUMENTS

| | | |
|---|---|---|
| CN | 1543459 A | 11/2004 |
| CN | 102026985 A | 4/2011 |
| CN | 102216300 A | 10/2011 |

(Continued)

OTHER PUBLICATIONS

U.S. Appl. No. 16/489,989, filed Aug. 29, 2019, 2020-0061065, Allowed.

(Continued)

*Primary Examiner* — Sahar Javanmard
(74) *Attorney, Agent, or Firm* — McCarter & English, LLP; Xin Zhang; Xiaoyuan Ding

(57) ABSTRACT

The present invention relates to an urea-substituted aromatic ring-linked dioxinoquinoline compound of formula (I), or a pharmaceutically acceptable salt or a hydrate thereof. The invention also provides a preparation method of the compound of formula (I) and a pharmaceutically acceptable salt thereof, as well as uses thereof as a drug, wherein the drug acting as a tyrosine kinase (i.e. VEGFR-2, C-RAF, B-RAF, and RET) inhibitor is used for treating disorders related to tyrosine kinase.

Formula (I)

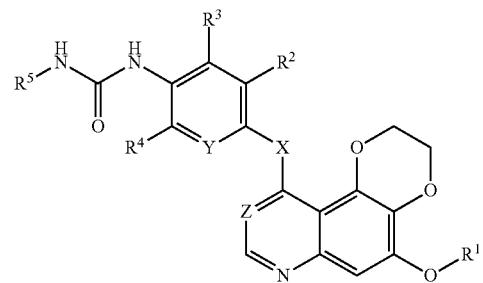

20 Claims, No Drawings

(56) References Cited

U.S. PATENT DOCUMENTS

2020/0061065 A1   2/2020   Zhang et al.

FOREIGN PATENT DOCUMENTS

| CN | 102311395 | A  | 1/2012 |
|----|-----------|----|--------|
| CN | 102532042 | A  | 7/2012 |
| CN | 104530063 | A  | 4/2015 |
| CN | 105837586 | A  | 8/2016 |
| CN | 105884699 | A  | 8/2016 |
| EP | 1566379   | A1 | 8/2005 |
| EP | 1949902   | A1 | 7/2008 |
| WO | 2012/019015 | A2 | 2/2012 |
| WO | 2013/036232 | A2 | 3/2013 |
| WO | 2014/127214 | A1 | 8/2014 |
| WO | 2018/157730 | A1 | 9/2018 |

OTHER PUBLICATIONS

Ghosh et al., Design of Proteasome Inhibitors. Structure-based Design of Drugs and Other Bioactive Molecules, Tools and Strategies. Wiley-VCH. pp. 113-129, (2014).

Qin et al., Discovery of new [1,4]dioxino[2,3-f]quinazoline-based inhibitors of EGFR including the T790M/L858R mutant. Bioorg Med Chem. Jul. 1, 2016;24(13):2871-2881.

Wermuth, Molecular Variations Based on Isosteric Replacements. The Practice of Medicinal Chemistry. Chapter 13, pp. 189-214, (2003).

Black, Flow Chart Determination of Isomeric Relationships. Journal of Chemical Education. Feb. 1990;67(2):141-142.

Fan et al., Discovery of Dioxino[2,3-f]quinazoline derivative VEGFR-2 inhibitors exerting significant antipro-liferative activity in HUVECs and mice. Eur J Med Chem. Aug. 1, 2019;175:349-356.

Karoulia et al., New perspectives for targeting RAF kinase in human cancer. Nat Rev Cancer. Nov. 2017;17(11):676-691.

Zawilska et al., Prodrugs: a challenge for the drug development. Pharmacol Rep. 2013;65(1):1-14.

Zhang et al., Design and discovery of 4-anilinoquinazoline-urea derivatives as dual TK inhibitors of EGFR and VEGFR-2. Eur J Med Chem. 23 pages, Sep. 13, 2016.

International Search Report and Written Opinion for Application No. PCT/CN2019/073259, dated Apr. 29, 2019, 10 pages.

International Search Report and Written Opinion for Application No. PCT/CN2018/076232, dated Apr. 23, 2018, 7 pages.

UREA-SUBSTITUTED AROMATIC RING-LINKED DIOXINOQUINOLINE COMPOUNDS, PREPARATION METHOD AND USES THEREOF

CROSS REFERENCE TO RELATED APPLICATIONS

The present application is a national application of PCT/CN2019/073259 filed on Jan. 25, 2019, which claims the priority of the PCT Application No. PCT/CN2018/076232 filed on Feb. 11, 2018, and the Chinese Patent Application No. 201810982631.6 filed on Aug. 27, 2018. The PCT Application No. PCT/CN2018/076232 and the Chinese Patent Application No. 201810982631.6 are incorporated herein by reference as part of the disclosure of the present application.

TECHNICAL FIELD

The present disclosure relates to a urea-substituted aromatic ring-linked dioxinoquinoline compound, preparation method thereof and use thereof, which belongs to the technical field of medicinal chemistry.

BACKGROUND

VEGF (vascular endothelial growth factor) must present for neovascularization and angiogenesis. During embryogenesis, the formation of blood vessels is divided into two stages, neovascularization and angiogenesis. Neovascularization is the differentiation of primitive progenitor cells into endothelial cells; and angiogenesis is the outgrowth of the nascent capillaries from the existing blood vessels in the form of budding. For normal adult mammals, there is only one type of blood vessels formation, i.e., angiogenesis, decomposition of local basement membrane around endothelial cells, and invasion of endothelial cells into the matrix. Such invasion is accompanied by the proliferation of endothelial cells, forming a migration column of endothelial cells that changes shape and forms a ring with each other. Thus, the new blood vessel cavity is formed.

VEGF is also essential for the angiogenesis of tumor tissues, and vascular endothelial growth factor A (VEGFA) and vascular endothelial growth factor receptor 2 (VEGFR-2) signaling pathways play the most important role, affecting the proliferation, survival, budding, migration of endothelial cells in tumor tissues, as well as affecting the permeability of tumor blood vessels. Endothelial cells without VEGF protein stimulation can also rely on autocrined VEGF proteins to maintain their integrity and survival. Vascular endothelial growth factor C (VEGFR-C)/vascular endothelial growth factor D (VEGF-D) mediates lymphangiogenesis in tumor tissues and promotes the metastasis of tumor tissues. Therefore, the development of drugs targeting angiogenesis have become a hot spot.

Bevacizumab is a 93% humanized murine VEGF monoclonal antibody, capable of binding to all subtypes of human VEGF A, blocks the VEGF/VEGFR signaling pathway, and inhibits tumor angiogenesis. In 2004, bevacizumab (trade name Avastin) was approved by FDA for selling in the United States, and became the first anti-tumor angiogenesis drug as the first-line drugs for the treatment of metastatic colorectal cancer used in combination with chemotherapeutic drugs. Bevacizumab could improve the abnormal tumor blood vessels, making them normalized and assisting chemotherapy drugs to reach tumor tissues. Due to the apoptosis mechanism induced by radiotherapy and chemotherapy, the hypoxic partial pressure in tumor tissues induces the expression of VEGF, and thus the combination of bevacizumab and chemoradiotherapy drugs effectively prevents such secondary reactions.

To date, there are nine drugs targeting VEGFR-2/KDR: sorafenib, sunitinib, pazopanib, axitinib, vandetanib, regorafenib, lenvatinib, nintedanib and Cediranib (AZD2171), which have been approved by the FDA for the treatment of cancer.

Lenvatinib, trade name Lenvima, is a drug for thyroid cancer developed by Eisai Corporation, Japan, which has specific inhibitory effects on VEGFR-1, VEGFR-2 and VEGFR-3, and also inhibits PDGFRβ and FGFR-1. It is a class of TKI that selectively targets multiple receptors. With a similar mechanism to sorafenib, it inhibits neovascularization by inhibiting VEGFR-1, 2, 3 and PDGFR on one hand, and directly inhibits tumor cell proliferation by inhibiting FGFR-1 on the other hand. In 2015, the FDA approved Lenvatinib for the treatment of thyroid cancer.

B-RAF is a kind of tyrosine kinase receptor, and its abnormal activation plays an important role in the occurrence and development of various malignant tumors. In most cases, abnormal activation of B-RAF is caused by gene mutations. B-RAF belongs to the proto-oncogene. Studies have shown that more than 30 types of B-RAF gene mutations are associated with cancer, especially the V600E gene mutation. Mutations in the B-RAF gene usually cause two diseases. First, mutations can be inherited and cause birth defects. Second, as oncogenes, inherited mutations can lead to cancer in future life. B-RAF gene mutations have been found in many cancer tissues, including melanoma, colon cancer, thyroid cancer, non-small cell lung cancer, and glioma.

Sorafenib, trade name Nexavar, is a drug developed by Onyx Pharmaceuticals of the United States and Bayer AG of Germany, targeting the RAF/MEK/ERK signaling pathway, which mainly inhibits C-RAF and B-RAF, and also inhibits the activities of VEGFR-2, VEGFR-3, PDGFR-β, Flt-3, and c-Kit receptors. It can effectively inhibit tumor cell proliferation and angiogenesis in preclinical experiments. In a phase III clinical trial of metastatic renal cell carcinoma, sorafenib significantly increased the overall survival of the patient. In July of 2005, sorafenib was approved by the FDA as a drug for the treatment of advanced renal cell carcinoma.

There are many advantages for multi-targets inhibitors similar to Lenvatinib and Sorafenib, and research on such type of inhibitors is also a hot spot. However, currently, there are still very few similar drugs on the market, with limited availability, and the drugs on the market are subject to drug resistance and side effects. Therefore, such multi-targets small molecule inhibitor will have better therapeutic effects and application prospects compared to the existing single-target inhibitors on the market.

RET is also a kind of transmembrane receptor tyrosine kinases, which is essential for the normal development of tissues such as brain, nervous system, thyroid and lung. Activation mutation and oncogenic fusion of receptor tyrosine kinases have been discovered in a variety of tumor types, including thyroid cancer, lung cancer, breast cancer and colon cancer. At present, there is no marketed drug with RET as a specific target. Therefore, small molecule inhibitors for RET have extremely high application value.

SUMMARY

In view of the deficiencies in the prior art, the present disclosure provides compounds represented by formula (I), or pharmaceutically acceptable salts, isomers, hydrates, solvates, or prodrugs thereof, Formula (I)

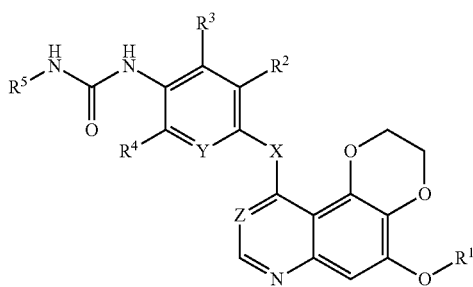

in the formula (I),
X is O or NH;
Y is CH;
Z is CH;
$R^1$ is H, $C_1$-$C_9$ alkyl, $C_3$-$C_7$ cycloalkyl, 4- to 7-membered heterocyclyl, $C_1$-$C_6$ alkyl substituted with $C_3$-$C_7$ cycloalkyl, $C_1$-$C_6$ alkyl substituted with 4- to 7-membered heterocyclyl, or $C_1$-$C_9$ alkyl substituted with one or more of the following: hydroxyl, $C_1$-$C_6$ alkoxy, $C_1$-$C_6$ alkylthio, amino substituted with mono- or di-$C_1$-$C_6$ alkyl, and unsubstituted amino, the above 4- to 7-membered heterocyclyl is a 4- to 7-membered heterocyclyl containing 1 to 2 atoms selected from the group consisting of N, O, and S, which is unsubstituted, or is substituted with $C_1$-$C_6$ alkyl or $C_1$-$C_3$ acyl, or is oxidized by 1 to 2 oxygen atoms;
$R^2$ is H or halogen;
$R^3$ is H or halogen;
$R^4$ is H or halogen;
$R^5$ is H, $C_1$-$C_9$ alkyl, $C_3$-$C_8$ cycloalkyl, $C_1$-$C_6$ alkyl substituted with $C_3$-$C_8$ cycloalkyl, unsubstituted aryl or heteroaryl, or an aryl or heteroaryl group substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, unsubstituted amino, halogen, trifluoromethyl, aryloxy and methylsulfonyl; and the heteroaryl group is a monocyclic or bicyclic group containing 5 to 10 ring atoms, which contains 1 to 3 atoms selected from the group consisting of N, O, and S in the ring.

In an alternative embodiment, $R^1$ is H, $C_1$-$C_6$ alkyl, $C_3$-$C_6$ cycloalkyl, 5- to 6-membered heterocyclyl, $C_1$-$C_3$ alkyl substituted with $C_3$-$C_6$ cycloalkyl, $C_1$-$C_3$ alkyl substituted with 5- to 6-membered heterocyclyl, or $C_1$-$C_6$ alkyl substituted with one or more of the following: hydroxyl, $C_1$-$C_3$ alkoxy, $C_1$-$C_3$ alkylthio, amino substituted with mono- or di-$C_1$-$C_3$ alkyl, and unsubstituted amino, the above 5- to 6-membered heterocyclyl is a 5- to 6-membered heterocyclyl containing 1 to 2 atoms selected from the group consisting of N, O, and S, which is unsubstituted, or is substituted with $C_1$-$C_3$ alkyl or $C_1$-$C_3$ acyl, or is oxidized by 1 to 2 oxygen atoms.

In an alternative embodiment, $R^1$ is selected from the group consisting of H, methyl, ethyl, propyl, isopropyl, methoxyethyl, methoxypropyl, methoxybutyl, methoxypentyl, methoxyhexyl, tetrahydrofuran-3-yl, tetrahydro-2H-pyran-4-yl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholinyl)-4-ethyl, (1,1-dioxothiomorpholinyl)-4-propyl, methylthioethyl, methylthiopropyl, dimethylaminoethyl, dimethylaminopropyl, dimethylaminobutyl, diethylaminoethyl, diethylaminopropyl, hydroxyethyl, hydroxypropyl, hydroxybutyl, hydroxypentyl, hydroxyhexyl, aminoethyl, aminopropyl, aminobutyl, 2-methyl-2-hydroxypropyl, 3-methyl-3-hydroxybutyl, (3S)-3-aminobutyl, (3R)-3-aminobutyl, (3S)-3-hydroxybutyl, or (3R)-3-hydroxybutyl.

In an alternative embodiment, $R^1$ is selected from the group consisting of butyl, isobutyl, pentyl, isopentyl, hexyl, cyclopropylmethyl, cyclopropylethyl, cyclopropylpropyl, cyclobutylmethyl, cyclobutylethyl, cyclobutylpropyl, 4,4-dimethylpiperidin-1-ylethyl, 4,4-dimethylpiperidin-1-ylpropyl, dimethylaminopentyl, dimethylaminohexyl, and oxetan-3-yl.

In an alternative embodiment, the halogen described in $R^2$, $R^3$ and $R^4$ is F, Cl or Br.

In an alternative embodiment, $R^5$ is H, $C_1$-$C_6$ alkyl, $C_3$-$C_6$ cycloalkyl, $C_1$-$C_3$ alkyl substituted with $C_3$-$C_6$ cycloalkyl, unsubstituted aryl or heteroaryl, or an aryl or heteroaryl group substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, unsubstituted amino, halogen, trifluoromethyl, aryloxy and methylsulfonyl; and a heteroaryl group is a monocyclic or bicyclic group containing 5 to 10 ring atoms, which contains 1 to 2 atoms selected from the group consisting of N, O, and S in the ring.

In an alternative embodiment, $R^5$ is H, $C_1$-$C_6$ alkyl, $C_3$-$C_6$ cycloalkyl, $C_1$-$C_3$ alkyl substituted with $C_3$-$C_6$ cycloalkyl, unsubstituted phenyl, naphthyl or heteroaryl, or a phenyl, naphthyl or heteroaryl group substituted with one or more of the following: methyl, ethyl, propyl, isopropyl, methoxy, ethoxy, propoxy, isopropoxy, methylthio, ethylthio, propylthio, isopropylthio, amino, methylamino, ethylamino, dimethylamino, diethylamino, fluorine, chlorine, bromine, trifluoromethyl, phenoxy or methylsulfonyl;

the heteroaryl group is selected from the group consisting of pyridinyl, pyrimidinyl, quinolinyl, quinazolinyl, oxazolyl, isoxazolyl, thiazolyl, thiadiazolyl, pyrazolyl, imidazolyl, and pyrrolyl.

In an alternative embodiment, $R^5$ is selected from the group consisting of H, methyl, ethyl, propyl, isopropyl, isopentyl, cyclopropyl, cyclobutyl, cyclopentyl, cyclohexyl, phenyl, 2-methoxyphenyl, 3-methoxyphenyl, 4-methoxyphenyl, 2-fluorophenyl, 3-fluorophenyl, 4-fluorophenyl, 4-phenoxyphenyl, 3-(methylsulfonyl)phenyl, 4-(methylsulfonyl)phenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-(trifluoromethyl)-4fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-(trifluoromethyl)-4-chlorophenyl, 2-chloro-4-fluorophenyl, 2-chloro-5-fluorophenyl, 3-chloro-4-fluorophenyl, pyridin-2-yl, pyridin-3-yl, pyridin-4-yl, 2-methoxypyridin-4-yl, 3-methyl-isoxazol-5-yl, and naphthalen-1-yl.

In an alternative embodiment, $R^5$ is selected from the group consisting of butyl, isobutyl, 2-methylphenyl, 3-methylphenyl, 4-methylphenyl, 2-methyl-5-(trifluoromethyl)phenyl, 2-methyl-4-(trifluoromethyl)phenyl, 3-methyl-4-(trifluoromethyl)phenyl, 3-methyl-5-(trifluoromethyl)phenyl, 2-chloro-4-methylphenyl, 2-chloro-5-methylphenyl, and 3-chloro-4-methylphenyl.

The present disclosure relates to a compound represented by formula (I), or a pharmaceutically acceptable salt, an isomer, a hydrate, a solvate, or a prodrug thereof, Formula (I)

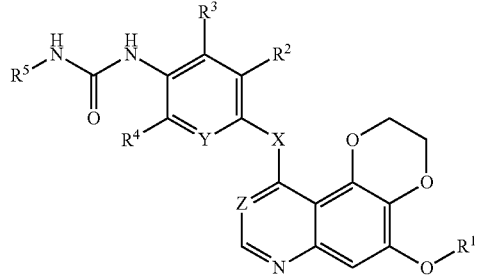

in the formula (I),
X is O or NH;
Y is CH;
Z is CH;
$R^1$ is $C_1$-$C_6$ alkyl substituted with 1 to 3 substituents selected from the group consisting of $C_1$-$C_3$ acyl, halogen, trifluoromethyl, cyano, —$CONH_2$, —$NR^aR^b$ and 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of halogen, $C_1$-$C_3$ alkyl, hydroxyl, —$NH_2$, and $C_1$-$C_3$ acyl, $R^a$ and $R^b$ are each independently H, $C_1$-$C_6$ alkyl, $C_3$-$C_6$ cycloalkyl, $C_1$-$C_6$ alkyl substituted with $C_1$-$C_3$ alkoxy, $C_1$-$C_6$ alkyl substituted with $C_1$-$C_3$ alkylthio, $C_1$-$C_6$ alkyl substituted with substituted amino or unsubstituted amino, wherein the substituted amino is substituted with mono- or di-$C_1$-$C_3$ alkyl;

$R^2$, $R^3$, and $R^4$ are each independently H or halogen;
$R^5$ is H, $C_1$-$C_9$ alkyl, $C_3$-$C_8$ cycloalkyl, $C_1$-$C_6$ alkyl substituted with $C_3$-$C_8$ cycloalkyl, unsubstituted aryl or heteroaryl, or an aryl or heteroaryl group substituted with 1 to 3 substituents —B, wherein the substituents —B are each independently hydroxyl, cyano, $C_1$-$C_3$ alkyl, $C_1$-$C_3$ alkoxy, $C_1$-$C_3$ alkylthio, amino substituted with mono- or di-$C_1$-$C_3$ alkyl, unsubstituted amino, halogen, trifluoromethyl, aryloxy or methylsulfonyl;

the heteroaryl group is a monocyclic or bicyclic group containing 5 to 10 ring atoms, which contains 1 to 3 atoms selected from the group consisting of N, O, and S in the ring.

Alternatively, $R^1$ is $C_1$-$C_6$ alkyl substituted with 1 to 3 substituents selected from the group consisting of —F, trifluoromethyl, cyano, —$CONH_2$, —$NR^aR^b$ or 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of —F, $C_1$-$C_3$ alkyl, hydroxyl, —$NH_2$, and $C_1$-$C_3$ acyl, and $R^a$ and $R^b$ are each independently H, $C_1$-$C_3$ alkyl, $C_3$-$C_6$ cycloalkyl, $C_1$-$C_3$ alkyl substituted with $C_1$-$C_3$ alkoxy, $C_1$-$C_3$ alkyl substituted with $C_1$-$C_3$ alkylthio, or $C_1$-$C_3$ alkyl substituted with substituted amino or unsubstituted amino, wherein the substituted amino is substituted with mono- or di-$C_1$-$C_3$ alkyl.

$R^5$ is H, $C_1$-$C_6$ alkyl, $C_3$-$C_6$ cycloalkyl, $C_1$-$C_3$ alkyl substituted with $C_3$-$C_6$ cycloalkyl, unsubstituted phenyl, naphthyl or heteroaryl, or a phenyl, naphthyl or heteroaryl group substituted with 1 to 3 substituents —B, wherein the substituents —B are each independently methyl, ethyl, propyl, isopropyl, methoxy, ethoxy, propoxy, isopropoxy, methylthio, ethylthio, propylthio, isopropylthio, amino, methylamino, ethylamino, dimethylamino, diethylamino, fluorine, chlorine, bromine, trifluoromethyl, phenoxy or methylsulfonyl; and the heteroaryl group is selected from the group consisting of pyridinyl, pyrimidinyl, quinolinyl, quinazolinyl, oxazolyl, isoxazolyl, thiazolyl, thiadiazolyl, pyrazolyl, imidazolyl, and pyrrolyl.

Yet alternatively, $R^1$ is selected from the group consisting of cyanomethyl, cyanoethyl, cyanopropyl, —$CH_2CONH_2$, —$CH_2CF_3$,

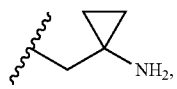

4-methyl-4-hydroxypiperidin-1-ylpropyl, 4-methyl-4-hydroxypiperidin-1-ylethyl, 4-methyl-4-aminopiperidin-1-ylpropyl, 4-methyl-4-aminopiperidin-1-ylethyl, hydroxyethylaminoethyl, hydroxypropylaminoethyl, hydroxyethylaminopropyl, methoxyethylaminoethyl, methoxypropylaminoethyl, methoxyethylaminopropyl, N-methyl-N-hydroxyethylaminoethyl, N-methyl-N-hydroxypropylaminoethyl, N-methyl-N-hydroxyethylaminopropyl, N-methyl-N-methoxyethylaminoethyl, N-methyl-N-methoxypropylaminoethyl, N-methyl-N-methoxyethylaminopropyl, N-methyl-N-cyclobutylaminopropyl, N-methyl-N-cyclopropylaminopropyl, N-methyl-N-cyclopentylaminopropyl, N-methyl-N-cyclohexylaminopropyl, N-methyl-N-cyclobutylaminoethyl, N-methyl-N-cyclopropylaminoethyl, N-methyl-N-cyclopentylaminoethyl, and N-methyl-N-cyclohexylaminoethyl.

Yet alternatively, $R^5$ is selected from the group consisting of H, methyl, ethyl, propyl, isopropyl, butyl, isobutyl, isopentyl, cyclopropyl, cyclobutyl, cyclopentyl, cyclohexyl, phenyl, 2-methoxyphenyl, 3-methoxyphenyl, 4-methoxyphenyl, 2-fluorophenyl, 3-fluorophenyl, 4-fluorophenyl, 4-phenoxyphenyl, 3-(methylsulfonyl)phenyl, 4-(methylsulfonyl)phenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-(trifluoromethyl)-4-fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-(trifluoromethyl)-4-chlorophenyl, 2-chloro-4-fluorophenyl, 2-chloro-5-fluorophenyl, 3-chloro-4-fluorophenyl, pyridin-2-yl, pyridin-3-yl, pyridin-4-yl, 2-methoxypyridin-4-yl, 3-methyl-isox azol-5-yl, naphthalen-1-yl, 2-methylphenyl, 3-methylphenyl, 4-methylphenyl, 2-methyl-5-(trifluoromethyl)phenyl, 2-methyl-4-(trifluoromethyl)phenyl, 3-methyl-4-(trifluoromethyl)phenyl, 3-methyl-5-(trifluoromethyl)phenyl, 2-chloro-4-methylphenyl, 2-chloro-5-methylphenyl, and 3-chloro-4-methylphenyl.

The present disclosure also provides a salt of the compounds represented by Formula (I), wherein the salt is an acidic/anionic salt or a basic/cationic salt; a pharmaceutically acceptable acidic/anionic salt is usually in the form in which the basic nitrogen is protonated by an inorganic or organic acid; representative organic or inorganic acids include hydrochloric acid, hydrobromic acid, hydroiodic acid, perchloric acid, sulfuric acid, nitric acid, phosphoric acid, formic acid, acetic acid, propionic acid, glycolic acid, lactic acid, succinic acid, maleic acid, tartaric acid, malic acid, citric acid, fumaric acid, gluconic acid, benzoic acid, mandelic acid, methanesulfonic acid, isethionic acid, benzenesulfonic acid, oxalic acid, palmitic acid, 2-naphthalenesulfonic acid, p-toluenesulfonic acid, cyclohexylsulfamic acid, salicylic acid, hexonic acid, trifluoroacetic acid. Pharmaceutically acceptable basic/cationic salts include but are not limited to salts of aluminum, calcium, chloroprocaine, choline, diethanolamine, ethylenediamine, lithium, magnesium, potassium, sodium and zinc.

In one embodiment disclosed herein, provided is a method of preparing a compound of Formula (I), or a pharmaceutically acceptable salt, an isomer, a hydrate, a solvate, or a prodrug thereof, comprising the preparation of the compound of Formula (I) from the reaction of the compound of Formula (II) with $H_2N-R^5$, wherein X, Y, Z, $R^1$, $R^2$, $R^3$, $R^4$, and $R^5$ are as defined above,

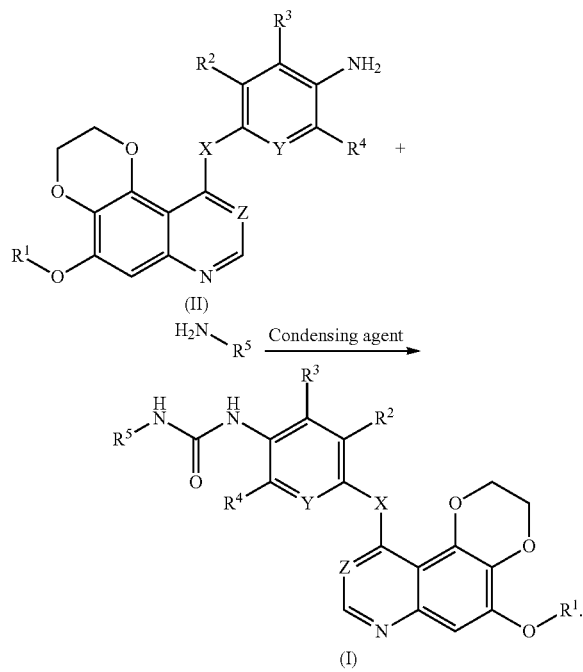

DETAILED DESCRIPTION OF THE EMBODIMENTS

Unless otherwise stated, the following terms used in this application (including the specification and claims) have the definitions given below. In this application, the use of "or" or "and" means "and/or" unless stated otherwise. In addition, the use of the term "comprising" and other forms such as "including", "containing" and "having" is not limiting. The chapter headings used herein are for organizational purposes only and should not be interpreted as limitations on the topics described.

The term "substituted" as used herein, includes multiple substituents (e.g., phenyl, aryl, heteroalkyl, heteroaryl), preferably 1 to 5 substituents, more preferably 1 to 3 substituents, most preferably 1 or 2 substituents, independently selected from the list of substituents.

Unless otherwise specified, alkyl includes saturated linear and branched hydrocarbon group, $C_1$-$C_9$ represents the number of carbon atoms of an alkyl is 1-9. Similarly, for example, $C_1$-$C_3$ represents the number of carbon atoms of an alkyl is 1-3, e.g., $C_1$-$C_6$ alkyl includes methyl, ethyl, propyl, isopropyl, n-butyl, isobutyl, sec-butyl, tert-butyl, n-pentyl, 3-(2-methyl)butyl, 2-pentyl, 2-methylbutyl, neopentyl, n-hexyl, 2-hexyl, and 2-methylpentyl, etc. An alkoxy group is an alkyl-O— group formed from a linear or branched alkyl group described previously and —O—. Similarly, alkenyl and alkynyl groups include linear or branched alkenyl or alkynyl groups.

Cycloalkyl refers to a cyclic group formed by carbon atoms. For example, $C_3$-$C_7$ cycloalkyl may include cyclopropyl, cyclobutyl, cyclopentyl, cyclohexyl, and cycloheptyl. Similarly, cyclic alkenyl group is also included herein.

The term "aryl" as used herein, unless otherwise specified, refers to an unsubstituted or substituted aromatic group, such as phenyl, naphthyl, anthracenyl.

"Oxidized by one or two oxygen atoms" refers to a sulfur atom oxidized by one oxygen atom to form a double bond between the sulfur and oxygen, or oxidized by two oxygen atoms to form double bonds between the sulfur and two oxygen atoms.

The term "heterocyclyl" as used herein, unless otherwise specified, represents an unsubstituted or substituted stable 3 to 8 membered monocyclic saturated ring system consisting of carbon atoms and 1 to 3 heteroatoms selected from N, O, and S, wherein the N, S heteroatoms can be optionally oxidized, and the N heteroatoms can also be optionally quaternized. Examples of such heterocyclyl rings include, but are not limited to, azetidinyl, pyrrolidinyl, tetrahydrofuranyl, tetrahydrothiazolyl, tetrahydropyranyl, morpholinyl, thiomorpholinyl, piperidinyl, piperazinyl, oxopiperazinyl, oxopiperidinyl, dioxolanyl, dioxanyl, tetrahydroimidazolyl, tetrahydrooxazolyl, thiamorpholinyl sulfoxide, thiomorpholine sulfone and oxadiazolyl.

The term "heteroaryl" as used herein, unless otherwise specified, represents an unsubstituted or substituted stable 5 or 6 membered monocyclic aromatic ring system, and may also represent unsubstituted or substituted 9 or 10-membered benzo-fused heteroaromatic ring system or a bicyclic heteroaromatic ring system consisting of carbon atoms and one to three heteroatoms selected from N, O, S, wherein the N, S heteroatoms may optionally be oxidized, and N heteroatoms may optionally be quaternized. Heteroaryl can be attached at any heteroatom or carbon atom to form a stable structure. Heteroaryl includes but is not limited to thienyl, furyl, imidazolyl, pyrrolyl, thiazolyl, oxazolyl, isoxazolyl, pyranyl, pyridinyl, piperazinyl, pyrimidinyl, pyrazinyl, pyridazinyl, pyrazolyl, thiadiazolyl, triazolyl, indolyl, azaindolyl, indazolyl, azaindazolyl, benzimidazolyl, benzofuryl, benzothienyl, benzoisoxazolyl, benzoxazolyl, benzopyrazolyl, benzothiazolyl, benzothiadiazolyl, benzotriazolyl, adeninyl, quinolinyl, or isoquinolinyl.

The term "carbonyl" refers to a —C(O)— group.

Whenever the terms "alkyl" or "aryl" or either of their prefix roots appear in the name of a substituent (eg, aralkyl, dialkylamino), it shall be interpreted to contain those limitations given for the above "alkyl" and "aryl". Designated numbers of carbon atoms (e.g., $C_1$-$C_6$) shall independently represent the number of carbon atoms in an alkyl moiety or an alkyl moiety in a larger substituent (wherein the alkyl group is the prefix root).

It is apparent that the compounds of Formula I, the isomers, crystalline forms or prodrugs, and pharmaceutically acceptable salts thereof, may exist in both solvated and unsolvated forms. For example, the solvated form can be a hydrate form. The disclosure includes both solvated and unsolvated forms.

The compounds of the present disclosure may have asymmetric carbon atoms. Such diastereomeric mixtures can be separated into their individual diastereomers on the basis of their different physicochemical properties by methods known to those skilled in the art, for example, by chromatography or fractional crystallization. Enantiomers can be separated by converting the enantiomeric mixtures into a diastereomeric mixture by reaction with an appropriate optically active compound, separating the diastereomers and converting (e.g., hydrolyzing) the individual diastereomers to the corresponding pure enantiomers. All such isomers, including diastereomer mixtures and pure enantiomers are considered as part of the disclosure.

The compound of the present disclosure as an active ingredient, and the method of preparing the same, are both included in the present disclosure. Moreover, the crystalline form of some of the compounds may exist as polymorphs, and such forms may also be included in the present disclosure. Additionally, some of the compounds may form solvates with water (i.e., hydrates) or common organic solvents, and such solvates are also included within the scope of the disclosure.

The compounds of the disclosure may be used in the free form for treatment or, when appropriate, in the form of a pharmaceutically acceptable salt or other derivative for treatment. As used herein, the term "pharmaceutically acceptable salt" refers to organic and inorganic salts of the compounds of the present disclosure which are suitable for use in human and lower animals without undue toxicity, irritation, allergic response, etc., and have reasonable benefit/risk ratio. Pharmaceutically acceptable salts of amines, carboxylic acids, phosphonates, and other types of compounds are well known in the art. The salt can be formed by reacting a compound of the disclosure with a suitable free base or acid, including, but not limited to, salts with inorganic acids such as hydrochloric acid, hydrobromic acid, phosphoric acid, sulfuric acid, perchloric acid or with organic acids such as acetic acid, oxalic acid, maleic acid, tartaric acid, citric acid, succinic acid, malonic acid. Or the salts may be obtained by methods well known in the art, such as ion exchange. Other pharmaceutically acceptable salts include adipate, alginate, ascorbate, aspartate, besylate, benzoate, bisulfate, borate, butyrate, camphorate, camphorsulfonate, citrate, digluconate, lauryl sulfate, ethanesulfonate, formate, fumarate, glucoheptonate, glycerol phosphate, glyconate, hemisulfate, hexanoate, hydroiodide, 2-hydroxyethanesulfonate, lactobionate, lactate, laurate, lauryl sulfate, malate, maleate, mesylate, 2-naphthalenesulfonate, nicotinate, nitrate, oleate, palmitate, pamoate, pectate, persulphate, per-3-phenylpropionate, phosphate, picrate, propionate, stearate, sulfate, thiocyanate, p-toluenesulfonate, undecanoate, and the like. Representative alkali or alkaline earth metal salts include salts of sodium, lithium, potassium, calcium, magnesium, and the like. Other pharmaceutically acceptable salts include suitable non-toxic salts of ammonium, quaternary ammonium, and amine cations formed from halides, hydroxides, carboxylates, sulfates, phosphates, nitrates, lower alkyl sulfonates and aryl sulfonates.

Further, the term "prodrug" as used herein means that a compound can be converted into a compound of Formula (I) of the present disclosure in vivo. Such transformation is affected by hydrolysis of the prodrug in the blood or enzymatic conversion to the parent compound in the blood or tissue.

Pharmaceutical compositions of this disclosure comprise a compound of the formula (I) described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyper proliferation compound; and any pharmaceutically acceptable carrier, adjuvant or vehicle.

The compounds of the present disclosure may be used alone or in combination with one or more of other compounds of the present disclosure or with one or more of other agents. When administered in combination, the therapeutic agents can be formulated for simultaneous or sequential administration at different times, or the therapeutic agents can be administered as a single composition. By "combination therapy", it refers to the use of a compound of the disclosure in combination with another agent in the form of co-administration of each agent or sequential administration of each agent, in either case, for the purpose of achieving the optimal results. Co-administration includes dosage form for simultaneous delivery, as well as separate dosage forms for each compound. Thus, administration of the compounds of the disclosure can be combined with other therapies known in the art, for example, radiation therapy or cytostatic agents, cytotoxic agents, other anticancer agents, and the like as used in the treatment of cancer, in order to improve the symptoms of cancer. The administration sequence is not limited in the present disclosure. The compounds of the present disclosure may be administered before, simultaneously, or after other anticancer or cytotoxic agents.

To prepare the pharmaceutical ingredient of the present disclosure, one or more compounds of Formula (I) or salts thereof as an active ingredient can be intimately mixed with a pharmaceutical carrier, which is carried out according to a conventional pharmaceutical Formulation technique. The carrier can be used in a wide variety of forms depending on the form of preparation which is designed for different administration modes (for example, oral or parenteral administration). Suitable pharmaceutically acceptable carriers are well known in the art. A description of some of these pharmaceutically acceptable carriers can be found in the Handbook of Pharmaceutical Excipients, published jointly by the American Pharmaceutical Association and the Pharmaceutical Society of Great Britain.

The pharmaceutical composition of the present disclosure may have the following forms, for example, those suitable for oral administration, such as tablets, capsules, pills, powders, sustained release forms, solutions or suspensions; those for parenteral injections such as clear solutions, suspensions, emulsion; or those for topical use such as ointments, creams; or as a suppository for rectal administration. The pharmaceutical ingredients may also be presented in unit dosage form for single administration in a precise dosage. The pharmaceutical ingredient will include a conventional pharmaceutical carrier or excipient and a compound as an active ingredient prepared according to the present disclosure, and may also include other medical or pharmaceutical preparations, carriers, adjuvants, and the like.

Therapeutic compounds can also be administered to mammals other than humans. The drug dosage for a mammal will depend on the species of the animal and its disease condition or its disordered condition. The therapeutic compound can be administered to the animal in the form of a capsule, a bolus, or a tablet or liquid. The therapeutic compound can also be introduced into the animal by injection or infusion. These drug forms are prepared in a traditional manner complying with standard veterinary practice. As an alternative, the therapeutic compounds can be mixed with the animal feed and fed to the animal, so that the concentrated feed additive or premix can be prepared by mixing ordinary animal feed.

It is a further object of the present disclosure to provide a method for treating cancer in a subject in need thereof, including a method for administering to the subject a therapeutically effective amount of a composition containing the compound of the present disclosure.

The present disclosure also includes the use of a compound of the present disclosure, or a pharmaceutically acceptable derivative thereof, in the manufacture of a medicament for treating cancer (including non-solid tumors, solid tumors, primary or metastatic cancer, as indicated elsewhere herein and including one or more of other therapies to which the cancer is resistant or refractory), as well as other diseases (including, but not limited to, ocular fundus diseases, psoriasis, atheroma, pulmonary fibrosis, liver fibrosis, myelofibrosis, and the like). The cancer includes, but is not limited to any one of non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, and cholangiocarcinoma.

The present disclosure also provides methods for preparing corresponding compounds. Various synthetic methods can be used to prepare the compounds described herein, including the following methods. The compound disclosed herein or a pharmaceutically acceptable salt, an isomer or a hydrate thereof can be synthesized using the following methods and synthetic methods known in the field of organic chemical synthesis, or by variations of these methods as understood by those skilled in the art. Preferred methods include, but are not limited to, the following methods.

In one embodiment, the compound disclosed herein, or a pharmaceutically acceptable salt, an isomer or a hydrate thereof, is prepared by the following method, wherein X is N or O, and $R^1$, $R^2$, $R^3$, $R^4$ and $R^5$ are as described above,

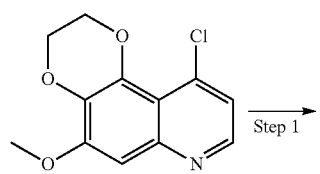

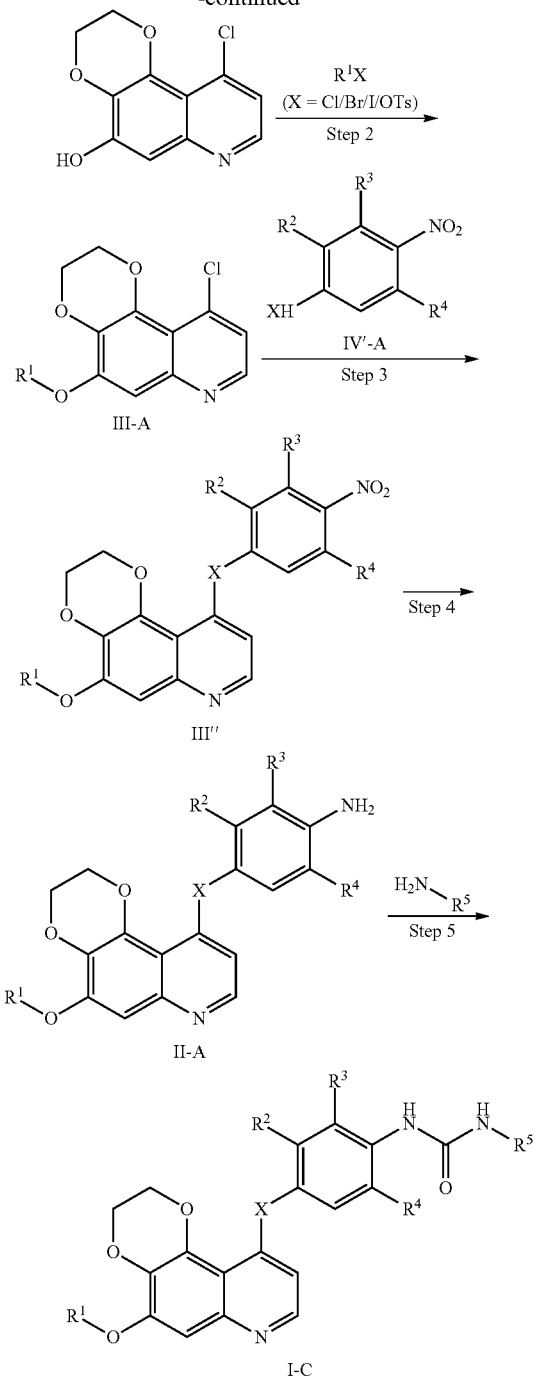

The intermediate, 10-chloro-5-methoxy-2,3-dihydro-[1,4]dioxino[2,3-f]quinoline, was synthesized by the synthetic route in the patent application CN201810160412X.

Reaction Conditions:

In step 1), 10-chloro-5-methoxy-2,3-dihydro-[1,4]dioxino[2,3-f]quinoline is dissolved in an organic solvent and subjected to the action of Lewis acid to afford 5-hydroxy-10-chloro-2,3-dihydro-[1,4]dioxino[2,3-f]quinoline, wherein the Lewis acid is boron tribromide or boron trichloride, and the organic solvent is dichloromethane.

In step 2), 5-hydroxy-10-chloro-2,3-dihydro-[1,4]dioxino[2,3-f]quinoline is reacted with $R^1X$ in an organic solvent to afford a compound of formula III-A, in which $R^1$ is as defined above; the organic solvent includes, but is not limited to, one or a combination of two or more of tetrahydrofuran, dioxane, DMF, DMA, DMSO, and acetonitrile; X in $R^1X$ is chlorine, bromine, iodine, mesylate, p-toluenesulfonate or triflate.

In step 3), the compound of formula III-A is dissolved in an organic solvent, mixed with the compound of formula IV'-A and heated to 100° C. to 140° C. to afford the compound of formula III"; and the organic solvent is selected from the group consisting of one or a combination of two or more of toluene, chlorobenzene, xylene, DMF, DMA, and DMSO.

In step 4), a nitro reduction reaction is carried out, which can be conventionally carried out by those skilled in the art; and preferably, the conditions of the nitro reduction reaction include, but are not limited to, hydrogen and Raney nickel, hydrogen and palladium/carbon, iron powder, zinc powder, and stannous chloride.

In step 5), the compound of formula (II-A) is reacted with the compound of formula $NH_2$—$R^5$ in the presence of a condensing agent to afford a compound of formula (I-C);

preferably, the condensing agent includes, but is not limited to, triphosgene, carbonyldiimidazole, phenyl chloroformate, and phenyl p-nitrochloroformate;

the reaction can also be carried out in the presence of a base, which includes, but is not limited to, one or a combination of two or more of triethylamine, diisopropylethylamine, pyridine, 4-dimethylaminopyridine, 1,8-diazabicycloundec-7-ene and N-methylmorpholine; aprotic solvents include, but are not limited to, one or a combination of two or more of dichloromethane, tetrahydrofuran, DMF, dioxane, and dichloroethane.

Alternatively, step 5) is carried out in an aprotic solvent, which includes, but is not limited to, one and a combination of two or more of dichloromethane, tetrahydrofuran, DMF, dioxane, and dichloroethane;

when $R^1$ is —$CH_3$, step 1) and step 2) can be omitted, and the operation of step 3) can be directly carried out. Meanwhile, the order of steps 1 and 2 and step 3 may not be fixed. For example, step 3 may be carried out first, followed by steps 1 and 2.

In order to make the objectives, technical solutions and advantages of the present disclosure more clear, the present disclosure will be further described in detail below in conjunction with specific examples. It should be understood that the specific examples described here are only used to explain the present disclosure and are not intended to limit the present invention. If no specific technology or conditions are indicated in examples, the technology or conditions described in the literature in the art or the product specification shall be followed. If reagents or instruments used do not indicate manufacturers, they are all conventional products that are commercially available. The term "and/or" as used herein includes any and all combinations of one or more related listed items. The examples provided below can better illustrate the present disclosure. Unless otherwise specified, all temperatures are in degrees Celsius.

Example 1: Preparation of 1-(4-chloro-3-(trifluoromethyl)phenyl)-3-(4-((5-methoxy-2,3-dihydro-[1,4]dioxino[2,3-f]quinolin-10-yl)oxy)phenyl)urea

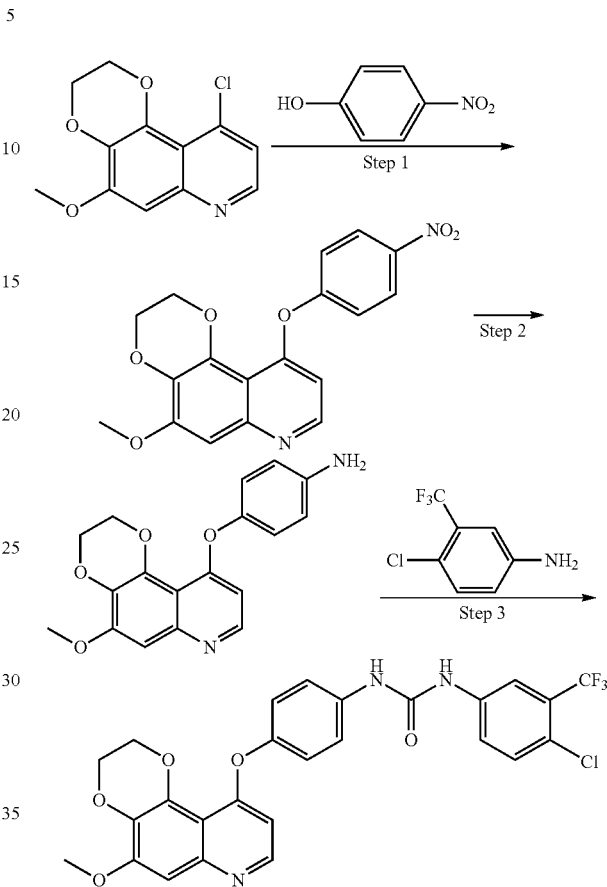

Step 1): 10-Chloro-5-methoxy-2,3-dihydro-[1,4]dioxino[2,3-f]quinoline (251 mg, 1 mmol, referring to patent application CN201810160412X for the synthetic route) and p-nitrophenol (139 mg, 1 mmol) were placed in a reaction flask, to which chlorobenzene was then added. The mixture was heated to reflux with stirring until the reaction was completed. After cooling, the mixture was filtered with suction. The resulting solid was washed with an aqueous solution of potassium carbonate to afford 250 mg of a light yellow solid (5-methoxy-10-(4-nitrophenoxy)-2,3-dihydro-[1,4]dioxino[2,3-f]quinoline) with a yield of 71%. MS: 355[M+H]$^+$.

Step 2): The product prepared in step 1 (250 mg, 0.7 mmol) was placed in a reaction flask, to which methanol and Raney nickel (250 mg) were then added. The reaction solution was stirred under hydrogen atmosphere until the reaction was completed. The mixture was filtered with suction and concentrated to afford 226 mg of an off-white solid product (4-((5-methoxy-2,3-dihydro-[1,4]dioxino[2,3-f]quinolin-10-yl)oxy)aniline) with a yield of 99%. MS: 325[M+H]$^+$.

Step 3): Triphosgene (296 mg, 1 mmol) was dissolved in tetrahydrofuran, to which 4-chloro-3-(trifluoromethyl)aniline (195 mg, 1 mmol) and triethylamine (0.4 mL, 3 mmol) were then added. After stirring for 1 hour, a solution of the product of step 2 (226 mg, 0.7 mmol) and triethylamine (0.4 mL, 3 mmol) in tetrahydrofuran was added and stirred until the reaction was completed. An aqueous solution of sodium carbonate was added to the reaction solution, which was then extracted with ethyl acetate. The organic phase was concentrated and subjected to column chromatography to afford 306 mg of a white solid with a yield of 80%. ¹HNMR (400 MHz, DMSO-d₆) δ 9.22 (s, 1H), 8.97 (s, 1H), 8.42 (d, J=5.2 Hz, 1H), 8.12 (d, J=2.4 Hz, 1H), 7.73-7.59 (m, 2H), 7.59-7.49 (m, 2H), 7.15-6.98 (m, 3H), 6.44 (d, J=5.2 Hz, 1H), 4.34 (s, 4H), 3.93 (s, 3H); MS: 546[M+H]⁺.

Example 2: Preparation of 1-(2-fluoro-5-(trifluoromethyl)phenyl)-3-(4-((5-methoxy-2,3-dihydro-[1,4]dioxino[2,3-f]quinolin-10-yl)oxy)phenyl)urea The preparation was carried out in a similar manner to Example 1, except that in step 3, an equimolar equivalent of 2-fluoro-5-(trifluoromethyl)aniline was used in place of 4-chloro-3-(trifluoromethyl)aniline. ¹H NMR (400 MHz, DMSO-d₆) δ 9.26 (s, 1H), 8.90 (d, J=2.9 Hz, 1H), 8.62 (dd, J=7.4, 2.4 Hz, 1H), 8.42 (d, J=5.2 Hz, 1H), 7.61-7.45 (m, 3H), 7.45-7.34 (m, 1H), 7.15-7.02 (m, 3H), 6.44 (d, J=5.2 Hz, 1H), 4.39-4.27 (m, 4H), 3.92 (s, 3H). MS: 530[M+H]⁺.

Example 2

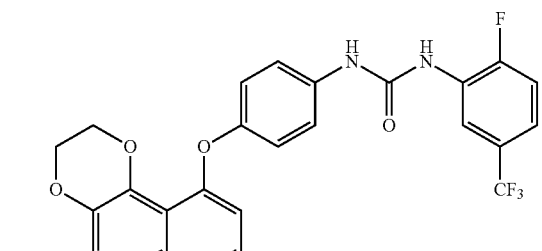

Example 3

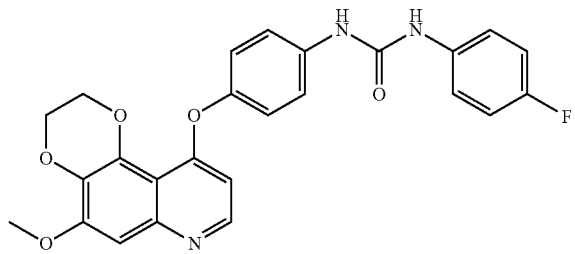

Example 3: Preparation of 1-(4-fluorophenyl)-3-(4-((5-methoxy-2,3-dihydro-[1,4]dioxino[2,3-f]quinolin-10-yl)oxy)phenyl)urea The preparation was carried out in a similar manner to Example 1, except that in step 3, an equimolar equivalent of p-fluoroaniline was used in place of 4-chloro-3-(trifluoromethyl)aniline. ¹H NMR (600 MHz, DMSO-d₆) δ 9.34 (d, J=23.8 Hz, 2H), 8.40 (d, J=5.2 Hz, 1H), 7.56 (dd, J=8.9, 2.1 Hz, 2H), 7.53-7.46 (m, 2H), 7.15-7.09 (m, 2H), 7.09-7.04 (m, 3H), 6.41 (d, J=5.2 Hz, 1H), 4.42-4.28 (m, 4H), 3.92 (s, 3H). MS: 462[M+H]⁺.

Example 4: Preparation of 1-(2,4-difluorophenyl)-3-(4-((5-methoxy-2,3-dihydro-[1,4]dioxino[2,3-f]quinolin-10-yl)oxy) phenyl)urea The preparation was carried out in a similar manner to Example 1, except that in step 3, an equimolar equivalent of 2,4-difluoroaniline was used in place of 4-chloro-3-(trifluoromethyl)aniline. ¹H NMR (600 MHz, DMSO-d₆) δ 9.19 (s, 1H), 8.58 (d, J=2.2 Hz, 1H), 8.41 (d, J=5.2 Hz, 1H), 8.13-8.03 (m, 1H), 7.59-7.50 (m, 2H), 7.36-7.26 (m, 1H), 7.13-7.01 (m, 4H), 6.42 (d, J=5.2 Hz, 1H), 4.38-4.30 (m, 4H), 3.92 (s, 3H). MS: 480[M+H]⁺.

Example 4

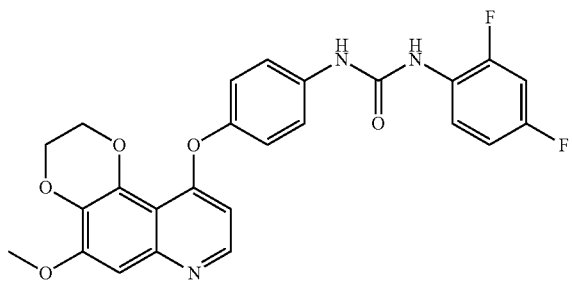

Example 5

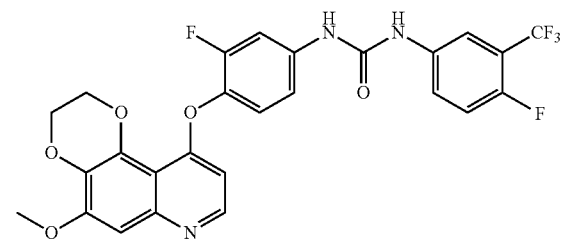

Example 5: Preparation of 1-(4-chloro-3-(trifluoromethyl)phenyl)-3-(3-fluoro-4-((5-methoxy-2,3-dihydro-[1,4]dioxino[2,3-f]quinolin-10-yl)oxy)phenyl)urea The preparation was carried out in a similar manner to Example 1, except that in step 1, an equimolar equivalent of 2-fluoro-4-nitrophenol was used in place of p-nitrophenol. ¹HNMR (400 MHz, DMSO-d₆) δ 9.32 (s, 1H), 9.22 (s, 1H), 8.48 (d, J=5.3 Hz, 1H), 8.16 (d, J=2.5 Hz, 1H), 7.82-7.61 (m, 3H), 7.37-7.24 (m, 2H), 7.13 (s, 1H), 6.47 (d, J=5.3 Hz, 1H), 4.41 (s, 4H), 3.98 (s, 3H); ¹³CNMR (101 MHz, DMSO-d₆) δ 161.1, 152.8, 152.5, 152.4, 149.6, 146.6, 139.5, 138.2, 138.2, 136.0, 132.4, 132.3, 123.8, 123.7, 123.0, 117.4, 115.7, 107.9, 107.7, 103.9, 101.5, 64.5, 63.9, 56.2, 49.0; MS: 564[M+H]⁺.

Example 6: Preparation of 1-(4-chloro-3-(trifluoromethyl)phenyl)-3-(2-fluoro-4-((5-methoxy-2,3-dihydro-[1,4]dioxino[2,3-f]quinolin-10-yl)oxy)phenyl)urea The preparation was carried out in a similar manner to Example 1, except that in step 1, an equimolar equivalent of 3-fluoro-4-nitrophenol was used in place of p-nitrophenol. ¹HNMR (400 MHz, DMSO-d₆) δ 9.48 (s, 1H), 8.66 (d, J=2.3 Hz, 1H), 8.48 (d, J=5.2 Hz, 1H), 8.20-8.00 (m, 2H), 7.62 (d, J=1.5 Hz, 2H), 7.20-7.13 (m, 1H), 7.09 (s, 1H), 6.97-6.87 (m, 1H), 6.59 (d, J=5.2 Hz, 1H), 4.52-4.18 (m, 4H), 3.93 (s, 3H); ¹³CNMR (101 MHz, DMSO-d₆) δ 160.4, 152.7, 152.4, 149.7, 146.8, 139.5, 138.0, 132.5, 132.3, 123.4, 123.1, 117.10, 116.1, 108.8, 108.3, 106.7, 101.6, 64.4, 63.9, 56.2, 40.2; MS: 564[M+H]⁺.

Example 6

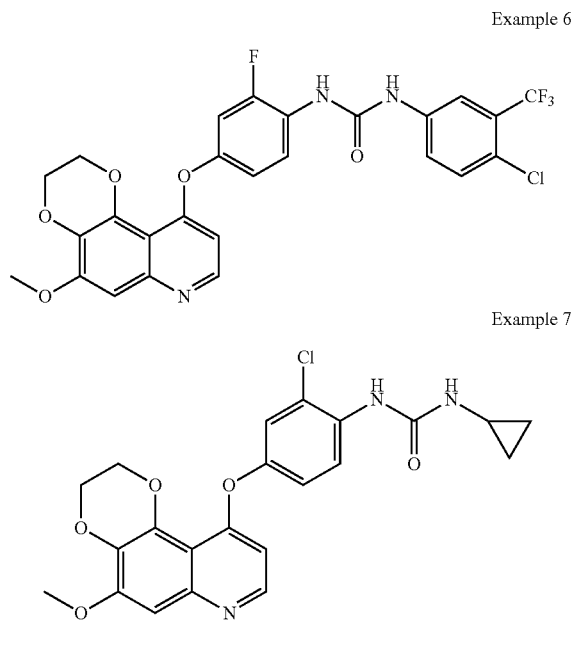

Example 7

Example 7: Preparation of 1-(2-chloro-4-((5-methoxy-2,3-dihydro-[1,4]dioxino[2,3-f]quinolin-10-yl)oxy)phenyl)-3-cyclopropylurea The preparation was carried out in a similar manner to Example 1, except that in step 1, an equimolar equivalent of 3-chloro-4-nitrophenol was used in place of p-nitrophenol. $^1$H NMR (600 MHz, DMSO-$d_6$) δ 8.45 (d, J=5.2 Hz, 1H), 8.17 (d, J=9.0 Hz, 1H), 7.90 (s, 1H), 7.25 (d, J=2.8 Hz, 1H), 7.14 (d, J=2.9 Hz, 1H), 7.10-7.02 (m, 2H), 6.54-6.48 (m, 1H), 4.35-4.26 (m, 4H), 3.92 (s, 3H), 2.60-2.52 (m, 1H), 0.70-0.61 (m, 2H), 0.46-0.38 (m, 2H). MS: 442[M+H]$^+$.

Example 8: Preparation of 1-(4-chloro-3-(trifluoromethyl)phenyl)-3-(4-((5-(2-methoxyethoxy)-2,3-dihydro-[1,4]dioxino[2,3-f]quinolin-10-yl)oxy)phenyl)urea

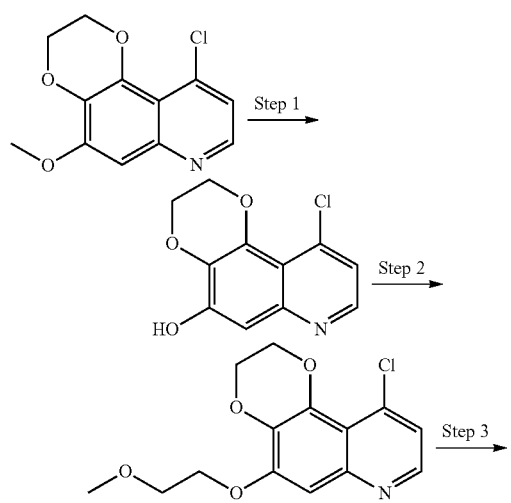

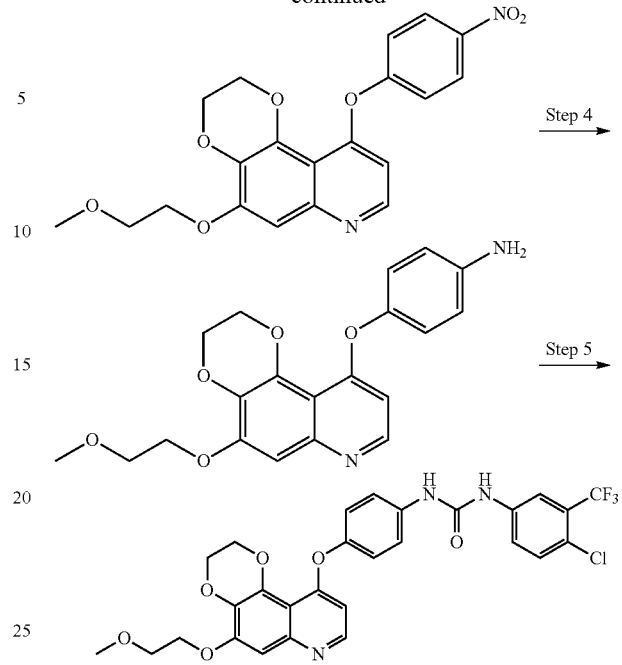

Step 1): 10-Chloro-5-methoxy-2,3-dihydro-[1,4]dioxino[2,3-f]quinoline (251 mg, 1 mmol) was dissolved in dichloromethane, to which a 1 mol/liter solution of boron tribromide in dichloromethane (3 mL, 3 mmol) was then added dropwise. The reaction solution was stirred until the reaction was completed. The mixture was concentrated to afford 236 mg of a light yellow solid product (5-hydroxy-10-chloro-2,3-dihydro-[1,4]dioxino[2,3-f]quinoline) in a yield of 99%. MS: 238[M+H]$^+$.

Step 2): The product obtained in step 1 (236 mg, 1 mmol) was dissolved in N,N-dimethylformamide, to which 1-bromo-2-methoxyethane (138 mg, 1 mmol) and potassium carbonate (414 mg, 3 mmol) were then added. The mixture was heated with stirring until the reaction was completed. Water was added to the reaction solution, which was then extracted with ethyl acetate. The organic phase was concentrated, and then subjected to column chromatography to afford 236 mg of an off-white solid (10-chloro-5-(2-methoxyethoxy)-2,3-dihydro-[1,4]dioxino[2,3-f]quinoline) with a yield of 80%. $^1$H NMR (400 MHz, DMSO-$d_6$) δ 8.70-8.46 (m, 1H), 7.50-7.33 (m, 1H), 7.25-7.09 (m, 1H), 4.40 (s, 4H), 4.30-4.23 (m, 2H), 3.77-3.71 (m, 2H), 3.33-3.32 (m, 3H); MS: 296[M+H]$^+$.

Steps 3-5): Steps 3-5) were carried out in a similar manner to Example 1, except that in step 3), an equimolar equivalent of the product prepared in step 2) (10-chloro-5-(2-methoxyethoxy)-2,3-dihydro-[1,4]dioxino[2,3-f]quinoline) was used in place of 10-chloro-5-methoxy-2,3-dihydro-[1,4]dioxino[2,3-f]quinoline in step 1) of Example 1. $^1$H NMR (400 MHz, DMSO-$d_6$) δ 9.19 (s, 1H), 8.95 (s, 1H), 8.41 (d, J=5.1 Hz, 1H), 8.12 (d, J=2.4 Hz, 1H), 7.71-7.59 (m, 2H), 7.59-7.47 (m, 2H), 7.14-7.01 (m, 3H), 6.43 (d, J=5.1 Hz, 1H), 4.40-4.29 (m, 4H), 4.25 (t, J=4.3 Hz, 2H), 3.74 (t, J=4.4 Hz, 2H), 3.35 (s, 3H). MS: 590[M+H]$^+$.

Example 9: Preparation of 1-(4-chloro-3-(trifluoromethyl)phenyl)-3-(4-((5-ethoxy-2,3-dihydro-[1,4]dioxino[2,3-f]quinolin-10-yl)oxy)phenyl)urea The preparation was carried out in a similar manner to Example 8, except that an equimolar equivalent of iodoethane was used in place of 1-bromo-2-methoxyethane in step 2) of Example 8. ¹H NMR (400 MHz, DMSO-d₆) δ 9.14 (s, 1H), 8.89 (s, 1H), 8.34 (d, J=5.2 Hz, 1H), 8.05 (d, J=2.4 Hz, 1H), 7.62-7.51 (m, 2H), 7.51-7.43 (m, 2H), 7.06-6.99 (m, 2H), 6.97 (s, 1H), 6.35 (d, J=5.2 Hz, 1H), 4.33-4.19 (m, 4H), 4.11 (q, J=6.9 Hz, 2H), 1.35 (t, J=6.9 Hz, 3H). MS: 560 [M+H]⁺.

Example 9

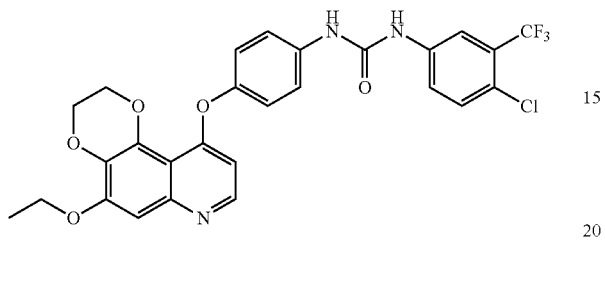

Example 10

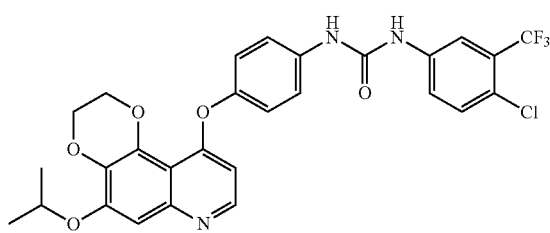

Example 10: Preparation of 1-(4-chloro-3-(trifluoromethyl)phenyl)-3-(4-((5-isopropoxy-2,3-dihydro-[1,4]dioxino[2,3-f]quinolin-10-yl)oxy)phenyl)urea The preparation was carried out in a similar manner to Example 8, except that an equimolar equivalent of isopropyl bromide was used in place of 1-bromo-2-methoxyethane in step 2) of Example 8. ¹H NMR (400 MHz, DMSO-d₆) δ 9.17 (s, 1H), 8.93 (s, 1H), 8.40 (d, J=5.2 Hz, 1H), 8.12 (d, J=2.4 Hz, 1H), 7.73-7.47 (m, 4H), 7.16-6.92 (m, 3H), 6.42 (d, J=5.2 Hz, 1H), 4.81 (p, J=6.1 Hz, 1H), 4.38-4.21 (m, 4H), 1.36 (d, J=6.0 Hz, 6H). MS: 574[M+H]⁺.

Example 11: Preparation of 1-(4-chloro-3-(trifluoromethyl)phenyl)-3-(4-((5-isobutoxy-2,3-dihydro-[1,4]dioxino[2,3-f]quinolin-10-yl)oxy)phenyl)urea The preparation was carried out in a similar manner to Example 8, except that an equimolar equivalent of isobutyl bromide was used in place of 1-bromo-2-methoxyethane in step 2) of Example 8. ¹H NMR (400 MHz, DMSO-d₆) δ 9.19 (s, 1H), 8.94 (s, 1H), 8.41 (d, J=5.1 Hz, 1H), 8.12 (d, J=2.4 Hz, 1H), 7.71-7.58 (m, 2H), 7.58-7.49 (m, 2H), 7.13-7.06 (m, 2H), 7.04 (s, 1H), 6.43 (d, J=5.2 Hz, 1H), 4.40-4.28 (m, 4H), 3.90 (d, J=6.5 Hz, 2H), 2.19-2.03 (m, 1H), 1.03 (d, J=6.6 Hz, 6H). MS: 588[M+H]⁺.

Example 11

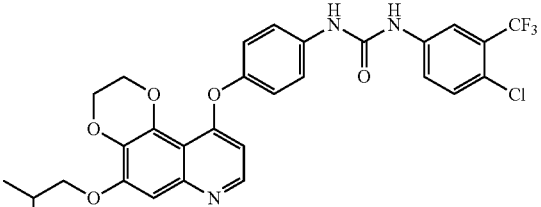

Example 12

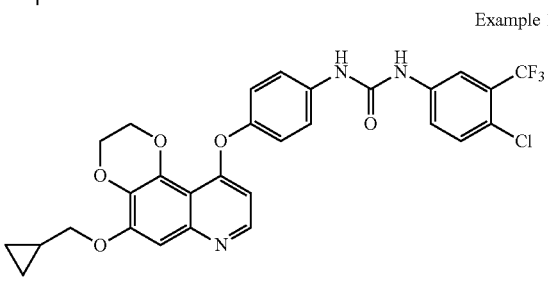

Example 12: Preparation of 1-(4-chloro-3-(trifluoromethyl)phenyl)-3-(4-((5-(cyclopropylmethoxy)-2,3-dihydro-[1,4]dioxino[2,3-f]quinolin-10-yl)oxy)phenyl)urea The preparation was carried out in a similar manner to Example 8, except that an equimolar equivalent of bromomethylcyclopropane was used in place of 1-bromo-2-methoxyethane in step 2) of Example 8. ¹H NMR (400 MHz, DMSO-d₆) δ 9.12 (s, 1H), 8.88 (s, 1H), 8.33 (d, J=5.2 Hz, 1H), 8.05 (d, J=2.4 Hz, 1H), 7.63-7.52 (m, 2H), 7.52-7.43 (m, 2H), 7.07-6.97 (m, 2H), 6.94 (s, 1H), 6.35 (d, J=5.2 Hz, 1H), 4.33-4.21 (m, 4H), 3.90 (d, J=7.0 Hz, 2H), 1.31-1.18 (m, 1H), 0.60-0.49 (m, 2H), 0.37-0.30 (m, 2H). MS: 586 [M+H]⁺.

Example 13: Preparation of 1-(4-chloro-3-(trifluoromethyl)phenyl)-3-(4-((5-(cyanomethoxy)-2,3-dihydro-[1,4]dioxino[2,3-f]quinolin-10-yl)oxy)phenyl) urea The preparation was carried out in a similar manner to Example 8, except that an equimolar equivalent of bromoacetonitrile was used in place of 1-bromo-2-methoxyethane in step 2) of Example 8. ¹H NMR (600 MHz, DMSO-d₆) δ 9.21 (s, 1H), 8.97 (s, 1H), 8.47 (d, J=5.2 Hz, 1H), 8.12 (d, J=2.5 Hz, 1H), 7.69-7.59 (m, 2H), 7.59-7.51 (m, 2H), 7.26 (s, 1H), 7.15-7.07 (m, 2H), 6.48 (d, J=5.2 Hz, 1H), 5.37 (s, 2H), 4.42-4.32 (m, 4H). MS: 571 [M+H]⁺.

Example 13

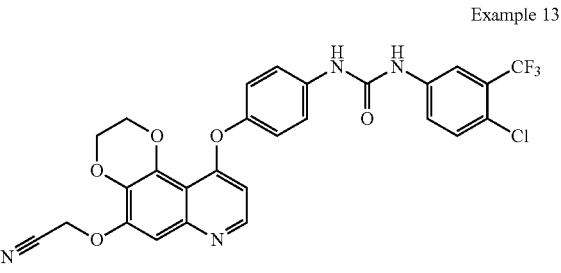

Example 14

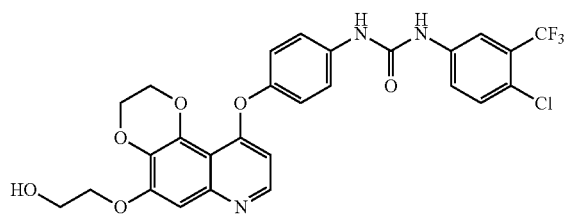

Example 14: Preparation of 1-(4-chloro-3-(trifluoromethyl)phenyl)-3-(4-((5-(2-hydroxyethoxy)-2,3-dihydro-[1,4]dioxino[2,3-f]quinolin-10-yl)oxy)phenyl)urea The preparation was carried out in a similar manner to Example 8, except that an equimolar equivalent of 2-bromoethan-1-ol was used in place of 1-bromo-2-methoxyethane in step 2) of Example 8. $^1$H NMR (400 MHz, DMSO-d$_6$) δ 9.18 (s, 1H), 8.94 (s, 1H), 8.41 (dd, J=5.2, 1.7 Hz, 1H), 8.11 (d, J=2.4 Hz, 1H), 7.73-7.58 (m, 2H), 7.58-7.50 (m, 2H), 7.16-7.01 (m, 3H), 6.43 (dd, J=5.2, 1.8 Hz, 1H), 4.98-4.88 (m, 1H), 4.40-4.26 (m, 4H), 4.14 (t, J=4.9 Hz, 2H), 3.85-3.72 (m, 2H). MS: 576[M+H]$^+$.

Example 15: Preparation of 1-(4-chloro-3-(trifluoromethyl)phenyl)-3-(4-((5-(3-hydroxypropoxy)-2,3-dihydro-[1,4]dioxino[2,3-f]quinolin-10-yl)oxy)phenyl)urea The preparation was carried out in a similar manner to Example 8, except that an equimolar equivalent of 3-bromopropan-1-ol was used in place of 1-bromo-2-methoxyethane in step 2) of Example 8. $^1$H NMR (400 MHz, DMSO-d$_6$) δ 9.24 (s, 1H), 8.99 (s, 1H), 8.41 (d, J=5.2 Hz, 1H), 8.12 (d, J=2.5 Hz, 1H), 7.70-7.58 (m, 2H), 7.58-7.51 (m, 2H), 7.14-7.02 (m, 3H), 6.42 (d, J=5.2 Hz, 1H), 4.58 (t, J=5.2 Hz, 1H), 4.41-4.27 (m, 4H), 4.19 (t, J=6.4 Hz, 2H), 3.66-3.54 (m, 2H), 1.95 (t, J=6.3 Hz, 2H). MS: 590[M+H]$^+$.

Example 16: Preparation of 1-(4-chloro-3-(trifluoromethyl)phenyl)-3-(4-((5-(3-methoxypropoxy)-2,3-dihydro-[1,4]dioxino[2,3-f]quinolin-10-yl)oxy)phenyl)urea The preparation was carried out in a similar manner to Example 8, except that an equimolar equivalent of 1-bromo-3-methoxypropane was used in place of 1-bromo-2-methoxyethane in step 2) of Example 8. $^1$H NMR (600 MHz, DMSO-d$_6$) δ 9.17 (s, 1H), 8.93 (s, 1H), 8.41 (d, J=5.2 Hz, 1H), 8.11 (d, J=2.5 Hz, 1H), 7.72-7.58 (m, 2H), 7.58-7.50 (m, 2H), 7.13-7.06 (m, 2H), 7.04 (s, 1H), 6.43 (d, J=5.2 Hz, 1H), 4.40-4.26 (m, 4H), 4.17 (t, J=6.4 Hz, 2H), 3.52 (t, J=6.3 Hz, 2H), 3.27 (s, 3H), 2.07-1.98 (m, 2H). MS: 604[M+H]$^+$.

Example 17: Preparation of 1-(4-chloro-3-(trifluoromethyl)phenyl)-3-(4-((5-(3-(dimethylamino)propoxy)-2,3-dihydro-[1, 4]dioxino[2,3-f]quinolin-10-yl)oxy)phenyl)urea The preparation was carried out in a similar manner to Example 8, except that an equimolar equivalent of 3-chloro-N,N-dimethylpropan-1-amine hydrochloride was used in place of 1-bromo-2-methoxyethane in step 2) of Example 8. $^1$H NMR (400 MHz, Methanol-d$_4$) δ 8.42 (d, J=5.4 Hz, 1H), 8.08 (d, J=2.6 Hz, 1H), 7.71 (dd, J=8.7, 2.6 Hz, 1H), 7.64-7.54 (m, 3H), 7.17-7.11 (m, 2H), 7.09 (s, 1H), 6.59 (d, J=5.4 Hz, 1H), 4.49-4.39 (m, 4H), 4.29 (t, J=6.0 Hz, 2H), 2.82 (t, J=7.6 Hz, 2H), 2.50 (s, 6H), 2.26-2.15 (m, 2H). MS: 617[M+H]$^+$.

Example 15

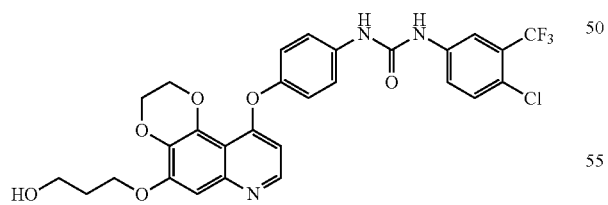

Example 16

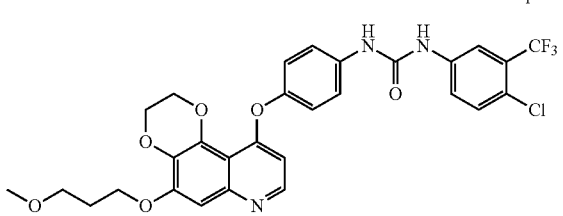

Example 17

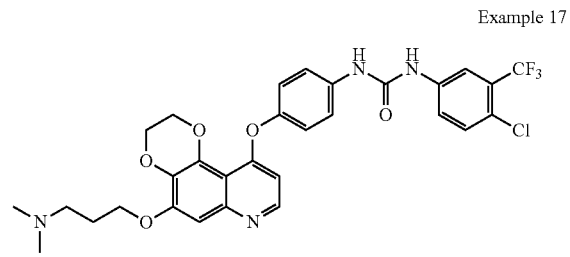

Example 18

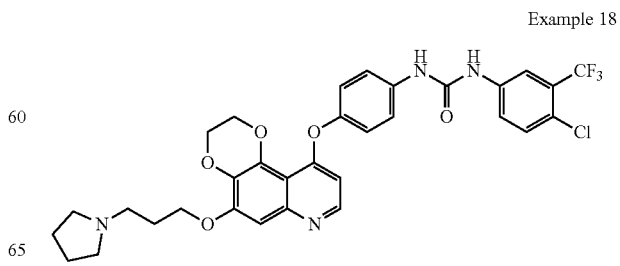

Example 18: Preparation of 1-(4-chloro-3-(trifluoromethyl)phenyl)-3-(4-((5-(3-(pyrrolidin-1-yl)propoxy)-2,3-dihydro-[1,4]dioxino[2,3-f]quinolin-10-yl)oxy)phenyl)urea The preparation was carried out in a similar manner to Example 8, except that an equimolar equivalent of 1-(3-chloropropyl)pyrrolidine hydrochloride was used in place of 1-bromo-2-methoxyethane in step 2) of Example 8. $^1$H NMR (600 MHz, DMSO-$d_6$) δ 9.27 (s, 1H), 9.02 (s, 1H), 8.40 (d, J=5.2 Hz, 1H), 8.12 (d, J=2.6 Hz, 1H), 7.70-7.58 (m, 2H), 7.58-7.50 (m, 2H), 7.12-7.05 (m, 2H), 7.03 (d, J=5.0 Hz, 1H), 6.42 (d, J=5.2 Hz, 1H), 4.39-4.27 (m, 4H), 4.20-4.11 (m, 2H), 2.58-2.54 (m, 2H), 2.48-2.42 (m, 4H), 2.00-1.92 (m, 2H), 1.75-1.64 (m, 4H). MS: 643[M+H]$^+$.

Example 19: Preparation of 1-(4-chloro-3-(trifluoromethyl)phenyl)-3-(4-((5-(3-(piperidin-1-yl)propoxy)-2,3-dihydro-[1,4]dioxino[2,3-f]quinolin-10-yl)oxy)phenyl)urea The preparation was carried out in a similar manner to Example 8, except that an equimolar equivalent of 1-(3-chloropropyl)piperidine hydrochloride was used in place of 1-bromo-2-methoxyethane in step 2) of Example 8. $^1$H NMR (400 MHz, DMSO-d6) δ 9.97 (s, 1H), 9.67 (s, 1H), 8.40 (d, J=5.2 Hz, 1H), 8.27 (s, 1H), 8.15 (d, J=2.6 Hz, 1H), 7.70 (dd, J=8.8, 2.6 Hz, 1H), 7.64-7.55 (m, 3H), 7.13-6.99 (m, 3H), 6.42 (d, J=5.2 Hz, 1H), 4.42-4.25 (m, 4H), 4.16 (t, J=6.4 Hz, 2H), 3.35-3.21 (m, 4H), 2.57 (t, J=7.3 Hz, 2H), 1.99 (t, J=7.0 Hz, 2H), 1.62-1.49 (m, 4H), 1.47-1.35 (m, 2H). MS: 657[M+H]$^+$.

Example 20: Preparation of 1-(4-chloro-3-(trifluoromethyl)phenyl)-3-(4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8. $^1$H NMR (400 MHz, DMSO-$d_6$) δ 9.22 (s, 1H), 8.97 (s, 1H), 8.41 (d, J=5.2 Hz, 1H), 8.12 (d, J=2.4 Hz, 1H), 7.70-7.58 (m, 2H), 7.58-7.50 (m, 2H), 7.14-6.99 (m, 3H), 6.43 (d, J=5.2 Hz, 1H), 4.39-4.26 (m, 4H), 4.17 (t, J=6.4 Hz, 2H), 3.38-3.23 (m, 4H), 2.49-2.28 (m, 6H), 2.05-1.88 (m, 2H). MS: 659 [M+H]$^+$.

Example 21: Preparation of 1-(4-chloro-3-(trifluoromethyl)phenyl)-3-(4-((5-(3-(4-methylpiperazin-1-yl)propoxy)-2,3-dihydro-[1,4]dioxino[2,3-f]quinolin-10-yl)oxy)phenyl)urea The preparation was carried out in a similar manner to Example 8, except that an equimolar equivalent of 1-(3-chloropropyl)-4-methylpiperazine hydrochloride was used in place of 1-bromo-2-methoxyethane in step 2) of Example 8. $^1$H NMR (600 MHz, DMSO-$d_6$) δ 9.20 (s, 1H), 8.95 (s, 1H), 8.41 (d, J=5.2 Hz, 1H), 8.11 (d, J=2.5 Hz, 1H), 7.70-7.58 (m, 2H), 7.58-7.50 (m, 2H), 7.14-7.05 (m, 2H), 7.03 (s, 1H), 6.42 (d, J=5.2 Hz, 1H), 4.38-4.27 (m, 4H), 4.15 (t, J=6.4 Hz, 2H), 2.50-2.49 (m, 2H), 2.45 (t, J=7.2 Hz, 2H), 2.43-2.20 (m, 6H), 2.15 (s, 3H), 1.99-1.90 (m, 2H). MS: 672[M+H]$^+$.

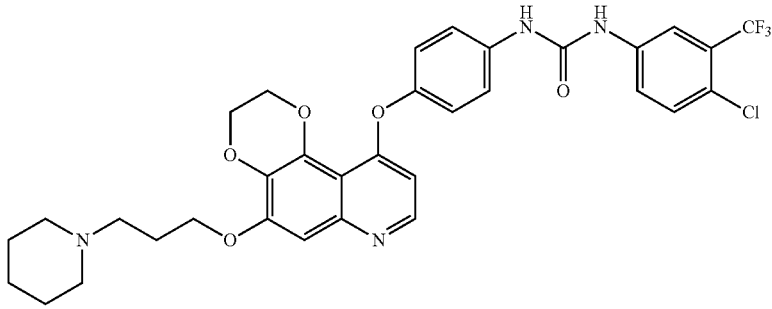

Example 19

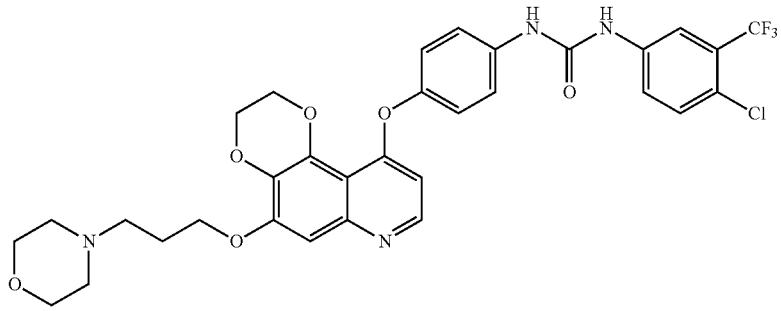

Example 20

Example 21

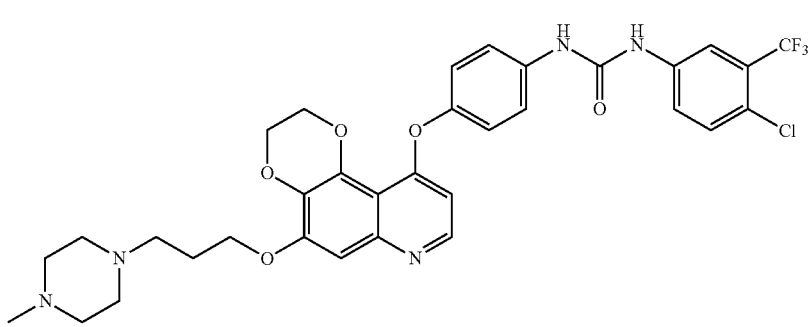

Example 22

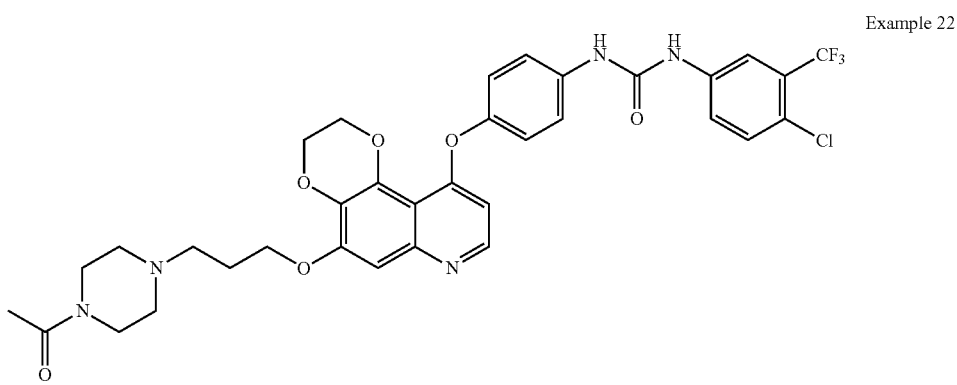

Example 22: Preparation of 1-(4-((5-(3-(4-acetylpiperazin-1-yl)propoxy)-2,3-dihydro-[1,4]dioxino[2,3-f]quinolin-10-yl)oxy)phenyl)-3-(4-chloro-3-(trifluoromethyl)phenyl)urea The preparation was carried out in a similar manner to Example 8, except that an equimolar equivalent of 1-(4-(3-chloropropyl)piperazin-1-yl)ethan-1-one hydrochloride was used in place of 1-bromo-2-methoxyethane in step 2) of Example 8. $^1$H NMR (400 MHz, DMSO-$d_6$) δ 9.20 (s, 1H), 8.95 (s, 1H), 8.41 (d, J=5.2 Hz, 1H), 8.12 (d, J=2.4 Hz, 1H), 7.70-7.58 (m, 2H), 7.58-7.50 (m, 2H), 7.14-7.02 (m, 3H), 6.42 (d, J=5.2 Hz, 1H), 4.39-4.28 (m, 4H), 4.17 (t, J=6.4 Hz, 2H), 3.48-3.38 (m, 4H), 2.49-2.47 (m, 2H), 2.45-2.37 (m, 2H), 2.34 (t, J=5.1 Hz, 2H), 2.03-1.93 (m, 5H). MS: 700 [M+H]$^+$.

Example 23: Preparation of 1-(4-chloro-3-(trifluoromethyl)phenyl)-3-(4-((5-(3-(1,1-dioxothiomorpholino)propoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)thiomorpholine-1,1-dioxide hydrochloride was used in place of 1-bromo-2-methoxyethane in step 2) of Example 8. $^1$H NMR (400 MHz, DMSO-$d_6$) δ 9.21 (s, 1H), 8.96 (s, 1H), 8.41 (d, J=5.3 Hz, 1H), 8.12 (d, J=2.4 Hz, 1H), 7.70-7.58 (m, 2H), 7.58-7.50 (m, 2H), 7.13-7.04 (m, 3H), 6.42 (d, J=5.2 Hz, 1H), 4.39-4.27 (m, 4H), 4.18 (t, J=6.4 Hz, 2H), 3.16-3.06 (m, 4H), 2.98-2.87 (m, 4H), 2.71-2.61 (m, 2H), 2.03-1.89 (m, 2H). MS: 707[M+H]$^+$.

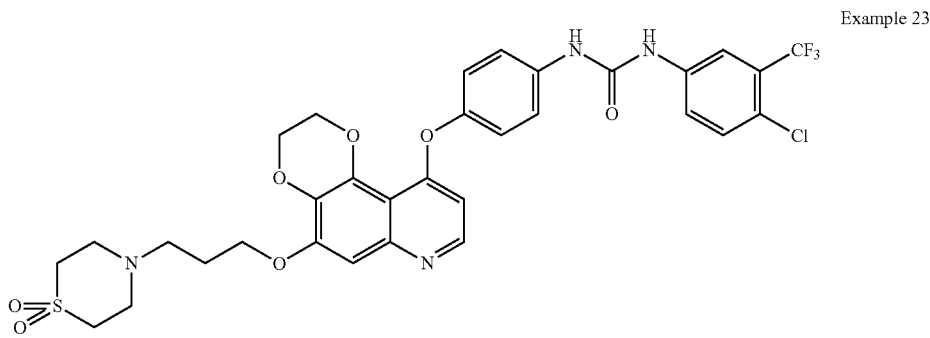

Example 23

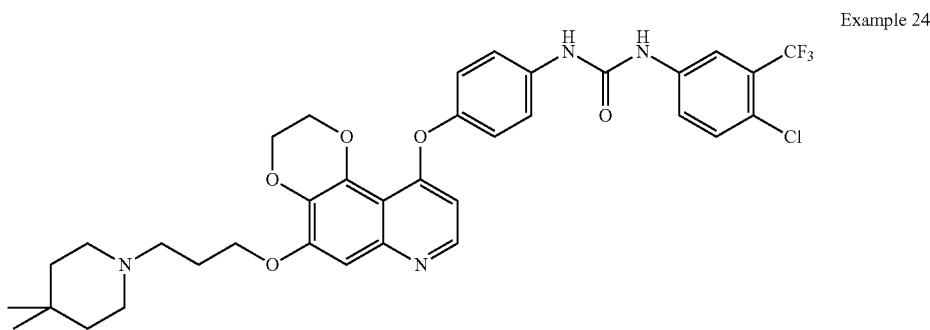

Example 24

Example 24: Preparation of 1-(4-chloro-3-(trifluoromethyl)phenyl)-3-(4-((5-(3-(4,4-dimethylpiperidin-1-yl)propoxy)-2,3-dihydro-[1,4]dioxino[2,3-f]quinolin-10-yl)oxy)phenyl)urea The preparation was carried out in a similar manner to Example 8, except that an equimolar equivalent of 1-(3-chloropropyl)-4,4-dimethylpiperidine hydrochloride was used in place of 1-bromo-2-methoxyethane in step 2 of Example 8. $^1$H NMR (400 MHz, DMSO-d$_6$) δ 9.21 (s, 1H), 8.97 (s, 1H), 8.41 (d, J=5.1 Hz, 1H), 8.12 (d, J=2.4 Hz, 1H), 7.69-7.58 (m, 2H), 7.58-7.49 (m, 2H), 7.13-7.06 (m, 2H), 7.04 (s, 1H), 6.42 (d, J=5.2 Hz, 1H), 4.40-4.26 (m, 4H), 4.15 (t, J=6.4 Hz, 2H), 2.48-2.42 (m, 2H), 2.41-2.29 (m, 4H), 2.02-1.89 (m, 2H), 1.33 (t, J=5.6 Hz, 4H), 0.89 (s, 6H). MS: 685[M+H]$^+$.

Example 25: Preparation of 1-(4-chloro-3-(trifluoromethyl)phenyl)-3-(4-((5-(3-(4-hydroxy-4-methylpiperidin-1-yl)propoxy)-2,3-dihydro-[1,4]dioxino[2,3-f]quinolin-10-yl)oxy)phenyl)urea

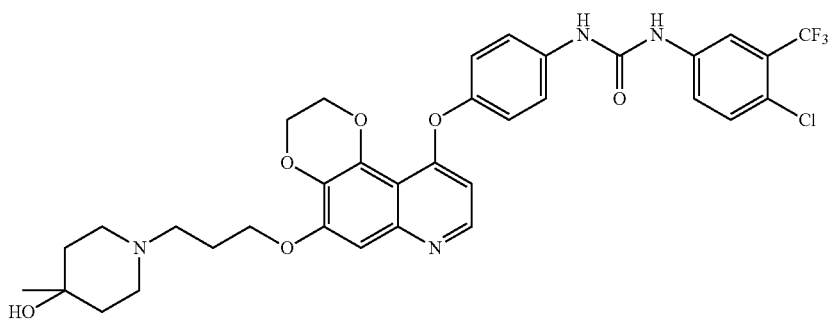 [SMILES: CC1(O)CCN(CCCOc2cc3nccc(Oc4ccc(NC(=O)Nc5ccc(Cl)c(C(F)(F)F)c5)cc4)c3c3c2OCCO3)CC1]

The preparation was carried out in a similar manner to Example 8, except that an equimolar equivalent of 1-(3-chloropropyl)-4-methylpiperidin-4-ol was used in place of 1-bromo-2-methoxyethane in step 2 of Example 8. $^1$H NMR (600 MHz, DMSO-d$_6$) δ 9.29 (s, 1H), 9.03 (s, 1H), 8.40 (d, J=5.3 Hz, 1H), 8.18-8.06 (m, 1H), 7.68-7.58 (m, 2H), 7.55 (d, J=8.9 Hz, 2H), 7.08 (d, J=8.7 Hz, 2H), 7.03 (s, 1H), 6.42 (d, J=5.3 Hz, 1H), 4.33 (dd, J=10.6, 4.9 Hz, 4H), 4.20-4.11 (m, 2H), 2.60-2.57 (m, 1H), 2.46-2.35 (m, 6H), 1.99-1.92 (m, 2H), 1.52-1.44 (m, 4H), 1.12-1.05 (m, 3H). MS: 687 [M+H]$^+$.

Example 26: Preparation of 1-(4-((5-(3-(4-amino-4-methylpiperidin-1-yl)propoxy)-2,3-dihydro-[1,4]dioxino[2,3-f]quinolin-10-yl)oxy)phenyl)-3-(4-chloro-3-(trifluoromethyl)phenyl)urea

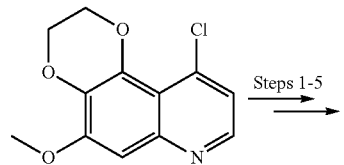

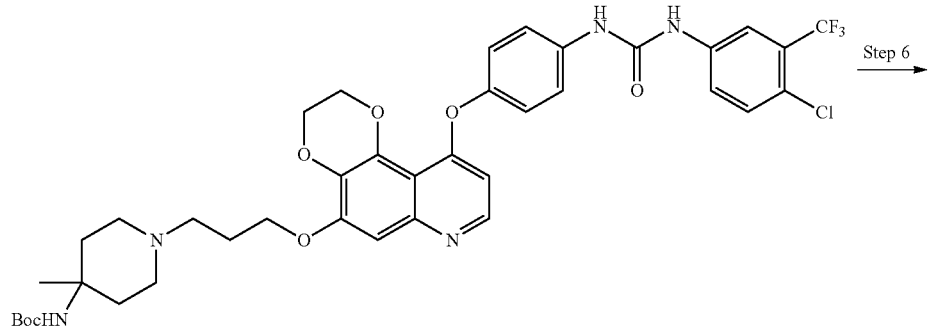

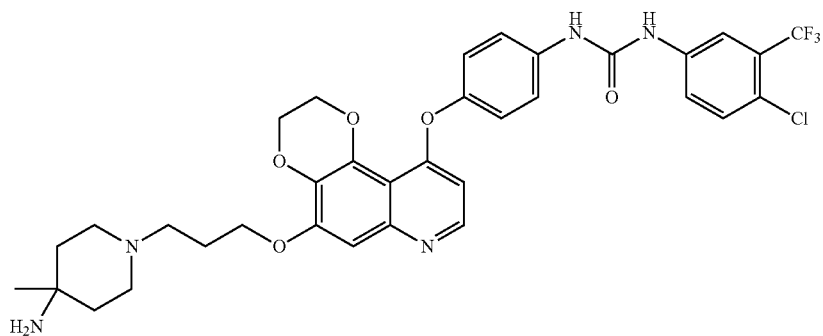

1) Steps 1-5: Preparation of tert-butyl (1-(3-((10-(4-(3-(4-chloro-3-(trifluoromethyl)phenyl)ureido)phenoxy)-2,3-dihydro-[1,4]dioxino[2,3-f]quinolin-5-yl)oxy)propyl)-4-methylpiperazin-4-yl)carbamate The preparation was carried out in a similar manner to Example 8, except that an equimolar equivalent of tert-butyl (1-(3-chloropropyl)-4-methylpiperidin-4-yl)carbamate was used in place of 1-bromo-2-methoxyethane in step 2) of Example 8. MS: 786[M+H]⁺.

2) Step 6: The final product (79 mg, 1 mmol) obtained in steps 1-5 above was dissolved in dichloromethane (3 mL), to which trifluoroacetic acid (1 mL) was then added dropwise. The mixture was reacted for 3 hours. The reaction was quenched with a solution of ammonia in methanol at 0° C. The reaction solution was evaporated to dryness and purified by column chromatography to afford 20 mg of a white solid. $^1$H NMR (400 MHz, DMSO-d$_6$) δ 9.26 (s, 1H), 9.01 (s, 1H), 8.40 (d, J=5.2 Hz, 1H), 8.12 (d, J=2.5 Hz, 1H), 7.71-7.58 (m, 2H), 7.58-7.48 (m, 2H), 7.14-7.05 (m, 2H), 7.03 (s, 1H), 6.42 (d, J=5.2 Hz, 1H), 4.39-4.28 (m, 4H), 4.15 (t, J=6.4 Hz, 2H), 2.46 (t, J=7.1 Hz, 2H), 2.43-2.28 (m, 4H), 1.99-1.87 (m, 2H), 1.78-1.47 (m, 2H), 1.47-1.30 (m, 4H), 1.01 (s, 3H). MS: 686[M+H]⁺.

Example 27: Preparation of 1-(4-chloro-3-(trifluoromethyl)phenyl)-3-(4-((5-(3-((2-methoxyethyl)(methyl)amino)propoxy)-2,3-dihydro-[1,4]dioxino[2,3-f]quinolin-10-yl)oxy)phenyl)urea 2) Step 6: The product (1-(4-((5-(3-bromopropoxy)-2,3-dihydro-[1,4]dioxino[2,3-f]quinolin-10-yl)oxy)phenyl)-3-(4-chloro-3-(trifluoromethyl)phenylurea) (65 mg, 1 mmol) obtained in steps 1-5) was dissolved in acetonitrile (3 mL), to which triethylamine (202 mg, 2 mmol) and 2-methoxy-N-methylethan-1-amine (135 mg, 1.5 mmol) were then added. The mixture was reacted at 25° C. for 3 hours. The reaction solution was evaporated to dryness and subjected to column chromatography to afford 20 mg of a white solid. $^1$H NMR (600 MHz, DMSO-d$_6$) δ 9.31-9.23 (m, 1H), 9.05-8.96 (m, 1H), 8.43-8.35 (m, 1H), 8.15-8.07 (m, 1H), 7.69-7.57 (m, 2H), 7.57-7.49 (m, 2H), 7.12-7.04 (m, 2H), 7.04-6.99 (m, 1H), 6.46-6.37 (m, 1H), 4.38-4.27 (m, 4H), 4.20-4.08 (m, 2H), 3.43-3.39 (m, 2H), 3.30 (s, 3H), 3.21 (s, 3H), 2.55-2.52 (m, 2H), 2.25-2.21 (m, 2H), 1.99-1.86 (m, 2H). MS: 661[M+H]⁺.

Example 28: Preparation of 1-(4-chloro-3-(trifluoromethyl)phenyl)-3-(4-((5-(3-(cyclobutyl)(methyl)amino)propoxy)-2,3-dihydro-[1,4]dioxino[2,3-f]quinolin-10-yl)oxy)phenyl)urea The preparation was carried out in a similar manner to Example 27, except that an equimolar equivalent of N-methylcyclobutylamine was used in place of 2-methoxy-N-methylethan-1-amine in step 6) of Example 27. $^1$H NMR (600 MHz, DMSO-d$_6$) δ 10.04-9.79 (m, 1H), 9.74-9.52 (m,

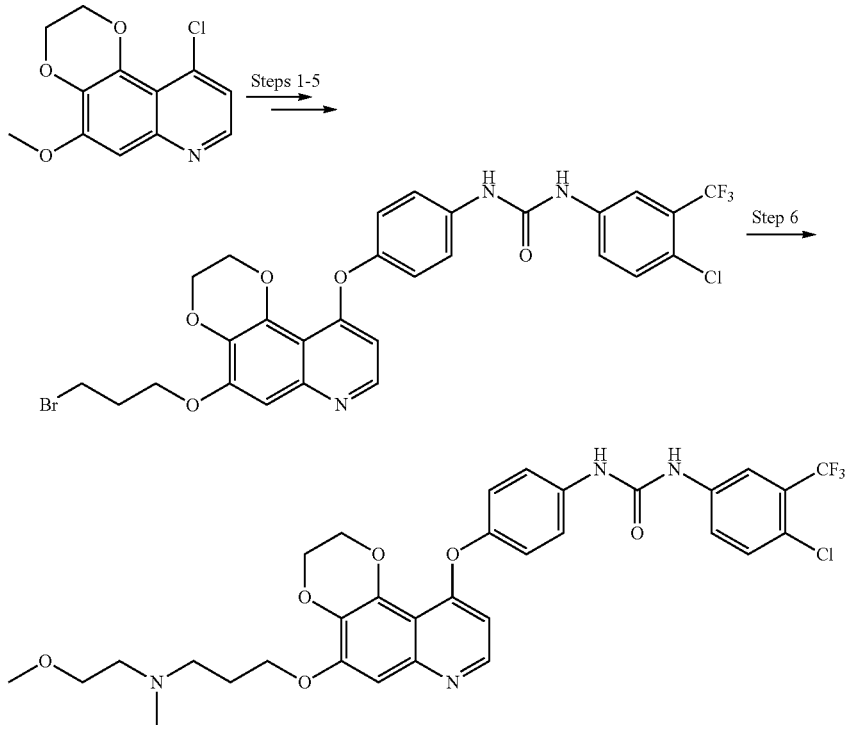

1) Steps 1-5): Preparation of 1-(4-((5-(3-bromopropoxy)-2,3-dihydro-[1,4]dioxino[2,3-f]quinolin-10-yl)oxy)phenyl)-3-(4-chloro-3-(trifluoromethyl)phenylurea The preparation was carried out in a similar manner to Example 8, except that an equimolar equivalent of 1,3-dibromopropane was used in place of 1-bromo-2-methoxyethane in step 2) of Example 8. MS: 652[M+H]⁺.

1H), 8.40 (d, J=5.2 Hz, 1H), 8.29 (d, J=16.4 Hz, 1H), 8.15 (d, J=2.7 Hz, 1H), 7.69 (dd, J=8.9, 3.0 Hz, 1H), 7.64-7.54 (m, 2H), 7.08 (d, J=8.4 Hz, 2H), 7.05 (s, 1H), 6.41 (d, J=5.2 Hz, 1H), 4.33 (s, 4H), 4.16 (t, J=6.5 Hz, 2H), 3.00-2.86 (m, 1H), 2.50-2.42 (m, 2H), 2.22-2.11 (m, 3H), 2.06-1.97 (m, 2H), 1.97-1.89 (m, 2H), 1.88-1.75 (m, 2H), 1.68-1.53 (m, 2H). MS: 657[M+H]⁺.

Example 28

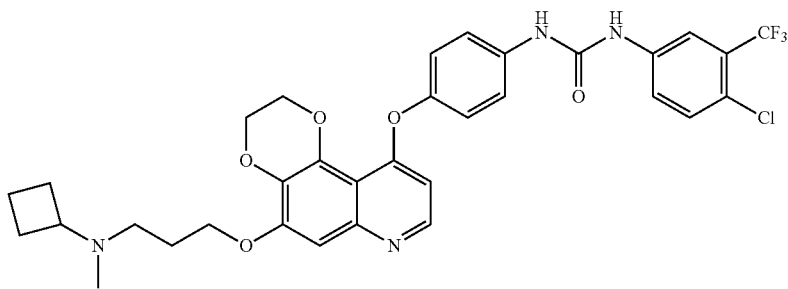

Example 29

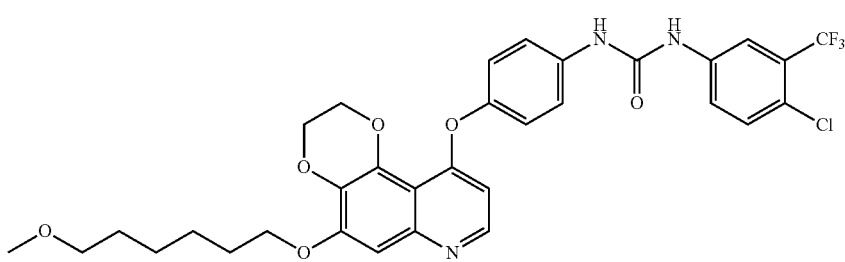

Example 29: Preparation of 1-(4-chloro-3-(trifluoromethyl)phenyl)-3-(4-((5-((6-methoxyhexyl)oxy)-2,3-dihydro-[1,4]dioxino[2,3-f]quinolin-10-yl)oxy)phenyl)urea The preparation was carried out in a similar manner to Example 8, except that an equimolar equivalent of 1-chloro-6-methoxyhexane was used in place of 1-bromo-2-methoxyethane in step 2) of Example 8. $^1$H NMR (600 MHz, DMSO-$d_6$) δ 9.20 (d, J=4.0 Hz, 1H), 8.95 (s, 1H), 8.45-8.38 (m, 1H), 8.12 (d, J=4.0 Hz, 1H), 7.69-7.58 (m, 2H), 7.58-7.50 (m, 2H), 7.13-7.05 (m, 2H), 7.04 (d, J=4.1 Hz, 1H), 6.45-6.38 (m, 1H), 4.37-4.29 (m, 4H), 4.14-4.08 (m, 2H), 3.22 (s, 3H), 2.57-2.53 (m, 2H), 1.84-1.72 (m, 2H), 1.57-1.50 (m, 2H), 1.50-1.42 (m, 2H), 1.42-1.31 (m, 2H). MS: 646[M+H]$^+$.

Example 30: Preparation of 1-(4-chloro-3-(trifluoromethyl)phenyl)-3-(4-((5-((6-(dimethylamino)hexyl)oxy)-2,3-dihydro-[1,4]dioxino[2,3-f]quinolin-10-yl)oxy)phenyl)urea The preparation was carried out in a similar manner to Example 8, except that an equimolar equivalent of 6-chloro-N,N-dimethylhexan-1-amine was used in place of 1-bromo-2-methoxyethane in step 2) of Example 8. $^1$H NMR (600 MHz, DMSO-$d_6$) δ 9.32 (d, J=6.1 Hz, 1H), 9.07 (d, J=6.1 Hz, 1H), 8.43-8.34 (m, 1H), 8.17-8.06 (m, 1H), 7.70-7.58 (m, 2H), 7.58-7.48 (m, 2H), 7.12-6.98 (m, 3H), 6.45-6.35 (m, 1H), 4.38-4.26 (m, 4H), 4.16-4.04 (m, 2H), 2.35-2.25 (m, 2H), 2.20 (s, 6H), 1.85-1.72 (m, 2H), 1.52-1.40 (m, 4H), 1.40-1.29 (m, 2H). MS: 659[M+H]$^+$.

Example 30

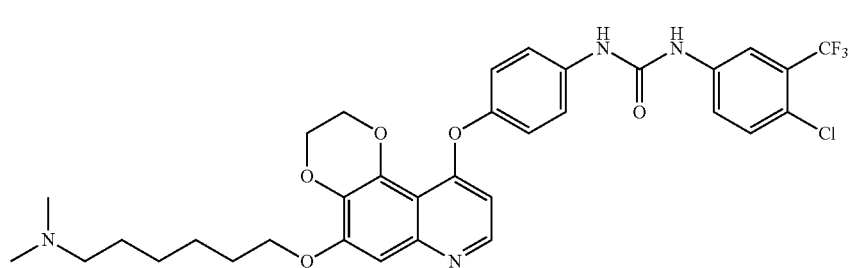

Example 31

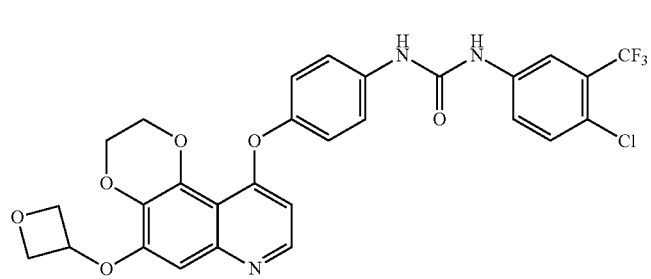

Example 31: Preparation of 1-(4-chloro-3-(trifluoromethyl)phenyl)-3-(4-((5-(oxetan-3-yl)oxy)-2,3-dihydro-[1,4]dioxino[2,3-f]quinolin-10-yl)oxy)phenyl)urea The preparation was carried out in a similar manner to Example 8, except that an equimolar equivalent of oxetan-3-yl 4-methylbenzenesulfonate was used in place of 1-bromo-2-methoxyethane in step 2) of Example 8. $^1$H NMR (400 MHz, DMSO-$d_6$) δ 9.21 (s, 1H), 8.97 (s, 1H), 8.41 (d, J=5.2 Hz, 1H), 8.12 (d, J=2.4 Hz, 1H), 7.72-7.59 (m, 2H), 7.59-7.49 (m, 2H), 7.14-7.04 (m, 2H), 6.68 (s, 1H), 6.44 (d, J=5.2 Hz, 1H), 5.52-5.39 (m, 1H), 5.08-4.96 (m, 2H), 4.68-4.58 (m, 2H), 4.44-4.30 (m, 4H). MS: 588[M+H]$^+$.

Example 32: Preparation of 1-(4-chloro-3-(trifluoromethyl)phenyl)-3-(4-((5-((tetrahydrofuran-3-yl)oxy)-2,3-dihydro-[1,4]dioxino[2,3-f]quinolin-10-yl)oxy)phenyl)urea The preparation was carried out in a similar manner to Example 8, except that an equimolar equivalent of tetrahydrofuran-3-yl 4-methylbenzenesulfonate was used in place of 1-bromo-2-methoxyethane in step 2) of Example 8. $^1$H NMR (400 MHz, DMSO-$d_6$) δ 9.19 (s, 1H), 8.95 (s, 1H), 8.41 (d, J=5.2 Hz, 1H), 8.12 (d, J=2.4 Hz, 1H), 7.69-7.58 (m, 2H), 7.58-7.51 (m, 2H), 7.12-7.06 (m, 2H), 7.02 (s, 1H), 6.43 (d, J=5.2 Hz, 1H), 5.24-5.16 (m, 1H), 4.38-4.28 (m, 4H), 4.01-3.93 (m, 1H), 3.93-3.83 (m, 2H), 3.83-3.73 (m, 1H), 2.39-2.27 (m, 1H), 2.13-2.00 (m, 1H). MS: 602[M+H]$^+$.

Example 32

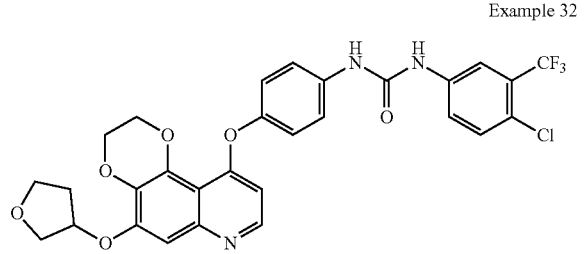

Example 33

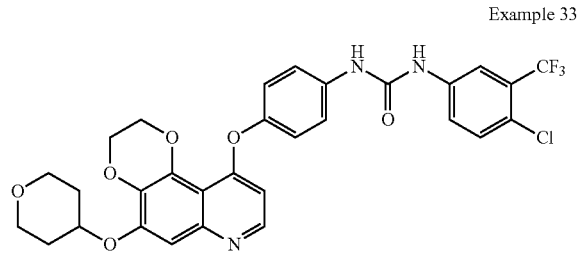

Example 33: Preparation of 1-(4-chloro-3-(trifluoromethyl)phenyl)-3-(4-((5-((tetrahydro-2H-pyran-4-yl)oxy)-2,3-dihydro-[1,4]dioxino[2,3-f]quinolin-10-yl)oxy)phenyl)urea The preparation was carried out in a similar manner to Example 8, except that an equimolar equivalent of tetrahydro-2H-pyran-4-yl 4-methylbenzenesulfonate was used in place of 1-bromo-2-methoxyethane in step 2) of Example 8. $^1$H NMR (400 MHz, DMSO-$d_6$) δ 9.20 (s, 1H), 8.95 (s, 1H), 8.41 (d, J=5.1 Hz, 1H), 8.12 (d, J=2.4 Hz, 1H), 7.70-7.58 (m, 2H), 7.58-7.50 (m, 2H), 7.16 (s, 1H), 7.11-7.05 (m, 2H), 6.42 (d, J=5.2 Hz, 1H), 4.85-4.74 (m, 1H), 4.38-4.27 (m, 4H), 3.95-3.84 (m, 2H), 3.63-3.49 (m, 2H), 2.14-2.00 (m, 2H), 1.74-1.58 (m, 2H). MS: 616[M+H]$^+$.

Example 34: Preparation of 1-(2-fluoro-5-(trifluoromethyl)phenyl)-3-(4-((5-(2-methoxyethoxy)-2,3-dihydro-[1,4]dioxino[2,3-f]quinolin-10-yl)oxy)phenyl)urea The preparation was carried out in a similar manner to Example 8, except that an equimolar equivalent of 2-fluoro-5-(trifluoromethyl)aniline was used in place of 4-chloro-3-(trifluoromethyl)aniline in step 5) of Example 8. $^1$H NMR (400 MHz, DMSO-$d_6$) δ 9.33 (s, 1H), 8.96 (d, J=2.9 Hz, 1H), 8.62 (dd, J=7.3, 2.3 Hz, 1H), 8.41 (d, J=5.2 Hz, 1H), 7.60-7.45 (m, 3H), 7.44-7.35 (m, 1H), 7.15-7.03 (m, 3H), 6.43 (d, J=5.2 Hz, 1H), 4.39-4.29 (m, 4H), 4.29-4.20 (m, 2H), 3.78-3.70 (m, 2H), 3.30 (s, 3H). MS: 574[M+H]$^+$.

Example 34

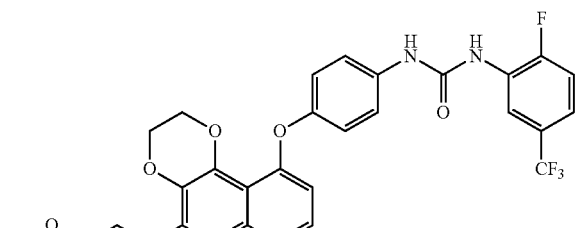

Example 35

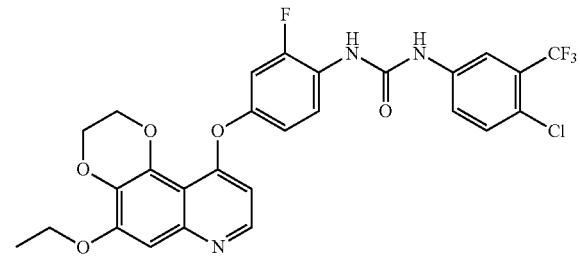

Example 35: Preparation of 1-(4-chloro-3-(trifluoromethyl)phenyl)-3-(4-((5-ethoxy-2,3-dihydro-[1,4]dioxino[2,3-f]quinolin-10-yl)oxy)-2-fluorophenyl)urea The preparation was carried out in a similar manner to Example 8, except that an equimolar equivalent of iodoethane was used in place of 1-bromo-2-methoxyethane in step 2) of Example 8, and an equimolar equivalent of 3-fluoro-4-nitrophenol was used in place of p-nitrophenol in step 3) of Example 8. $^1$H NMR (400 MHz, DMSO-$d_6$) δ 9.52 (s, 1H), 8.69 (d, J=2.1 Hz, 1H), 8.46 (d, J=5.1 Hz, 1H), 8.12 (d, J=1.8 Hz, 1H), 8.09-8.00 (m, 1H), 7.62 (d, J=1.6 Hz, 2H), 7.16 (dd, J=11.8, 2.7 Hz, 1H), 7.06 (s, 1H), 6.95-6.88 (m, 1H), 6.57 (d, J=5.1 Hz, 1H), 4.38-4.24 (m, 4H), 4.18 (q, J=6.9 Hz, 2H), 1.41 (t, J=6.9 Hz, 3H). MS: 578 [M+H]$^+$.

Example 36: Preparation of 1-(4-chloro-3-(trifluoromethyl)phenyl)-3-(3-fluoro-4-((5-(2-methoxyethoxy)-2,3-dihydro-[1,4]dioxino[2,3-f]quinolin-10-yl)oxy)phenyl)urea The preparation was carried out in a similar manner to Example 8, except that an equimolar equivalent of 2-fluoro- 4-nitrophenol was used in place of p-nitrophenol in step 3) of Example 8. ¹HNMR (300 MHz, DMSO-d₆) δ 9.33 (s, 1H), 9.22 (s, 1H), 8.42 (d, J=4.8 Hz, 1H), 8.11 (d, J=2.0 Hz, 1H), 7.77-7.52 (m, 3H), 7.25 (d, J=2.5 Hz, 2H), 7.12-7.04 (m, 1H), 6.47-6.35 (m, 1H), 4.47-4.32 (m, 4H), 4.30-4.19 (m, 2H), 3.80-3.69 (m, 2H), 3.35 (s, 3H); MS: 608[M+H]⁺.

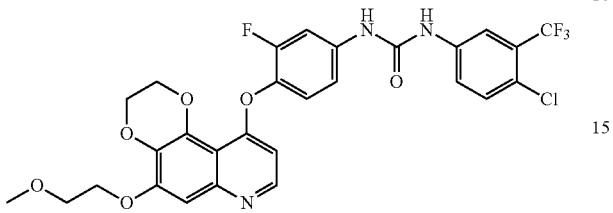

Example 36

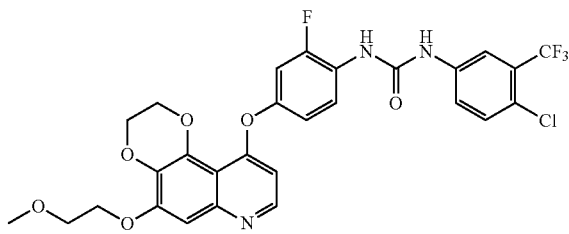

Example 37

Example 37: Preparation of 1-(4-chloro-3-(trifluoromethyl)phenyl)-3-(2-fluoro-4-((5-(2-methoxyethoxy)-2,3-dihydro-[1,4]dioxino[2,3-f]quinolin-10-yl)oxy)phenyl)urea The preparation was carried out in a similar manner to Example 8, except that an equimolar equivalent of 3-fluoro-4-nitrophenol was used in place of p-nitrophenol in step 3) of Example 8. ¹H NMR (400 MHz, DMSO-d₆) δ 9.61 (s, 1H), 8.72 (s, 1H), 8.47 (d, J=5.2 Hz, 1H), 8.14 (d, J=11.9 Hz, 1H), 8.10-8.01 (m, 1H), 7.62 (s, 2H), 7.17 (dd, J=11.8, 2.7 Hz, 1H), 7.09 (s, 1H), 6.92 (d, J=9.1 Hz, 1H), 6.57 (d, J=5.2 Hz, 1H), 4.40-4.19 (m, 6H), 3.74 (t, J=4.3 Hz, 2H), 3.34 (s, 3H). MS: 608[M+H]⁺.

Example 38: Preparation of 1-(4-chloro-3-(trifluoromethyl)phenyl)-3-(3-fluoro-4-((5-(3-methoxypropoxy)-2,3-dihydro-[1,4]dioxino[2,3-f]quinolin-10-yl)oxy)phenyl)urea The preparation was carried out in a similar manner to Example 8, except that an equimolar equivalent of 1-bromo-3-methoxypropane was used in place of 1-bromo-2-methoxyethane in step 2) of Example 8, and an equimolar equivalent of 2-fluoro-4-nitrophenol was used in place of p-nitrophenol in step 3) of Example 8. ¹H NMR (400 MHz, DMSO-d₆) δ 9.37 (s, 1H), 9.26 (s, 1H), 8.41 (d, J=5.2 Hz, 1H), 8.11 (d, J=2.5 Hz, 1H), 7.75-7.59 (m, 3H), 7.30-7.22 (m, 2H), 7.05 (s, 1H), 6.41 (dd, J=5.2, 1.1 Hz, 1H), 4.42-4.31 (m, 4H), 4.18 (t, J=6.4 Hz, 2H), 3.52 (t, J=6.3 Hz, 2H), 3.27 (s, 3H), 2.11-1.96 (m, 2H). MS: 622[M+H]⁺.

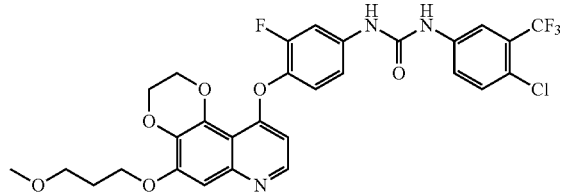

Example 38

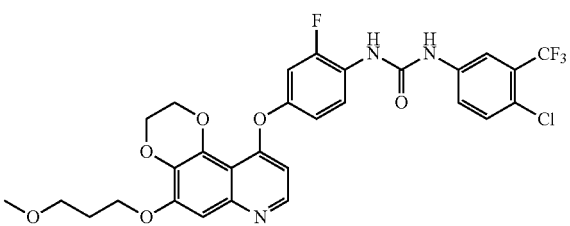

Example 39

Example 39: Preparation of 1-(4-chloro-3-(trifluoromethyl)phenyl)-3-(2-fluoro-4-((5-(3-methoxypropoxy)-2,3-dihydro-[1,4]dioxino[2,3-f]quinolin-10-yl)oxy)phenyl)urea The preparation was carried out in a similar manner to Example 8, except that an equimolar equivalent of 1-bromo-3-methoxypropane was used in place of 1-bromo-2-methoxyethane in step 2) of Example 8, and an equimolar equivalent of 3-fluoro-4-nitrophenol was used in place of p-nitrophenol in step 3) of Example 8. ¹H NMR (600 MHz, DMSO-d₆) δ 9.69 (s, 1H), 8.84 (s, 1H), 8.47 (d, J=5.1 Hz, 1H), 8.13 (d, J=1.9 Hz, 1H), 8.08-8.00 (m, 1H), 7.63 (d, J=2.2 Hz, 2H), 7.15 (dd, J=11.8, 2.7 Hz, 1H), 7.07 (s, 1H), 6.95-6.87 (m, 1H), 6.58 (d, J=5.1 Hz, 1H), 4.37-4.25 (m, 4H), 4.18 (t, J=6.4 Hz, 2H), 3.51 (t, J=6.3 Hz, 2H), 3.27 (s, 3H), 2.08-1.97 (m, 2H). MS: 622 [M+H]⁺.

Example 40: Preparation of 1-(2-fluoro-5-(trifluoromethyl)phenyl)-3-(4-((5-(3-methoxypropoxy)-2,3-dihydro-[1,4]dioxino[2,3-f]quinolin-10-yl)oxy)phenyl)urea The preparation was carried out in a similar manner to Example 8, except that an equimolar equivalent of 1-bromo-3-methoxypropane was used in place of 1-bromo-2-methoxyethane in step 2) of Example 8, and an equimolar equivalent of 2-fluoro-5-(trifluoromethyl)aniline was used in place of 4-chloro-3-(trifluoromethyl)aniline in step 5) of Example 8. ¹H NMR (400 MHz, DMSO-d₆) δ 9.26 (s, 1H), 8.90 (d, J=2.9 Hz, 1H), 8.62 (dd, J=7.3, 2.4 Hz, 1H), 8.41 (d, J=5.2 Hz, 1H), 7.62-7.44 (m, 3H), 7.44-7.33 (m, 1H), 7.14-7.06 (m, 2H), 7.04 (s, 1H), 6.43 (d, J=5.2 Hz, 1H), 4.40-4.27 (m, 4H), 4.17 (t, J=6.4 Hz, 2H), 3.51 (t, J=6.3 Hz, 2H), 3.27 (s, 3H), 2.10-1.99 (m, 2H). MS: 588[M+H]⁺.

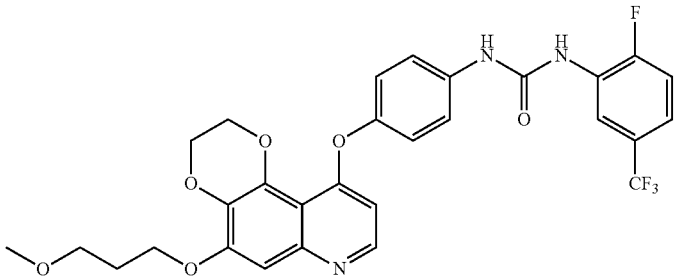

Example 40

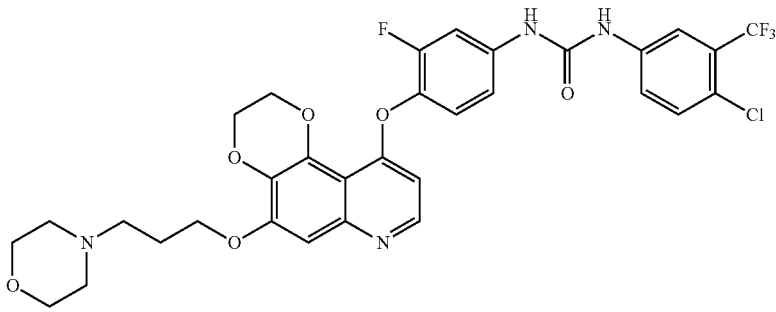

Example 41

Example 41: Preparation of 1-(4-chloro-3-(trifluoromethyl)phenyl)-3-(3-fluoro-4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8, and an equimolar equivalent of 2-fluoro-4-nitrophenol was used in place of p-nitrophenol in step 3) of Example 8. $^1$H NMR (400 MHz, DMSO-d$_6$) δ 9.30 (s, 1H), 9.20 (s, 1H), 8.41 (d, J=5.3 Hz, 1H), 8.17-8.07 (m, 1H), 7.76-7.58 (m, 3H), 7.29-7.21 (m, 2H), 7.07 (s, 1H), 6.41 (dd, J=5.2, 1.0 Hz, 1H), 4.40-4.33 (m, 4H), 4.19 (t, J=6.3 Hz, 2H), 3.68-3.58 (m, 4H), 3.34-3.32 (m, 4H), 2.63-2.53 (m, 2H), 2.07-1.95 (m, 2H). MS: 677[M+H]$^+$.

Example 42: Preparation of 1-(4-chloro-3-(trifluoromethyl)phenyl)-3-(2-fluoro-4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8, and an equimolar equivalent of 3-fluoro-4-nitrophenol was used in place of p-nitrophenol in step 3) of Example 8. $^1$H NMR (400 MHz, DMSO-d$_6$) δ 9.49 (s, 1H), 8.67 (d, J=2.2 Hz, 1H), 8.48 (d, J=5.2 Hz, 1H), 8.16-8.10 (m, 1H), 8.10-8.02 (m, 1H), 7.66-7.57 (m, 2H), 7.16 (dd, J=11.8, 2.7 Hz, 1H), 7.10 (s, 1H), 6.94-6.87 (m, 1H), 6.59 (d, J=5.2 Hz, 1H), 4.37-4.26 (m, 4H), 4.21 (t, J=6.2 Hz, 2H), 3.84-3.52 (m, 4H), 3.12-2.51 (m, 6H), 2.20-1.98 (m, 2H). MS: 677 [M+H]$^+$.

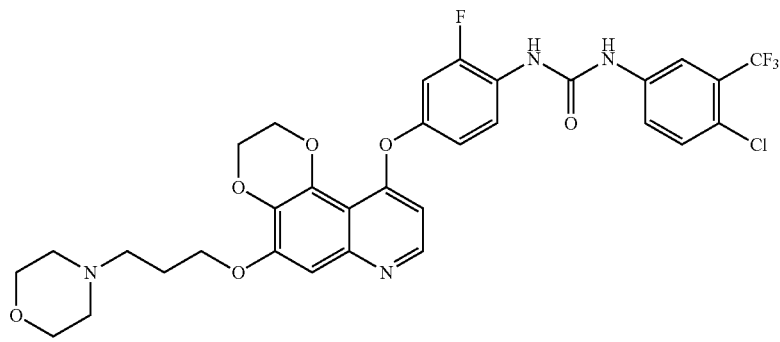

Example 42

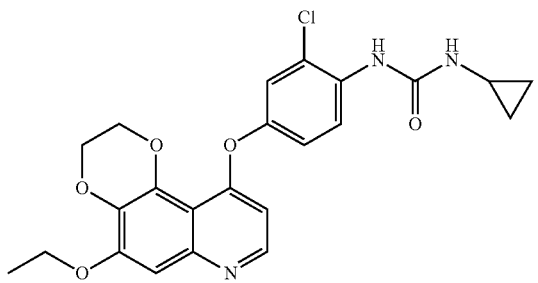

Example 43: Preparation of 1-(2-chloro-4-((5-ethoxy-2,3-dihydro-[1,4]dioxino[2,3-f]quinolin-10-yl)oxy)phenyl)-3-cyclopropylurea The preparation was carried out in a similar manner to Example 8, except that an equimolar equivalent of iodoethane was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.44 (d, J=5.2 Hz, 1H), 8.17 (d, J=9.1 Hz, 1H), 7.90 (s, 1H), 7.25 (d, J=2.8 Hz, 1H), 7.14 (d, J=2.9 Hz, 1H), 7.09-7.01 (m, 2H), 6.50 (d, J=5.2 Hz, 1H), 4.38-4.26 (m, 4H), 4.18 (q, J=7.0 Hz, 2H), 2.59-2.53 (m, 1H), 1.41 (t, J=7.0 Hz, 3H), 0.70-0.60 (m, 2H), 0.44-0.37 (m, 2H). MS: 456[M+H]$^+$.

Example 44: Preparation of 1-(2-chloro-4-((5-isopropoxy-2,3-dihydro-[1,4]dioxino[2,3-f]quinolin-10-yl)oxy)phenyl)-3-cyclopropylurea The preparation was carried out in a similar manner to Example 8, except that an equimolar equivalent of isopropyl bromide was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.43 (d, J=5.1 Hz, 1H), 8.17 (d, J=9.0 Hz, 1H), 7.90 (s, 1H), 7.24 (d, J=2.8 Hz, 1H), 7.13 (d, J=3.0 Hz, 1H), 7.09-7.00 (m, 2H), 6.50 (d, J=5.2 Hz, 1H), 4.81 (p, J=6.0 Hz, 1H), 4.36-4.24 (m, 4H), 2.60-2.52 (m, 1H), 1.36 (d, J=6.0 Hz, 6H), 0.71-0.60 (m, 2H), 0.46-0.36 (m, 2H). MS: 470 [M+H]$^+$.

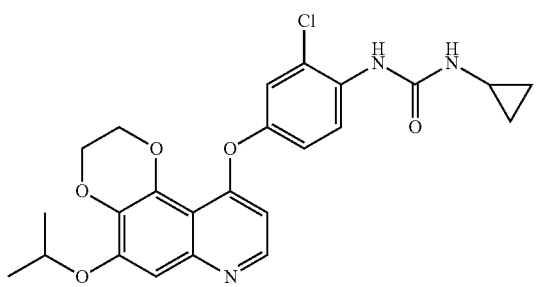

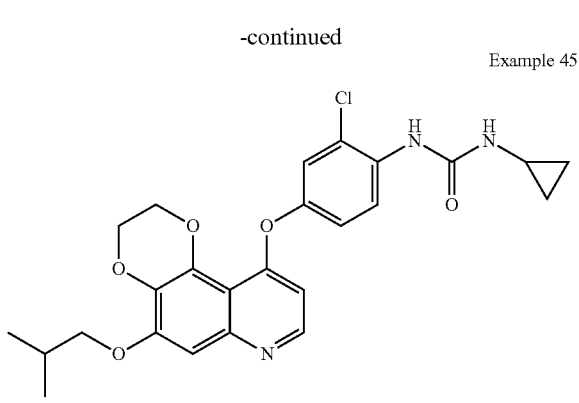

Example 45: Preparation of 1-(2-chloro-4-((5-isobutoxy-2,3-dihydro-[1,4]dioxino[2,3-f]quinolin-10-yl)oxy)phenyl)-3-cyclopropylurea The preparation was carried out in a similar manner to Example 8, except that an equimolar equivalent of isobutyl bromide was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.44 (d, J=5.2 Hz, 1H), 8.17 (d, J=9.0 Hz, 1H), 7.90 (s, 1H), 7.24 (d, J=2.8 Hz, 1H), 7.13 (d, J=2.9 Hz, 1H), 7.07-7.01 (m, 2H), 6.51 (d, J=5.2 Hz, 1H), 4.36-4.26 (m, 4H), 3.90 (d, J=6.6 Hz, 2H), 2.57-2.55 (m, 1H), 2.16-2.05 (m, 1H), 1.03 (d, J=6.7 Hz, 6H), 0.69-0.63 (m, 2H), 0.46-0.38 (m, 2H). MS: 484[M+H]$^+$.

Example 46: Preparation of 1-(2-chloro-4-((5-(cyclopropylmethoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of bromomethylcyclopropane was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (400 MHz, DMSO-d$_6$) δ 8.44 (d, J=5.1 Hz, 1H), 8.17 (d, J=9.1 Hz, 1H), 7.89 (s, 1H), 7.24 (d, J=2.7 Hz, 1H), 7.13 (d, J=2.9 Hz, 1H), 7.09-6.98 (m, 2H), 6.51 (d, J=5.1 Hz, 1H), 4.39-4.24 (m, 4H), 3.97 (d, J=7.0 Hz, 2H), 2.62-2.54 (m, 1H), 1.38-1.20 (m, 1H), 0.73-0.57 (m, 4H), 0.48-0.33 (m, 4H). MS: 482[M+H]$^+$.

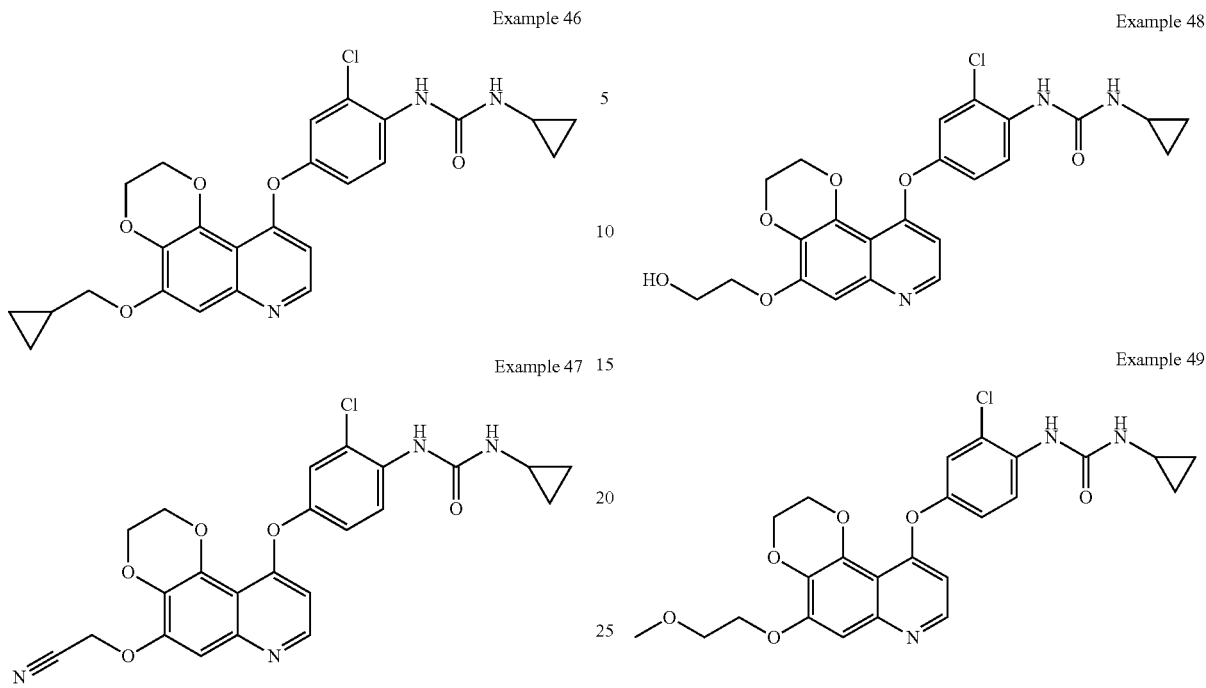

Example 46

Example 48

Example 47

Example 49

Example 47: Preparation of 1-(2-chloro-4-((5-(cyanomethoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of bromoacetonitrile was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.50 (dd, J=5.2, 1.8 Hz, 1H), 8.19 (dd, J=9.0, 1.8 Hz, 1H), 7.92 (d, J=1.8 Hz, 1H), 7.31-7.24 (m, 2H), 7.15 (d, J=2.9 Hz, 1H), 7.10-7.05 (m, 1H), 6.57 (dd, J=5.2, 1.8 Hz, 1H), 5.37 (s, 2H), 4.40-4.31 (m, 4H), 2.58-2.55 (m, 1H), 0.70-0.62 (m, 2H), 0.47-0.37 (m, 2H). MS: 467[M+H]$^+$.

Example 48: Preparation of 1-(2-chloro-4-((5-(2-hydroxyethoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 2-bromoethan-1-ol was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.44 (d, J=5.1 Hz, 1H), 8.17 (d, J=9.1 Hz, 1H), 7.90 (s, 1H), 7.25 (d, J=2.8 Hz, 1H), 7.13 (d, J=2.9 Hz, 1H), 7.10-7.02 (m, 2H), 6.51 (d, J=5.1 Hz, 1H), 4.94 (t, J=5.4 Hz, 1H), 4.37-4.27 (m, 4H), 4.14 (t, J=4.9 Hz, 2H), 3.83-3.76 (m, 2H), 2.60-2.53 (m, 1H), 0.68-0.61 (m, 2H), 0.44-0.38 (m, 2H). MS: 472[M+H]$^+$.

Example 49: Preparation of 1-(2-chloro-4-((5-(2-methoxyethoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.44 (d, J=5.2 Hz, 1H), 8.18 (d, J=9.0 Hz, 1H), 7.90 (s, 1H), 7.25 (d, J=2.8 Hz, 1H), 7.14 (d, J=2.9 Hz, 1H), 7.10-7.02 (m, 2H), 6.51 (d, J=5.2 Hz, 1H), 4.38-4.27 (m, 4H), 4.27-4.20 (m, 2H), 3.77-3.67 (m, 2H), 3.34 (s, 3H), 2.61-2.53 (m, 1H), 0.79-0.55 (m, 2H), 0.52-0.28 (m, 2H). MS: 486[M+H]$^+$.

Example 50: Preparation of 1-(2-chloro-4-((5-(3-hydroxypropoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 3-bromopropan-1-ol was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.44 (d, J=5.2 Hz, 1H), 8.17 (d, J=9.1 Hz, 1H), 7.90 (s, 1H), 7.24 (d, J=2.8 Hz, 1H), 7.13 (d, J=2.9 Hz, 1H), 7.08-7.02 (m, 2H), 6.51 (d, J=5.2 Hz, 1H), 4.63-4.57 (m, 1H), 4.35-4.27 (m, 4H), 4.19 (t, J=6.4 Hz, 2H), 3.64-3.57 (m, 2H), 2.59-2.54 (m, 1H), 1.94 (t, J=6.3 Hz, 2H), 0.69-0.62 (m, 2H), 0.45-0.38 (m, 2H). MS: 486[M+H]$^+$.

Example 50

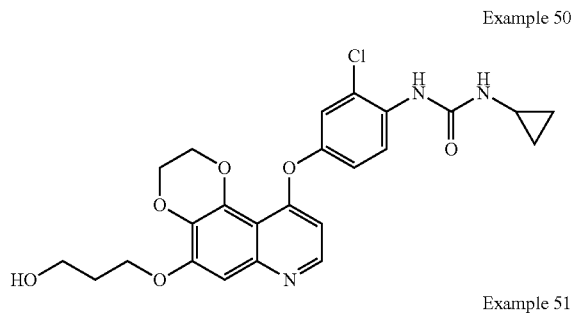

Example 51

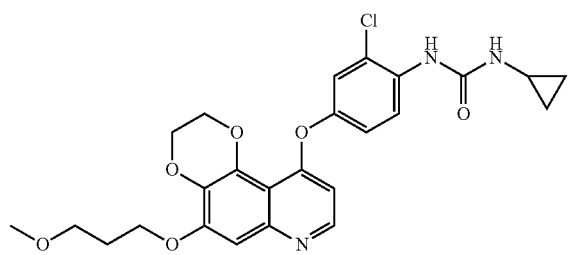

Example 52

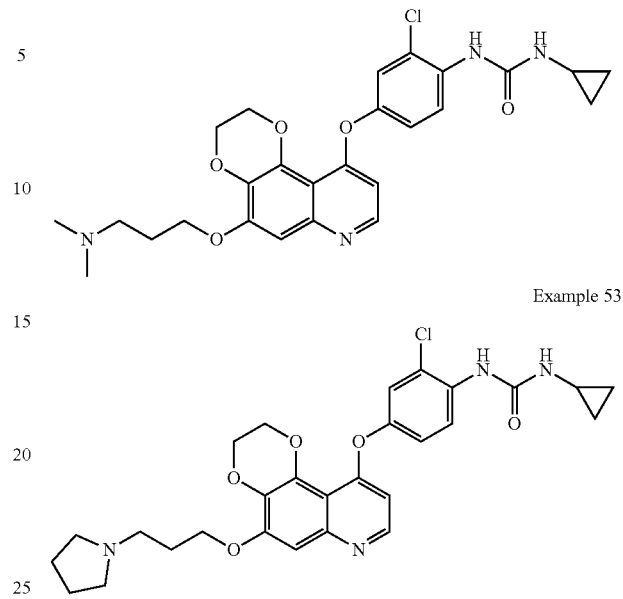

Example 51: Preparation of 1-(2-chloro-4-((5-(3-methoxypropoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 1-bromo-3-methoxypropane was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (400 MHz, DMSO-$d_6$) δ 8.44 (d, J=5.1 Hz, 1H), 8.17 (d, J=9.1 Hz, 1H), 7.90 (s, 1H), 7.25 (d, J=2.8 Hz, 1H), 7.14 (d, J=2.9 Hz, 1H), 7.08-7.01 (m, 2H), 6.51 (d, J=5.2 Hz, 1H), 4.37-4.25 (m, 4H), 4.17 (t, J=6.4 Hz, 2H), 3.51 (t, J=6.3 Hz, 2H), 3.27 (s, 3H), 2.59-2.54 (m, 1H), 2.09-2.01 (m, 2H), 0.71-0.58 (m, 2H), 0.47-0.37 (m, 2H). MS: 500[M+H]$^+$.

Example 52: Preparation of 1-(2-chloro-4-((5-(3-(dimethylamino)propoxy)-2,3-dihydro-[1,4]dioxino[2,3-f]quinolin-10-yl) oxy)phenyl)-3-cyclopropylurea The preparation was carried out in a similar manner to Example 8, except that an equimolar equivalent of 3-chloro-N,N-dimethylpropan-1-amine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.44 (d, J=5.1 Hz, 1H), 8.17 (d, J=9.0 Hz, 1H), 7.90 (s, 1H), 7.24 (d, J=2.8 Hz, 1H), 7.13 (d, J=2.9 Hz, 1H), 7.07-7.02 (m, 2H), 6.51 (d, J=5.1 Hz, 1H), 4.36-4.27 (m, 4H), 4.15 (t, J=6.5 Hz, 2H), 2.57-2.55 (m, 1H), 2.40 (t, J=7.1 Hz, 2H), 2.17 (s, 6H), 1.96-1.89 (m, 2H), 0.70-0.62 (m, 2H), 0.49-0.39 (m, 2H). MS: 513[M+H]$^+$.

Example 53: Preparation of 1-(2-chloro-4-((5-(3-(pyrrolidin-1-yl)propoxy)-2,3-dihydro-[1,4]dioxino[2,3-f]quinolin-10-yl) oxy)phenyl)-3-cyclopropylurea The preparation was carried out in a similar manner to Example 8, except that an equimolar equivalent of 1-(3-chloropropyl)pyrrolidine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.40-8.34 (m, 1H), 8.10 (d, J=9.1 Hz, 1H), 7.84 (s, 1H), 7.20-7.15 (m, 1H), 7.07 (d, J=2.9 Hz, 1H), 7.02-6.94 (m, 2H), 6.44 (d, J=5.2 Hz, 1H), 4.33-4.19 (m, 4H), 4.10 (t, J=6.5 Hz, 2H), 2.56-2.48 (m, 5H), 1.98-1.85 (m, 3H), 1.71-1.57 (m, 5H), 0.64-0.54 (m, 2H), 0.41-0.31 (m, 2H). MS: 539[M+H]$^+$.

Example 54: Preparation of 1-(2-chloro-4-((5-(3-(piperidin-1-yl)propoxy)-2,3-dihydro-[1,4]dioxino[2,3-f]quinolin-10-yl) oxy)phenyl)-3-cyclopropylurea The preparation was carried out in a similar manner to Example 8, except that an equimolar equivalent of 1-(3-chloropropyl)piperidine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-$d_6$) δ 8.48-8.41 (m, 1H), 8.22-8.13 (m, 1H), 7.94-7.87 (m, 1H), 7.27-7.21 (m, 1H), 7.17-7.11 (m, 1H), 7.08-7.01 (m, 2H), 6.54-6.47 (m, 1H), 4.36-4.26 (m, 4H), 4.19-4.10 (m, 2H), 2.58-2.55 (m, 1H), 2.47-2.29 (m, 6H), 1.99-1.91 (m, 2H), 1.55-1.47 (m, 4H), 1.43-1.35 (m, 2H), 0.70-0.61 (m, 2H), 0.46-0.36 (m, 2H). MS: 553[M+H]$^+$.

Example 54

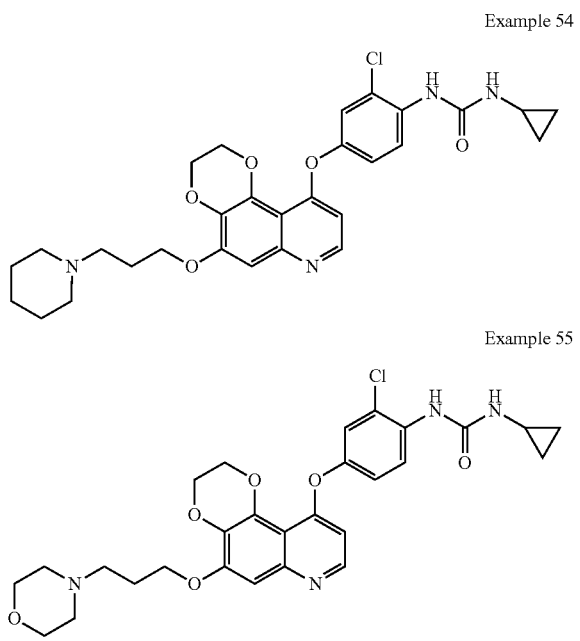

Example 56

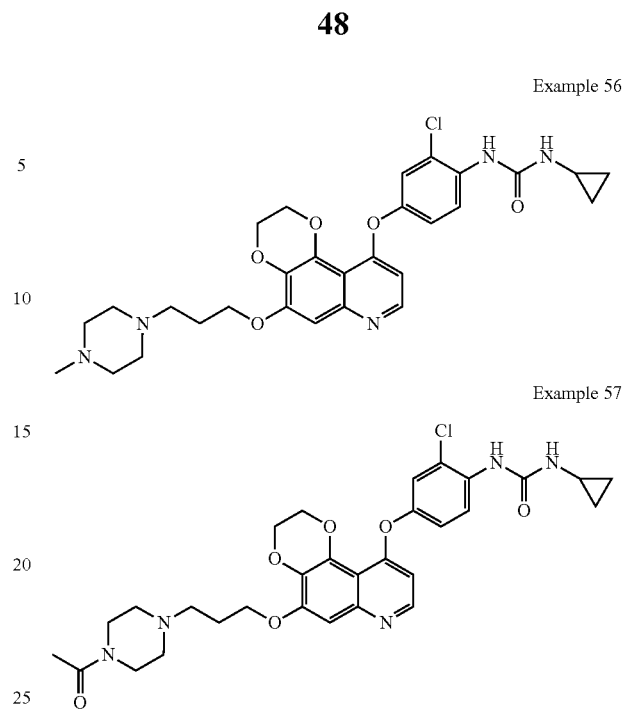

Example 55

Example 57

Example 55: Preparation of 1-(2-chloro-4-((5-(3-morpholinopropoxy)-2,3-dihydro-[1,4]dioxino[2,3-f]quinolin-10-yl)oxy) phenyl)-3-cyclopropylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.38 (dd, J=8.8, 5.2 Hz, 1H), 8.14-8.07 (m, 1H), 7.84 (d, J=7.7 Hz, 1H), 7.21-7.15 (m, 1H), 7.11-7.04 (m, 1H), 7.02-6.94 (m, 2H), 6.45 (dd, J=8.8, 5.3 Hz, 1H), 4.30-4.18 (m, 4H), 4.15-4.05 (m, 2H), 3.56-3.49 (m, 4H), 2.53-2.48 (m, 1H), 2.39 (t, J=7.3 Hz, 2H), 2.36-2.25 (m, 4H), 1.96-1.85 (m, 2H), 0.63-0.54 (m, 2H), 0.42-0.31 (m, 2H). MS: 555 [M+H]$^+$.

Example 56: Preparation of 1-(2-chloro-4-((5-(3-(4-methylpiperazin-1-yl)propoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 1-(3-chloropropyl)-4-methylpiperazine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.49-8.39 (m, 1H), 8.17 (dd, J=9.1, 3.1 Hz, 1H), 7.91 (d, J=3.0 Hz, 1H), 7.24 (d, J=3.5 Hz, 1H), 7.15 (s, 1H), 7.08-7.00 (m, 2H), 6.57-6.47 (m, 1H), 4.39-4.24 (m, 4H), 4.21-4.09 (m, 2H), 2.58-2.55 (m, 1H), 2.50-2.32 (m, 10H), 2.22 (s, 3H), 2.01-1.88 (m, 2H), 0.71-0.61 (m, 2H), 0.49-0.36 (m, 2H). MS: 568[M+H]$^+$.

Example 57: Preparation of 1-(4-((5-(3-(4-acetylpiperazin-1-yl)propoxy)-2,3-dihydro-[1,4]dioxino[2,3-f]quinolin-10-yl)oxy)-2-chlorophenyl)-3-cyclopropylurea The preparation was carried out in a similar manner to Example 8, except that an equimolar equivalent of 1-(4-(3-chloropropyl)piperazin-1-yl)ethan-1-one hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (400 MHz, DMSO-d$_6$) δ 8.44 (d, J=5.1 Hz, 1H), 8.17 (d, J=9.1 Hz, 1H), 7.90 (s, 1H), 7.24 (d, J=2.8 Hz, 1H), 7.14 (d, J=2.9 Hz, 1H), 7.09-7.01 (m, 2H), 6.51 (d, J=5.1 Hz, 1H), 4.37-4.26 (m, 4H), 4.17 (t, J=6.4 Hz, 2H), 3.48-3.39 (m, 4H), 2.58-2.53 (m, 1H), 2.49-2.45 (m, 2H), 2.40 (t, J=5.0 Hz, 2H), 2.33 (t, J=5.1 Hz, 2H), 2.02-1.93 (m, 5H), 0.70-0.60 (m, 2H), 0.46-0.36 (m, 2H). MS: 596[M+H]$^+$.

Example 58: Preparation of 1-(2-chloro-4-((5-(3-(1,1-dioxothiomorpholino)propoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 4-(3-chloropropyl)thiomorpholine-1,1-dioxide hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.44 (d, J=5.1 Hz, 1H), 8.17 (d, J=9.0 Hz, 1H), 7.90 (s, 1H), 7.24 (d, J=2.6 Hz, 1H), 7.14 (d, J=2.9 Hz, 1H), 7.09 (s, 1H), 7.05 (dd, J=9.1, 2.7 Hz, 1H), 6.51 (d, J=5.1 Hz, 1H), 4.36-4.26 (m, 4H), 4.18 (t, J=6.5 Hz, 2H), 3.14-3.06 (m, 4H), 2.96-2.87 (m, 4H), 2.65 (t, J=7.0 Hz, 2H), 2.58-2.55 (m, 1H), 1.99-1.92 (m, 2H), 0.69-0.62 (m, 2H), 0.47-0.37 (m, 2H). MS: 603[M+H]$^+$.

Example 58

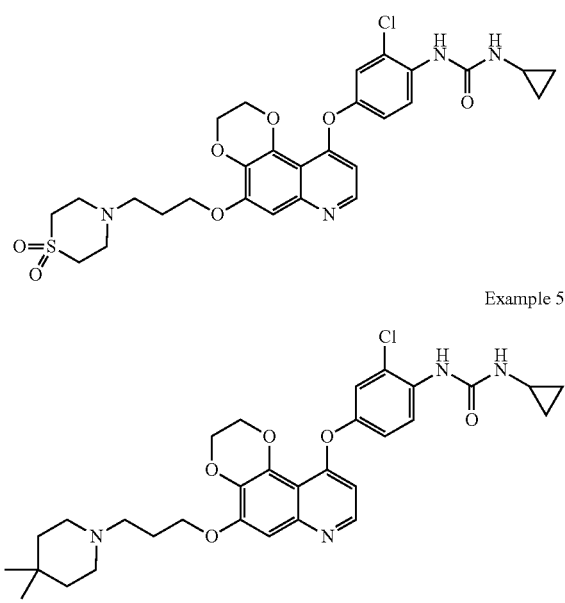

Example 59

Example 59: Preparation of 1-(2-chloro-4-((5-(3-(4,4-dimethylpiperidin-1-yl)propoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 1-(3-chloropropyl)-4,4-dimethylpiperidine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.49-8.40 (m, 1H), 8.17 (dd, J=9.0, 5.8 Hz, 1H), 7.90 (d, J=5.5 Hz, 1H), 7.27-7.21 (m, 1H), 7.17-7.11 (m, 1H), 7.05 (dd, J=6.1, 3.6 Hz, 2H), 6.56-6.47 (m, 1H), 4.37-4.26 (m, 4H), 4.19-4.11 (m, 2H), 2.59-2.53 (m, 1H), 2.48-2.44 (m, 2H), 2.40-2.31 (m, 4H), 2.00-1.90 (m, 2H), 1.38-1.29 (m, 4H), 0.90 (s, 6H), 0.69-0.61 (m, 2H), 0.45-0.37 (m, 2H). MS: 581[M+H]$^+$.

Example 60: Preparation of 1-(2-chloro-4-((5-(3-(4-hydroxy-4-methylpiperidin-1-yl)propoxy)-2,3-dihydro-[1,4]dioxino[2,3-f]quinolin-10-yl)oxy)phenyl)-3-cyclopropylurea

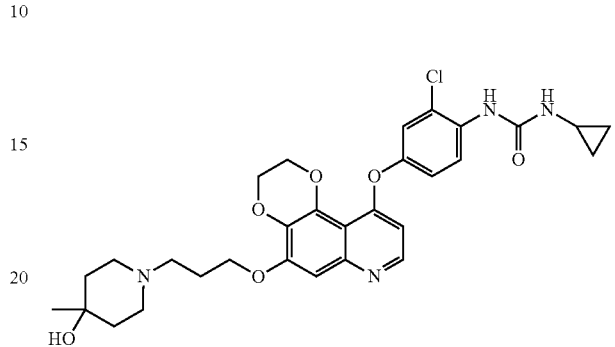

The preparation was carried out in a similar manner to Example 8, except that an equimolar equivalent of 1-(3-chloropropyl)-4-methylpiperidin-4-ol was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (600 MHz, DMSO-d$_6$) δ 8.56 (d, J=5.8 Hz, 1H), 8.24 (d, J=9.0 Hz, 1H), 8.00 (s, 1H), 7.47 (d, J=7.6 Hz, 1H), 7.36 (s, 1H), 7.26 (s, 2H), 6.64 (d, J=5.6 Hz, 1H), 4.45-4.32 (m, 4H), 4.26 (t, J=5.9 Hz, 2H), 3.27-3.24 (m, 2H), 3.18-3.04 (m, 4H), 2.59-2.55 (m, 1H), 2.33-2.26 (m, 2H), 1.90-1.78 (m, 2H), 1.74-1.62 (m, 2H), 1.27-1.23 (m, 1H), 1.19 (s, 3H), 0.72-0.61 (m, 2H), 0.47-0.37 (m, 2H). MS: 583[M+H]$^+$.

Example 61: Preparation of 1-(4-((5-(3-(4-amino-4-methylpiperidin-1-yl)propoxy)-2,3-dihydro-[1,4]dioxino[2,3-f]quinolin-10-yl)oxy)-2-chlorophenyl)-3-cyclopropylurea

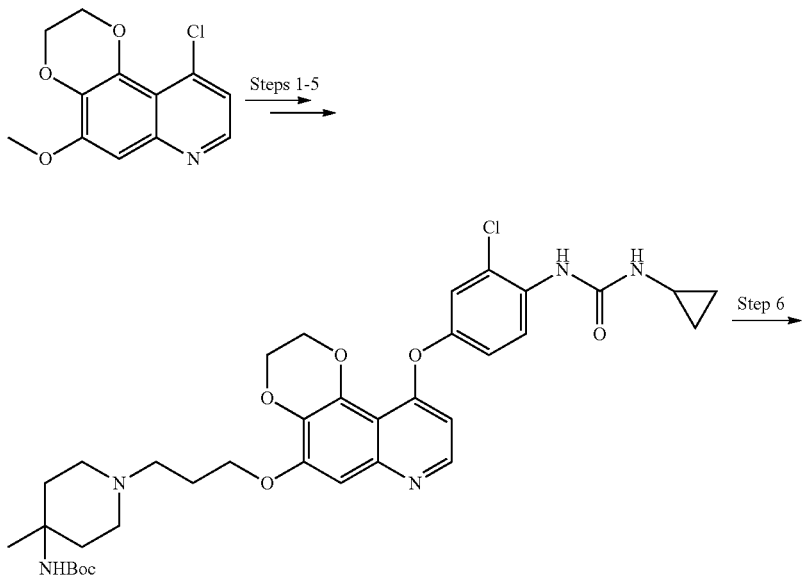

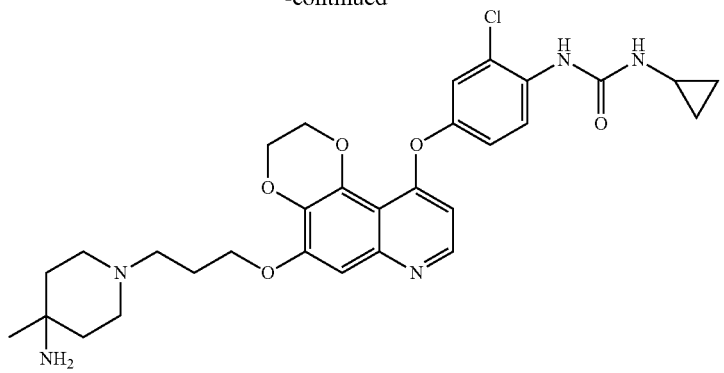

1) Steps 1-5): Preparation of tert-butyl (1-(3-((10-(3-chloro-4-(3-cyclopropylureido)phenoxy)-2,3-dihydro-[1,4]dioxino[2,3-f]quinolin-5-yl)oxy)propyl)-4-methylpiperidin-4-yl)carbamate The preparation was carried out in a similar manner to Example 8, except that an equimolar equivalent of tert-butyl (1-(3-chloropropyl)-4-methylpiperidin-4-yl)carbamate was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. MS: 682[M+H]+.

2) Step 6): The final product (68 mg, 1 mmol) prepared in steps 1-5) was dissolved in dichloromethane (3 mL), to which trifluoroacetic acid (1 mL) was then added dropwise. The mixture was reacted for 3 hours. The reaction was quenched with a solution of ammonia in methanol at 0° C. The reaction solution was evaporated to dryness and purified by column chromatography to afford 20 mg of a white solid. $^1$H NMR (400 MHz, DMSO-$d_6$) δ 8.44 (d, J=5.2 Hz, 1H), 8.17 (d, J=9.0 Hz, 1H), 7.91 (s, 1H), 7.24 (d, J=2.8 Hz, 1H), 7.15 (d, J=3.0 Hz, 1H), 7.09-7.00 (m, 2H), 6.50 (d, J=5.1 Hz, 1H), 4.37-4.26 (m, 4H), 4.14 (t, J=6.4 Hz, 2H), 3.39 (s, 2H), 2.58-2.53 (m, 1H), 2.48-2.27 (m, 6H), 1.99-1.86 (m, 2H), 1.50-1.32 (m, 4H), 1.02 (s, 3H), 0.71-0.61 (m, 2H), 0.47-0.37 (m, 2H). MS: 582[M+H]+.

Example 62: Preparation of 1-(2-chloro-4-((5-(3-((2-methoxyethyl)(methyl)amino)propoxy)-2,3-dihydro-[1,4]dioxino[2,3-f]quinolin-10-yl)oxy)phenyl)-3-cyclopropylurea

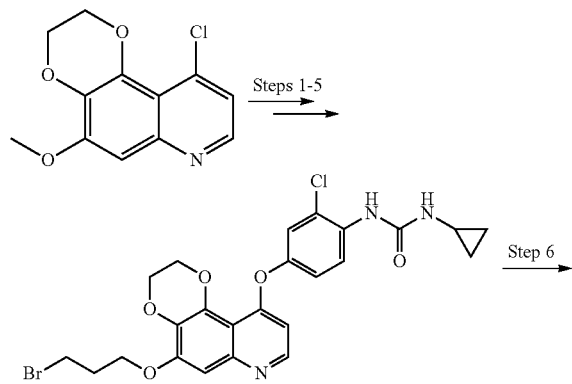

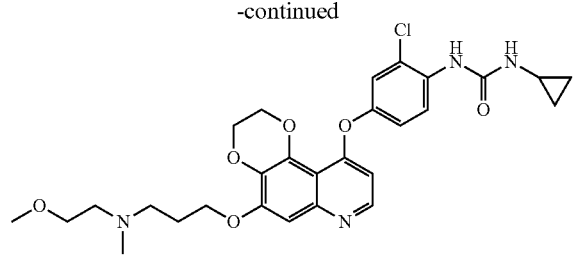

1) Steps 1-5): Preparation of 1-(4-((5-(3-bromopropoxy)-2,3-dihydro-[1,4]dioxino[2,3-f]quinolin-10-yl)oxy)-2-chlorophenyl)-3-cyclopropylurea The preparation was carried out in a similar manner to Example 8, except that an equimolar equivalent of 1,3-dibromoethane was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. MS: 548 [M+H]+.

2) Step 6): The final product (55 mg, 1 mmol) prepared in steps 1-5) was dissolved in acetonitrile (3 mL), to which triethylamine (202 mg, 2 mmol) and 2-methoxy-N-methylethan-1-amine (135 mg, 1.5 mmol) were then added. The mixture was reacted at 25° C. for 3 hours. The reaction solution was evaporated to dryness and subjected to column chromatography to afford 20 mg of a white solid. $^1$H NMR (600 MHz, DMSO-$d_6$) δ 8.47-8.41 (m, 1H), 8.17 (d, J=8.9 Hz, 1H), 7.90 (s, 1H), 7.24 (d, J=2.8 Hz, 1H), 7.13 (d, J=3.0 Hz, 1H), 7.08-7.02 (m, 2H), 6.53-6.48 (m, 1H), 4.37-4.26 (m, 4H), 4.15 (t, J=6.4 Hz, 2H), 3.41 (t, J=5.9 Hz, 2H), 3.21 (s, 3H), 2.58-2.55 (m, 1H), 2.54-2.51 (m, 4H), 2.22 (s, 3H), 1.96-1.87 (m, 2H), 0.70-0.61 (m, 2H), 0.46-0.38 (m, 2H). MS: 557[M+H]+.

Example 63: Preparation of 1-(2-chloro-4-((5-(3-(cyclobutyl(methyl)amino)propoxy)-2,3-dihydro-[1,4]dioxino[2,3-f]quinolin-10-yl)oxy)phenyl)-3-cyclopropylurea The preparation was carried out in a similar manner to Example 62, except that an equimolar equivalent of N-methylcyclobutylamine was used in place of 2-methoxy-N-methylethyl-1-amine in step 6) of Example 62. $^1$H NMR (600 MHz, DMSO-$d_6$) δ 8.44 (d, J=5.1 Hz, 1H), 8.17 (d, J=9.0 Hz, 1H), 7.91 (s, 1H), 7.24 (d, J=2.8 Hz, 1H), 7.15 (d, J=3.0 Hz, 1H), 7.05 (d, J=7.5 Hz, 2H), 6.51 (d, J=5.1 Hz, 1H), 4.35-4.26 (m, 4H), 4.15 (t, J=6.4 Hz, 2H), 2.84-2.74 (m, 1H), 2.59-2.53 (m, 1H), 2.37 (t, J=7.0 Hz, 2H), 2.05 (s, 3H), 2.02-1.94 (m, 2H), 1.94-1.87 (m, 2H), 1.81-1.70 (m, 2H), 1.63-1.52 (m, 2H), 0.72-0.59 (m, 2H), 0.46-0.37 (m, 2H). MS: 553[M+H]⁺.

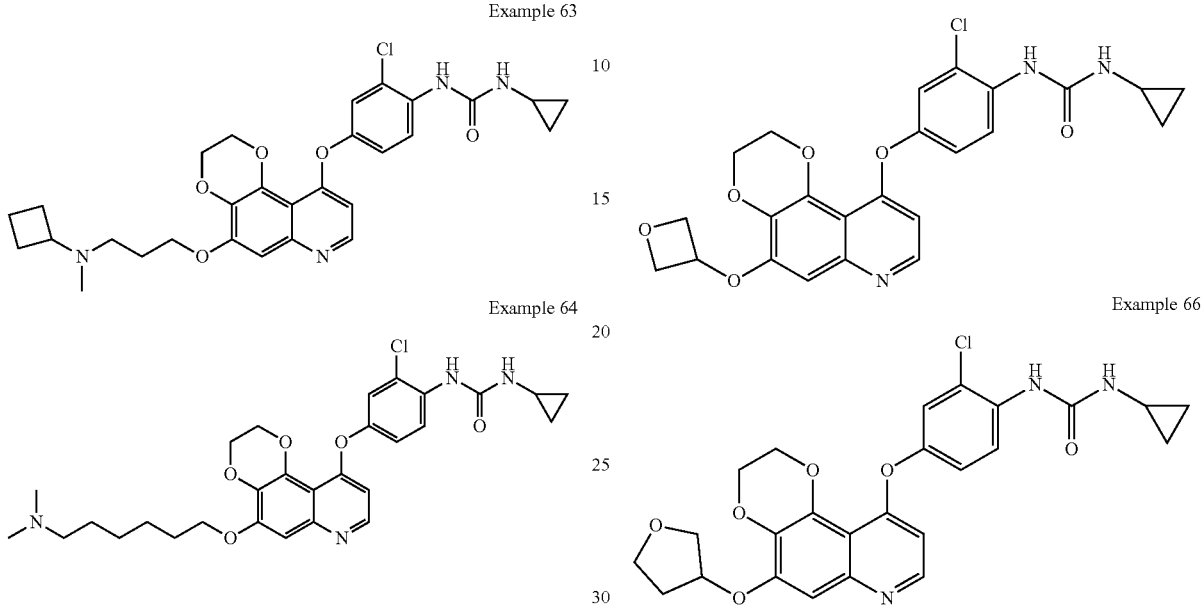

Example 63

Example 64

Example 65

Example 66

Example 64: Preparation of 1-(2-chloro-4-((5-((6-(dimethylamino)hexyl)oxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 6-chloro-N,N-dimethylhexan-1-amine was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. ¹H NMR (600 MHz, DMSO-d₆) δ 8.44 (dd, J=5.2, 2.7 Hz, 1H), 8.17 (dd, J=9.1, 2.7 Hz, 1H), 7.90 (d, J=2.7 Hz, 1H), 7.28-7.21 (m, 1H), 7.13 (d, J=2.8 Hz, 1H), 7.07-7.00 (m, 2H), 6.51 (dd, J=5.2, 2.7 Hz, 1H), 4.38-4.26 (m, 4H), 4.11 (t, J=6.6 Hz, 2H), 2.58-2.55 (m, 1H), 2.22-2.18 (m, 2H), 2.11 (s, 6H), 1.83-1.75 (m, 2H), 1.49-1.39 (m, 4H), 1.39-1.28 (m, 2H), 0.76-0.55 (m, 2H), 0.49-0.31 (m, 2H). MS: 555 [M+H]⁺.

Example 65: Preparation of 1-(2-chloro-4-((5-(oxetan-3-yloxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of oxetan-3-yl 4-methylbenzenesulfonate was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. ¹H NMR (400 MHz, DMSO-d₆) δ 8.44 (d, J=5.1 Hz, 1H), 8.18 (d, J=9.1 Hz, 1H), 7.91 (s, 1H), 7.26 (d, J=2.8 Hz, 1H), 7.14 (d, J=2.9 Hz, 1H), 7.05 (dd, J=9.1, 2.8 Hz, 1H), 6.70 (s, 1H), 6.52 (d, J=5.2 Hz, 1H), 5.51-5.41 (m, 1H), 5.02 (t, J=6.7 Hz, 2H), 4.66-4.58 (m, 2H), 4.39-4.29 (m, 4H), 2.57-2.54 (m, 1H), 0.71-0.61 (m, 2H), 0.47-0.37 (m, 2H). MS: 484[M+H]⁺.

Example 66: Preparation of 1-(2-chloro-4-((5-(((tetrahydrofuran-3-yl)oxy)-2,3-dihydro-[1,4]dioxino[2,3-f]quinolin-10-yl) oxy)phenyl)-3-cyclopropylurea The preparation was carried out in a similar manner to Example 8, except that an equimolar equivalent of tetrahydrofuran-3-yl 4-methylbenzenesulfonate was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. ¹H NMR (400 MHz, DMSO-d₆) δ 8.45 (d, J=5.2 Hz, 1H), 8.18 (d, J=9.1 Hz, 1H), 7.90 (s, 1H), 7.25 (d, J=2.8 Hz, 1H), 7.14 (d, J=2.9 Hz, 1H), 7.09-7.00 (m, 2H), 6.52 (d, J=5.2 Hz, 1H), 5.24-5.16 (m, 1H), 4.37-4.26 (m, 4H), 4.01-3.92 (m, 1H), 3.92-3.83 (m, 2H), 3.83-3.74 (m, 1H), 2.59-2.54 (m, 1H), 2.40-2.26 (m, 1H), 2.11-2.00 (m, 1H), 0.70-0.61 (m, 2H), 0.46-0.38 (m, 2H). MS: 498[M+H]⁺.

Example 67: Preparation of 1-(2-chloro-4-((5-(((tetrahydro-2H-pyran-4-yl)oxy)-2,3-dihydro-[1,4]dioxino[2,3-f]quinolin-1-0-yl)oxy)phenyl)-3-cyclopropylurea The preparation was carried out in a similar manner to Example 8, except that an equimolar equivalent of tetrahydro-2H-pyran-4-yl 4-methylbenzenesulfonate was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. ¹H NMR (600 MHz, DMSO-d₆) δ 8.37 (d, J=5.1 Hz, 1H), 8.10 (d, J=9.0 Hz, 1H), 7.83 (s, 1H), 7.18 (d, J=2.8 Hz, 1H), 7.11 (s, 1H), 7.07 (d, J=3.0 Hz, 1H), 6.98 (dd, J=9.1, 2.8 Hz, 1H), 6.44 (d, J=5.1 Hz, 1H), 4.78-4.68 (m, 1H), 4.31-4.18 (m, 4H), 3.88-3.76 (m, 2H), 3.52-3.43 (m, 2H), 2.52-2.48 (m, 1H), 2.02-1.97 (m, 2H), 1.63-1.55 (m, 2H), 0.64-0.54 (m, 2H), 0.40-0.31 (m, 2H). MS: 512[M+H]$^+$.

Example 67

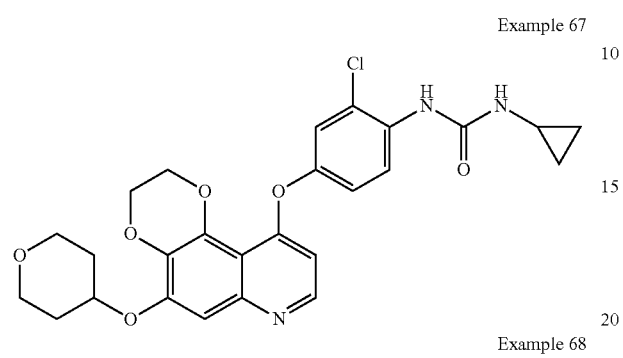

Example 68

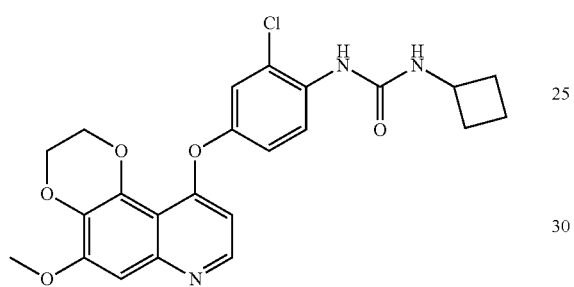

Example 68: Preparation of 1-(2-chloro-4-((5-methoxy-2,3-dihydro-[1,4]dioxino[2,3-f]quinolin-10-yl)oxy)phenyl)-3-cyclobutylurea The preparation was carried out in a similar manner to Example 1, except that an equimolar equivalent of 3-chloro-4-nitrophenol was used in place of p-nitrophenol in step 1) of Example 1, and an equimolar equivalent of cyclobutylamine was used in place of 4-chloro-3-(trifluoromethyl)aniline in step 3) of Example 1. $^1$H NMR (400 MHz, DMSO-d$_6$) δ 8.44 (d, J=5.2 Hz, 1H), 8.15 (d, J=8.7 Hz, 1H), 7.92 (s, 1H), 7.30-7.19 (m, 2H), 7.11-6.98 (m, 2H), 6.51 (d, J=5.2 Hz, 1H), 4.37-4.25 (m, 4H), 4.19-4.06 (m, 1H), 3.92 (s, 3H), 2.29-2.15 (m, 2H), 1.91-1.75 (m, 2H), 1.71-1.54 (m, 2H). MS: 456[M+H]$^+$.

Example 69: Preparation of 1-(2-chloro-4-((5-methoxy-2,3-dihydro-[1,4]dioxino[2,3-f]quinolin-10-yl)oxy)phenyl)-3-cyclopentylurea The preparation was carried out in a similar manner to Example 1, except that an equimolar equivalent of 3-chloro-4-nitrophenol was used in place of p-nitrophenol in step 1) of Example 1, and an equimolar equivalent of cyclopentylamine was used in place of 4-chloro-3-(trifluoromethyl)aniline in step 3) of Example 1. $^1$H NMR (400 MHz, DMSO-d$_6$) δ 8.44 (d, J=5.2 Hz, 1H), 8.21 (d, J=9.1 Hz, 1H), 7.92 (s, 1H), 7.24 (d, J=2.8 Hz, 1H), 7.11-6.99 (m, 3H), 6.50 (d, J=5.2 Hz, 1H), 4.36-4.26 (m, 4H), 4.00-3.87 (m, 4H), 1.91-1.77 (m, 2H), 1.71-1.59 (m, 2H), 1.59-1.48 (m, 2H), 1.45-1.30 (m, 2H). MS: 470[M+H]$^+$.

Example 69

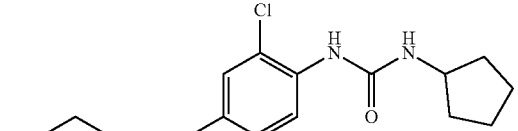

Example 70

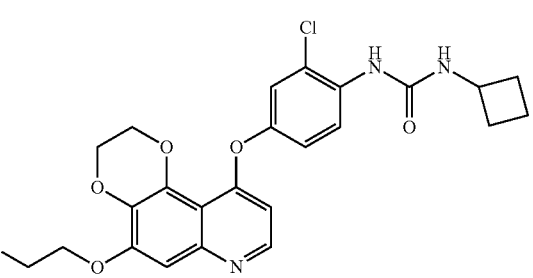

Example 70: Preparation of 1-(2-chloro-4-((5-(2-methoxyethoxy)-2,3-dihydro-[1,4]dioxino[2,3-f]quinolin-10-yl)oxy)phenyl)-3-cyclobutylurea The preparation was carried out in a similar manner to Example 8, except that an equimolar equivalent of 3-chloro-4-nitrophenol was used in place of p-nitrophenol in step 3) of Example 8, and an equimolar equivalent of cyclobutylamine was used in place of 4-chloro-3-(trifluoromethyl)aniline in step 5) of Example 8. $^1$H NMR (600 MHz, DMSO-d$_6$) δ 8.44 (d, J=5.2 Hz, 1H), 8.15 (d, J=9.1 Hz, 1H), 7.92 (s, 1H), 7.28-7.21 (m, 2H), 7.07 (s, 1H), 7.03 (dd, J=9.1, 2.8 Hz, 1H), 6.50 (d, J=5.2 Hz, 1H), 4.35-4.27 (m, 4H), 4.27-4.21 (m, 2H), 4.17-4.08 (m, 1H), 3.77-3.70 (m, 2H), 3.34 (s, 3H), 2.26-2.18 (m, 2H), 1.90-1.78 (m, 2H), 1.71-1.54 (m, 2H). MS: 500[M+H]$^+$.

Example 71: Preparation of 1-(2-chloro-4-((5-(2-methoxyethoxy)-2,3-dihydro-[1,4]dioxino[2,3-f]quinolin-10-yl)oxy)phenyl)-3-cyclopentylurea The preparation was carried out in a similar manner to Example 8, except that an equimolar equivalent of 3-chloro-4-nitrophenol was used in place of p-nitrophenol in step 3) of Example 8, and an equimolar equivalent of cyclopentylamine was used in place of 4-chloro-3-(trifluoromethyl)aniline in step 5) of Example 8. $^1$H NMR (400 MHz, DMSO-d$_6$) δ 8.43 (d, J=5.2 Hz, 1H), 8.21 (d, J=9.2 Hz, 1H), 7.92 (s, 1H), 7.24 (d, J=2.8 Hz, 1H), 7.11-7.00 (m, 3H), 6.49 (d, J=5.2 Hz, 1H), 4.38-4.27 (m, 4H), 4.27-4.20 (m, 2H), 4.01-3.88 (m, 1H), 3.77-3.69 (m, 2H), 3.30 (s, 3H), 1.91-1.78 (m, 2H), 1.69-1.60 (m, 2H), 1.60-1.49 (m, 2H), 1.45-1.32 (m, 2H). MS: 514[M+H]$^+$.

Example 71

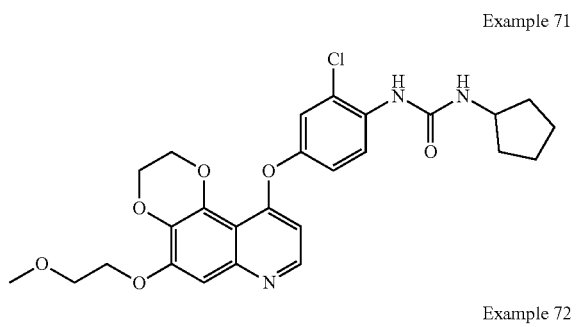

Example 72

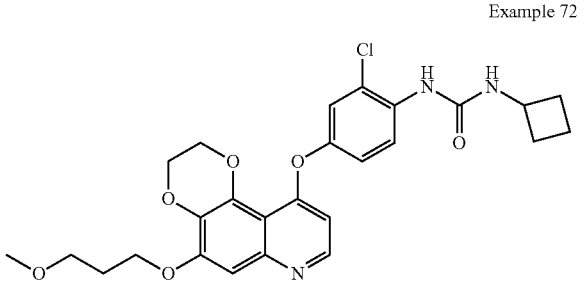

Example 73

Example 74

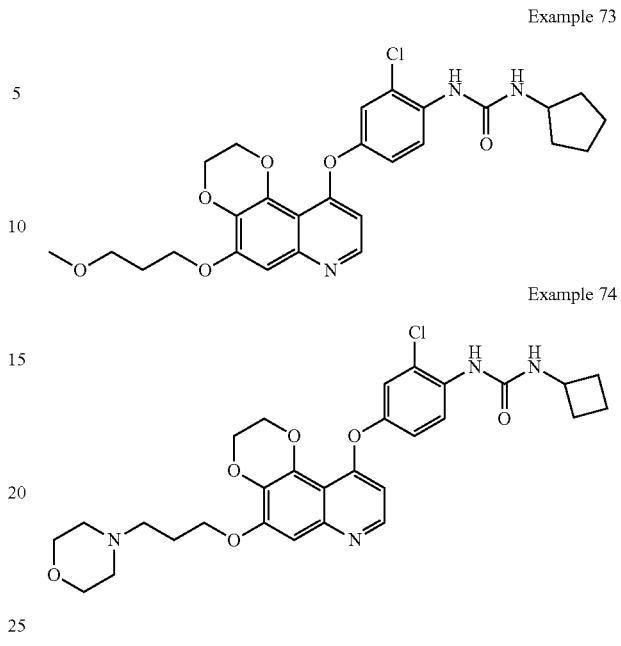

Example 72: Preparation of 1-(2-chloro-4-((5-(3-methoxypropoxy)-2,3-dihydro-[1,4]dioxino[2,3-f]quinolin-10-yl)oxy)phenyl)-3-cyclobutylurea The preparation was carried out in a similar manner to Example 8, except that an equimolar equivalent of 1-bromo-3-methoxypropane was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclobutylamine was used in place of 4-chloro-3-(trifluoromethyl)aniline in step 5) of Example 8. $^1$H NMR (400 MHz, DMSO-$d_6$) δ 8.44 (d, J=5.2 Hz, 1H), 8.15 (d, J=9.0 Hz, 1H), 7.92 (s, 1H), 7.28-7.21 (m, 2H), 7.09-6.99 (m, 2H), 6.53-6.47 (m, 1H), 4.38-4.26 (m, 4H), 4.22-4.07 (m, 3H), 3.51 (t, J=6.3 Hz, 2H), 3.27 (s, 3H), 2.26-2.15 (m, 2H), 2.09-1.98 (m, 2H), 1.91-1.76 (m, 2H), 1.70-1.57 (m, 2H). MS: 514[M+H]$^+$.

Example 73: Preparation of 1-(2-chloro-4-((5-(3-methoxypropoxy)-2,3-dihydro-[1,4]dioxino[2,3-f]quinolin-10-yl)oxy)phenyl)-3-cyclopentylurea The preparation was carried out in a similar manner to Example 8, except that an equimolar equivalent of 1-bromo-3-methoxypropane was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopentylamine was used in place of 4-chloro-3-(trifluoromethyl)aniline in step 5) of Example 8. $^1$H NMR (600 MHz, DMSO-$d_6$) δ 8.37 (d, J=5.2 Hz, 1H), 8.14 (d, J=9.1 Hz, 1H), 7.86 (s, 1H), 7.17 (d, J=2.8 Hz, 1H), 7.02-6.92 (m, 3H), 6.43 (d, J=5.1 Hz, 1H), 4.30-4.19 (m, 4H), 4.10 (t, J=6.4 Hz, 2H), 3.93-3.81 (m, 1H), 3.45 (t, J=6.3 Hz, 2H), 3.21 (s, 3H), 2.01-1.91 (m, 2H), 1.83-1.73 (m, 2H), 1.64-1.53 (m, 2H), 1.53-1.44 (m, 2H), 1.37-1.25 (m, 2H). MS: 528[M+H]$^+$.

Example 74: Preparation of 1-(2-chloro-4-((5-(3-morpholinopropoxy)-2,3-dihydro-[1,4]dioxino[2,3-f]quinolin-10-yl)oxy) phenyl)-3-cyclobutylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclobutylamine was used in place of 4-chloro-3-(trifluoromethyl)aniline in step 5) of Example 8. $^1$H NMR (400 MHz, DMSO-$d_6$) δ 8.45 (d, J=5.2 Hz, 1H), 8.18-8.13 (m, 1H), 7.92 (s, 1H), 7.28-7.21 (m, 2H), 7.08 (s, 1H), 7.02 (dd, J=9.1, 2.8 Hz, 1H), 6.51 (d, J=5.2 Hz, 1H), 4.38-4.26 (m, 4H), 4.25-4.04 (m, 3H), 3.86-3.51 (m, 4H), 2.69-2.52 (m, 4H), 2.48-2.32 (m, 2H), 2.25-2.15 (m, 2H), 2.15-1.95 (m, 2H), 1.92-1.76 (m, 2H), 1.71-1.55 (m, 2H). MS: 569[M+H]$^+$.

Example 75: Preparation of 1-(2-chloro-4-((5-(3-morpholinopropoxy)-2,3-dihydro-[1,4]dioxino[2,3-f]quinolin-10-yl)oxy) phenyl)-3-cyclopentylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopentylamine was used in place of 4-chloro-3-(trifluoromethyl)aniline in step 5) of Example 8. $^1$H NMR (400 MHz, DMSO-$d_6$) δ 8.43 (d, J=5.1 Hz, 1H), 8.21 (d, J=9.1 Hz, 1H), 7.92 (s, 1H), 7.24 (d, J=2.8 Hz, 1H), 7.09-6.98 (m, 3H), 6.49 (d, J=5.1 Hz, 1H), 4.37-4.26 (m, 4H), 4.16 (t, J=6.4 Hz, 2H), 4.00-3.90 (m, 1H), 3.59 (t, J=4.6 Hz, 4H), 2.46 (t, J=7.1 Hz, 2H), 2.38 (t, J=4.6 Hz, 4H), 2.02-1.90 (m, 2H), 1.90-1.78 (m, 2H), 1.71-1.60 (m, 2H), 1.60-1.49 (m, 2H), 1.45-1.32 (m, 2H). MS: 583[M+H]$^+$.

Example 75

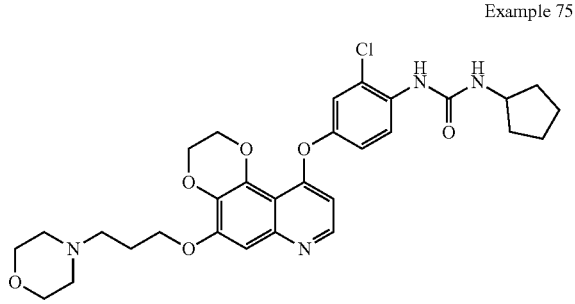

Example 76

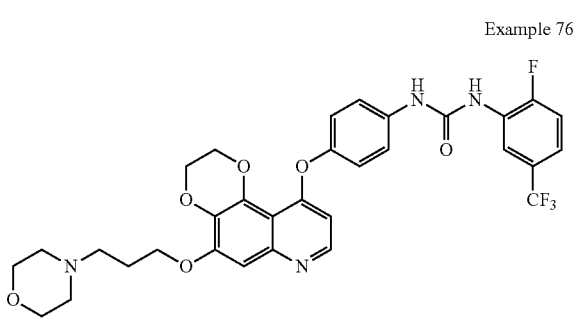

line was used in place of 4-chloro-3-(trifluoromethyl)aniline in step 5) of Example 8. $^1$H NMR (600 MHz, DMSO-d$_6$) δ 9.27 (s, 1H), 8.90 (d, J=2.9 Hz, 1H), 8.62 (dd, J=7.2, 2.3 Hz, 1H), 8.41 (d, J=5.2 Hz, 1H), 7.60-7.46 (m, 3H), 7.45-7.35 (m, 1H), 7.15-7.07 (m, 2H), 7.05 (s, 1H), 6.43 (d, J=5.2 Hz, 1H), 4.38-4.29 (m, 4H), 4.17 (t, J=6.4 Hz, 2H), 3.59 (t, J=4.6 Hz, 4H), 2.46 (t, J=7.1 Hz, 2H), 2.42-2.31 (m, 4H), 2.01-1.91 (m, 2H). MS: 643[M+H]$^+$.

Example 77: Preparation of 1-(4-fluorophenyl)-3-(4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8, and an equimolar equivalent of p-fluoroaniline was used in place of 4-chloro-3-(trifluoromethyl)aniline in step 5) of Example 8. $^1$H NMR (400 MHz, DMSO-d$_6$) δ 8.80 (d, J=17.3 Hz, 2H), 8.40 (d, J=5.2 Hz, 1H), 7.57-7.51 (m, 2H), 7.50-7.44 (m, 2H), 7.16-7.02 (m, 5H), 6.41 (d, J=5.2 Hz, 1H), 4.39-4.28 (m, 4H), 4.17 (t, J=6.4 Hz, 2H), 3.59 (t, J=4.6 Hz, 4H), 2.49-2.45 (m, 2H), 2.40 (t, J=4.6 Hz, 4H), 2.01-1.91 (m, 2H). MS: 575[M+H]$^+$.

Example 77

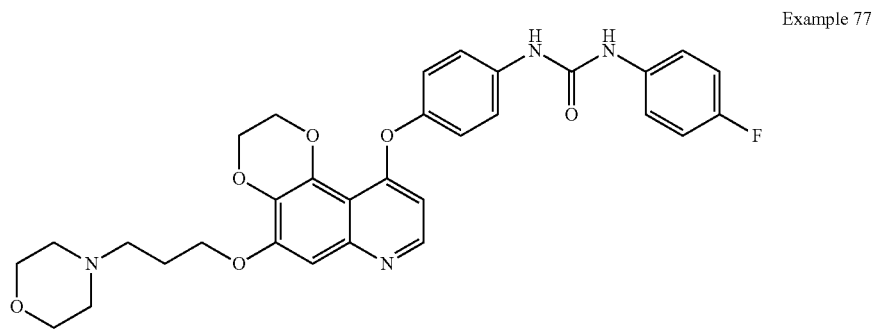

Example 78

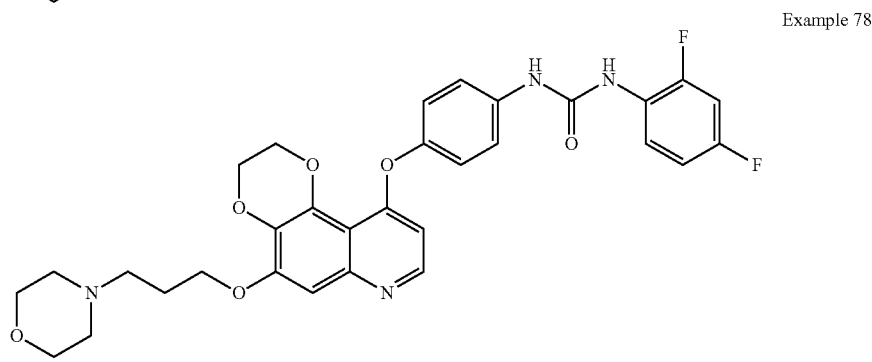

Example 76: Preparation of 1-(2-fluoro-5-(trifluoromethyl)phenyl)-3-(4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8, and an equimolar equivalent of 2-fluoro-5-(trifluoromethyl)ani- Example 78: Preparation of 1-(2,4-difluorophenyl)-3-(4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8, and an equimolar equivalent of 2,4-difluoroaniline was used in place of 4-chloro-3-(trifluoromethyl)aniline in step 5) of Example 8. ¹H NMR (600 MHz, DMSO-d₆) δ 9.15 (d, J=3.4 Hz, 1H), 8.55 (d, J=3.0 Hz, 1H), 8.40 (d, J=5.2 Hz, 1H), 8.12-8.02 (m, 1H), 7.57-7.49 (m, 2H), 7.36-7.26 (m, 1H), 7.12-7.06 (m, 2H), 7.06-7.00 (m, 2H), 6.41 (d, J=5.2 Hz, 1H), 4.37-4.29 (m, 4H), 4.16 (t, J=6.4 Hz, 2H), 3.59 (t, J=4.6 Hz, 4H), 2.46 (t, J=7.2 Hz, 2H), 2.43-2.31 (m, 4H), 2.01-1.92 (m, 2H). MS: 593[M+H]⁺.

Example 79: Preparation of 1-(2-chloro-4-((5-methoxy-2,3-dihydro-[1,4]dioxino[2,3-f]quinolin-10-yl)oxy)phenyl)-3-methylurea The preparation was carried out in a similar manner to Example 1, except that an equimolar equivalent of 3-chloro-4-nitrophenol was used in place of p-nitrophenol in step 1) of Example 1, and an equimolar equivalent of methylamine was used in place of 4-chloro-3-(trifluoromethyl)aniline in step 3) of Example 1. ¹H NMR (600 MHz, DMSO-d₆) δ 8.45 (d, J=5.1 Hz, 1H), 8.14 (d, J=9.0 Hz, 1H), 8.05 (s, 1H), 7.24 (d, J=2.8 Hz, 1H), 7.09-7.01 (m, 2H), 6.89-6.78 (m, 1H), 6.52 (d, J=5.1 Hz, 1H), 4.37-4.27 (m, 4H), 3.92 (s, 3H), 2.66 (d, J=4.5 Hz, 3H). MS: 416[M+H]⁺.

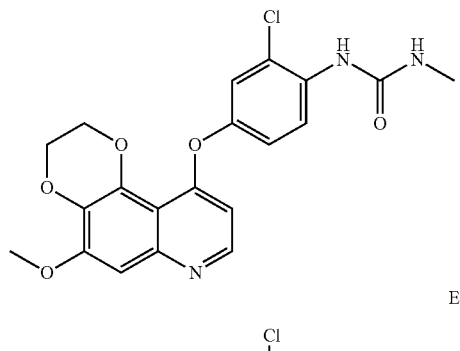

Example 79

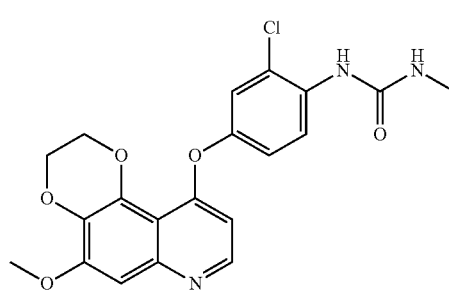

Example 80

Example 80: Preparation of 1-(2-chloro-4-((5-methoxy-2,3-dihydro-[1,4]dioxino[2,3-f]quinolin-10-yl)oxy)phenyl)-3-ethylurea The preparation was carried out in a similar manner to Example 1, except that an equimolar equivalent of 3-chloro-4-nitrophenol was used in place of p-nitrophenol in step 1) of Example 1, and an equimolar equivalent of ethylamine was used in place of 4-chloro-3-(trifluoromethyl)aniline in step 3) of Example 1. ¹H NMR (600 MHz, DMSO-d₆) δ 8.44 (d, J=5.1 Hz, 1H), 8.17 (d, J=9.0 Hz, 1H), 7.98 (s, 1H), 7.24 (d, J=2.8 Hz, 1H), 7.07 (s, 1H), 7.04 (dd, J=9.1, 2.8 Hz, 1H), 6.95-6.90 (m, 1H), 6.51 (d, J=5.2 Hz, 1H), 4.36-4.27 (m, 4H), 3.92 (s, 3H), 3.17-3.07 (m, 2H), 1.07 (t, J=7.2 Hz, 3H). MS: 430[M+H]⁺.

Example 81: Preparation of 1-(2-chloro-4-((5-methoxy-2,3-dihydro-[1,4]dioxino[2,3-f]quinolin-10-yl)oxy)phenyl)-3-propylurea The preparation was carried out in a similar manner to Example 1, except that an equimolar equivalent of 3-chloro-4-nitrophenol was used in place of p-nitrophenol in step 1) of Example 1, and an equimolar equivalent of propylamine was used in place of 4-chloro-3-(trifluoromethyl)aniline in step 3) of Example 1. ¹H NMR (600 MHz, DMSO-d₆) δ 8.44 (d, J=5.2 Hz, 1H), 8.18 (d, J=9.1 Hz, 1H), 8.01 (s, 1H), 7.24 (d, J=2.8 Hz, 1H), 7.07 (s, 1H), 7.04 (dd, J=9.1, 2.8 Hz, 1H), 6.97 (d, J=5.6 Hz, 1H), 6.51 (d, J=5.2 Hz, 1H), 4.41-4.23 (m, 4H), 3.92 (s, 3H), 3.11-3.02 (m, 2H), 1.50-1.38 (m, 2H), 0.90 (t, J=7.4 Hz, 3H). MS: 444[M+H]⁺.

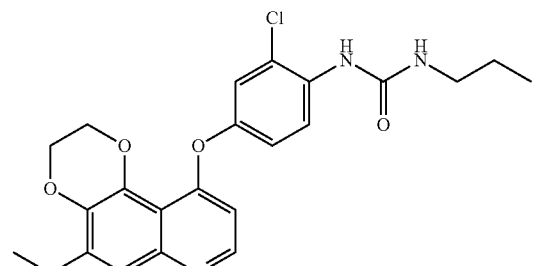

Example 81

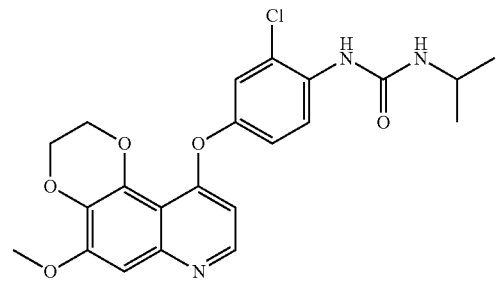

Example 82

Example 82: Preparation of 1-(2-chloro-4-((5-methoxy-2,3-dihydro-[1,4]dioxino[2,3-f]quinolin-10-yl)oxy)phenyl)-3-isopropylurea The preparation was carried out in a similar manner to Example 1, except that an equimolar equivalent of 3-chloro-4-nitrophenol was used in place of p-nitrophenol in step 1) of Example 1, and an equimolar equivalent of isopropylamine was used in place of 4-chloro-3-(trifluoromethyl)aniline in step 3) of Example 1. ¹H NMR (600 MHz, DMSO-d₆) δ 8.44 (d, J=5.2 Hz, 1H), 8.20 (d, J=9.1 Hz, 1H), 7.93 (s, 1H), 7.24 (d, J=2.8 Hz, 1H), 7.07 (s, 1H), 7.04 (dd, J=9.0, 2.8 Hz, 1H), 6.91 (d, J=7.3 Hz, 1H), 6.50 (d, J=5.2 Hz, 1H), 4.35-4.24 (m, 4H), 3.92 (s, 3H), 3.80-3.70 (m, 1H), 1.11 (d, J=6.5 Hz, 6H). MS: 444 [M+H]⁺.

Example 83: Preparation of 1-(2-chloro-4-((5-methoxy-2,3-dihydro-[1,4]dioxino[2,3-f]quinolin-10-yl)oxy)phenyl)-3-isobutylurea The preparation was carried out in a similar manner to Example 1, except that an equimolar equivalent of 3-chloro-4-nitrophenol was used in place of p-nitrophenol in step 1)

of Example 1, and an equimolar equivalent of isobutylamine was used in place of 4-chloro-3-(trifluoromethyl)aniline in step 3) of Example 1. $^1$H NMR (600 MHz, DMSO-d$_6$) δ 8.44 (d, J=5.1 Hz, 1H), 8.19 (d, J=9.0 Hz, 1H), 8.05 (s, 1H), 7.24 (d, J=2.7 Hz, 1H), 7.07 (s, 1H), 7.04 (dd, J=9.1, 2.8 Hz, 1H), 7.02-6.98 (m, 1H), 6.51 (d, J=5.1 Hz, 1H), 4.38-4.23 (m, 4H), 3.92 (s, 3H), 3.00-2.87 (m, 2H), 1.73-1.64 (m, 1H), 0.89 (d, J=6.6 Hz, 6H). MS: 458[M+H]$^+$.

Example 83

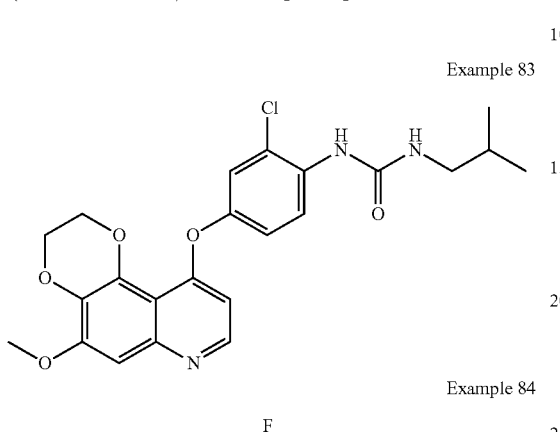

Example 84

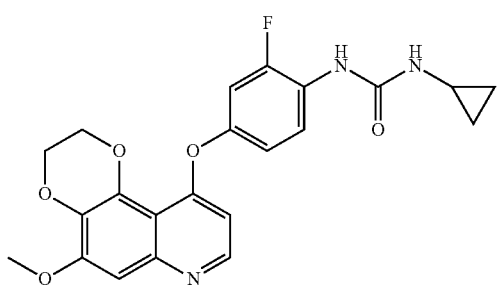

Example 84: Preparation of 1-cyclopropyl-3-(2-fluoro-4-((5-methoxy-2,3-dihydro-[1,4]dioxino[2,3-f]quinolin-10-yl)oxy)phenyl)urea The preparation was carried out in a similar manner to Example 1, except that an equimolar equivalent of 3-fluoro-4-nitrophenol was used in place of p-nitrophenol in step 1) of Example 1, and an equimolar equivalent of cyclopropylamine was used in place of 4-chloro-3-(trifluoromethyl)aniline in step 3) of Example 1. $^1$H NMR (400 MHz, DMSO-d$_6$) δ 8.44 (d, J=5.2 Hz, 1H), 8.17-8.05 (m, 2H), 7.15-7.03 (m, 2H), 6.87 (dd, J=8.7, 2.5 Hz, 1H), 6.76 (d, J=2.9 Hz, 1H), 6.50 (d, J=5.2 Hz, 1H), 4.38-4.26 (m, 4H), 3.92 (s, 3H), 2.59-2.52 (m, 1H), 0.70-0.59 (m, 2H), 0.45-0.34 (m, 2H). MS: 426[M+H]$^+$.

Example 85: Preparation of 1-(2-chloro-4-((5-(3-morpholinopropoxy)-2,3-dihydro-[1,4]dioxino[2,3-f]quinolin-10-yl)oxy) phenyl)-3-methylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of methylamine was used in place of 4-chloro-3-(trifluoromethyl)aniline in step 5) of Example 8. $^1$H NMR (400 MHz, DMSO-d$_6$) δ 8.44 (d, J=5.2 Hz, 1H), 8.14 (d, J=9.1 Hz, 1H), 8.03 (s, 1H), 7.23 (d, J=2.8 Hz, 1H), 7.07-7.00 (m, 2H), 6.81 (d, J=4.7 Hz, 1H), 6.51 (d, J=5.2 Hz, 1H), 4.36-4.26 (m, 4H), 4.16 (t, J=6.4 Hz, 2H), 3.59 (t, J=4.6 Hz, 4H), 2.66 (d, J=4.5 Hz, 3H), 2.46 (t, J=7.1 Hz, 2H), 2.42-2.33 (m, 4H), 2.01-1.90 (m, 2H). MS: 529[M+H]$^+$.

Example 85

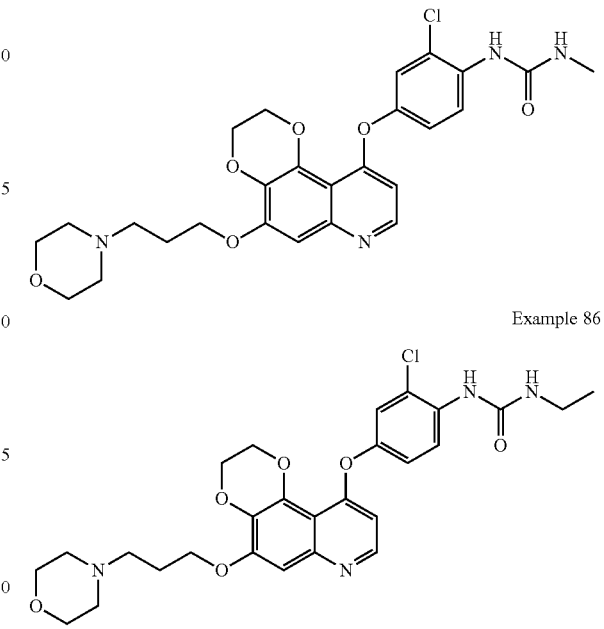

Example 86

Example 86: Preparation of 1-(2-chloro-4-((5-(3-morpholinopropoxy)-2,3-dihydro-[1,4]dioxino[2,3-f]quinolin-10-yl)oxy) phenyl)-3-ethylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of ethylamine was used in place of 4-chloro-3-(trifluoromethyl)aniline in step 5) of Example 8. $^1$H NMR (400 MHz, DMSO-d$_6$) δ 8.44 (d, J=5.1 Hz, 1H), 8.16 (d, J=9.1 Hz, 1H), 7.98 (s, 1H), 7.23 (d, J=2.8 Hz, 1H), 7.08-7.00 (m, 2H), 6.97-6.90 (m, 1H), 6.50 (d, J=5.1 Hz, 1H), 4.36-4.27 (m, 4H), 4.17 (t, J=6.4 Hz, 2H), 3.59 (t, J=4.6 Hz, 4H), 3.18-3.06 (m, 2H), 2.46 (t, J=7.1 Hz, 2H), 2.42-2.33 (m, 4H), 2.02-1.91 (m, 2H), 1.07 (t, J=7.2 Hz, 3H). MS: 543[M+H]$^+$.

Example 87: Preparation of 1-(2-chloro-4-((5-(3-morpholinopropoxy)-2,3-dihydro-[1,4]dioxino[2,3-f]quinolin-10-yl)oxy) phenyl)-3-prop ylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of propylamine was used in place of 4-chloro-3-(trifluoromethyl)aniline in step 5) of Example 8. $^1$H NMR (400 MHz, DMSO-d$_6$) δ 8.43 (d, J=5.2 Hz, 1H), 8.18 (d, J=9.0 Hz, 1H), 8.00 (s, 1H), 7.23 (d, J=2.8 Hz, 1H), 7.08-7.00 (m, 2H), 7.00-6.93 (m, 1H), 6.50 (d, J=5.1 Hz, 1H), 4.36-4.27 (m, 4H), 4.17 (t, J=6.4 Hz, 2H), 3.59 (t, J=4.6 Hz, 4H), 3.10-3.02 (m, 2H), 2.46 (t, J=7.1 Hz, 2H), 2.42-2.34 (m, 4H), 2.01-1.89 (m, 2H), 1.52-1.38 (m, 2H), 0.89 (t, J=7.4 Hz, 3H). MS: 557[M+H]$^+$.

$^1$H NMR (400 MHz, DMSO-d$_6$) δ 8.46 (d, J=5.2 Hz, 1H), 8.19 (d, J=9.1 Hz, 1H), 8.06 (s, 1H), 7.24 (d, J=2.8 Hz, 1H), 7.11 (s, 1H), 7.07-6.97 (m, 2H), 6.53 (d, J=5.2 Hz, 1H), 4.38-4.28 (m, 4H), 4.23 (t, J=6.0 Hz, 2H), 3.90-3.72 (m, 4H), 3.53-3.46 (m, 2H), 3.13-3.07 (m, 4H), 2.94 (t, J=6.2 Hz, 2H), 2.24-2.13 (m, 2H), 1.76-1.63 (m, 1H), 0.89 (d, J=6.6 Hz, 6H). MS: 571[M+H]$^+$.

Example 87

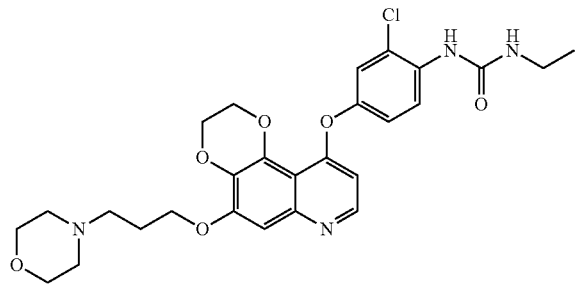

Example 89

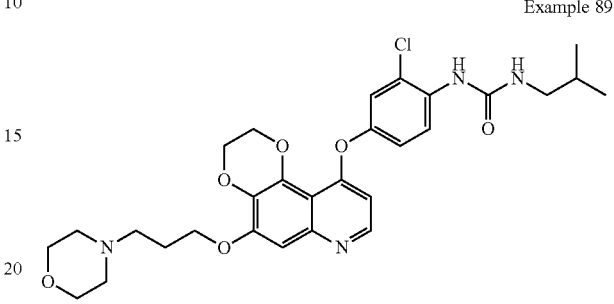

Example 88

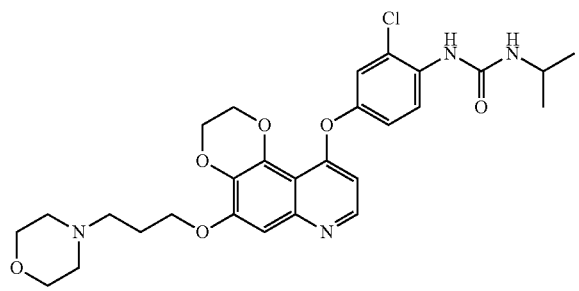

Example 90

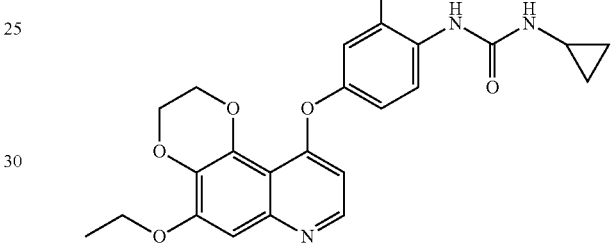

Example 88: Preparation of 1-(2-chloro-4-((5-(3-morpholinopropoxy)-2,3-dihydro-[1,4]dioxino[2,3-f]quinolin-10-yl)oxy)phenyl)-3-isopropylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of isopropylamine was used in place of 4-chloro-3-(trifluoromethyl)aniline in step 5) of Example 8. $^1$H NMR (400 MHz, DMSO-d$_6$) δ 8.43 (d, J=5.2 Hz, 1H), 8.20 (d, J=9.1 Hz, 1H), 7.92 (s, 1H), 7.23 (d, J=2.8 Hz, 1H), 7.07-7.00 (m, 2H), 6.90 (d, J=7.3 Hz, 1H), 6.49 (d, J=5.2 Hz, 1H), 4.36-4.27 (m, 4H), 4.16 (t, J=6.4 Hz, 2H), 3.83-3.69 (m, 1H), 3.59 (t, J=4.6 Hz, 4H), 2.46 (t, J=7.1 Hz, 2H), 2.42-2.34 (m, 4H), 2.02-1.90 (m, 2H), 1.11 (d, J=6.5 Hz, 6H). MS: 557[M+H]$^+$.

Example 89: Preparation of 1-(2-chloro-4-((5-(3-morpholinopropoxy)-2,3-dihydro-[1,4]dioxino[2,3-f]quinolin-10-yl)oxy) phenyl)-3-isobutylurea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of isobutylamine was used in place of 4-chloro-3-(trifluoromethyl)aniline in step 5) of Example 8.

Example 90: Preparation of 1-cyclopropyl-3-(4-((5-ethoxy-2,3-dihydro-[1,4]dioxino[2,3-f]quinolin-10-yl)oxy)-2-fluorophenyl)urea The preparation was carried out in a similar manner to Example 8, except that an equimolar equivalent of bromoethane was used in place of 1-bromo-2-methoxyethane in step 2) of Example 8, an equimolar equivalent of 3-fluoro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (400 MHz, DMSO-d$_6$) δ 8.43 (d, J=5.2 Hz, 1H), 8.18-8.03 (m, 2H), 7.17-6.98 (m, 2H), 6.87 (dd, J=9.0, 2.8 Hz, 1H), 6.77 (d, J=2.9 Hz, 1H), 6.49 (d, J=5.2 Hz, 1H), 4.38-4.23 (m, 4H), 4.18 (q, J=7.0 Hz, 2H), 2.58-2.52 (m, 1H), 1.41 (t, J=7.0 Hz, 3H), 0.68-0.58 (m, 2H), 0.48-0.33 (m, 2H). MS: 440[M+H]$^+$.

Example 91: Preparation of 1-cyclopropyl-3-(2-fluoro-4-((5-(2-methoxyethoxy)-2,3-dihydro-[1,4]dioxino[2,3-f]quinolin-10-yl)oxy)phenyl)urea The preparation was carried out in a similar manner to Example 8, except that an equimolar equivalent of 3-fluoro-4-nitrophenol was used in place of p-nitrophenol in step 3) of Example 8, and an equimolar equivalent of cyclopropylamine was used in place of 4-chloro-3-(trifluoromethyl) aniline in step 5) of Example 8. $^1$H NMR (400 MHz, DMSO-d$_6$) δ 8.43 (d, J=5.1 Hz, 1H), 8.17-8.06 (m, 2H), 7.16-7.04 (m, 2H), 6.88 (dd, J=9.0, 2.8 Hz, 1H), 6.76 (d, J=2.9 Hz, 1H), 6.50 (d, J=5.2 Hz, 1H), 4.38-4.27 (m, 4H), 4.27-4.19 (m, 2H), 3.78-3.70 (m, 2H), 3.34 (s, 3H), 2.58-2.53 (m, 1H), 0.76-0.55 (m, 2H), 0.49-0.34 (m, 2H). MS: 470[M+H]+.

Example 91

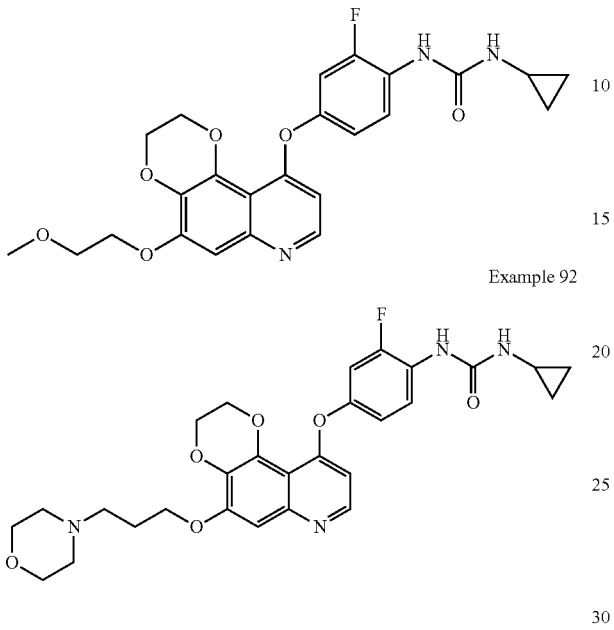

Example 92

Example 92: Preparation of 1-cyclopropyl-3-(2-fluoro-4-((5-(3-morpholinopropoxy)-2,3-dihydro-[1,4]dioxino[2,3-f]quinolin-10-yl)oxy)phenyl)-3-urea The preparation was carried out in a similar manner to Example 8, except that an equimolar equivalent of 4-(3-chloropropyl)morpholine hydrochloride was used in place of 1-bromo-2-methoxyethane in step 2) of Example 8, an equimolar equivalent of 3-fluoro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (400 MHz, DMSO-$d_6$) δ 8.43 (d, J=5.2 Hz, 1H), 8.16-8.06 (m, 2H), 7.13-7.03 (m, 2H), 6.87 (dd, J=9.0, 2.7 Hz, 1H), 6.76 (d, J=2.9 Hz, 1H), 6.50 (d, J=5.2 Hz, 1H), 4.35-4.26 (m, 4H), 4.16 (t, J=6.4 Hz, 2H), 3.59 (t, J=4.6 Hz, 4H), 2.59-2.53 (m, 1H), 2.46 (t, J=7.1 Hz, 2H), 2.42-2.33 (m, 4H), 2.02-1.92 (m, 2H), 0.68-0.59 (m, 2H), 0.43-0.36 (m, 2H). MS: 539[M+H]+.

Example 93: Preparation of 1-(2-chloro-4-((5-(3-cyanopropoxy)-2,3-dihydro-[1,4]dioxino[2,3-f]quinolin-10-yl)oxy)phenyl)-3-cyclopropylurea The preparation was carried out in a similar manner to Example 8, except that an equimolar equivalent of 4-bromobutyronitrile was used in place of 1-bromo-2-methoxyethane in step 2) of Example 8, an equimolar equivalent of 3-chloro-4-nitrophenol was used in place of p-nitrophenol in step 3) of Example 8, and an equimolar equivalent of cyclopropylamine was used in place of 4-chloro-3-(trifluoromethyl)aniline in step 5) of Example 8. $^1$H NMR (400 MHz, DMSO-$d_6$) δ 8.45 (d, J=5.1 Hz, 1H), 8.17 (d, J=9.0 Hz, 1H), 7.90 (s, 1H), 7.24 (d, J=2.8 Hz, 1H), 7.18-6.99 (m, 3H), 6.53 (d, J=5.2 Hz, 1H), 4.39-4.25 (m, 4H), 4.20 (t, J=6.2 Hz, 2H), 2.69 (t, J=7.2 Hz, 2H), 2.61-2.55 (m, 1H), 2.18-2.06 (m, 2H), 0.70-0.59 (m, 2H), 0.48-0.36 (m, 2H). MS: 495[M+H]+.

Example 93

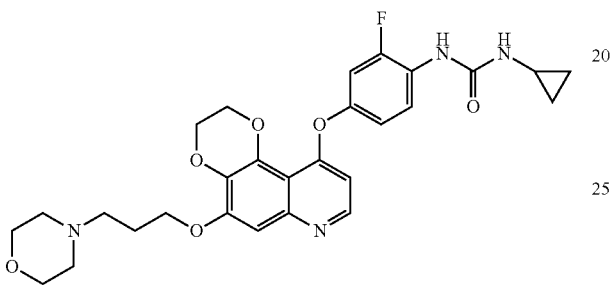

Example 94

Example 94: Preparation of 1-(4-chloro-3-(trifluoromethyl)phenyl)-3-(4-((5-(3-cyanopropoxy)-2,3-dihydro-[1,4]dioxino[2,3-f]quinolin-10-yl)oxy)phenyl)urea The preparation was carried out in a similar manner to Example 8, except that an equimolar equivalent of 4-bromobutyronitrile was used in place of 1-bromo-2-methoxyethane in step 2) of Example 8. $^1$H NMR (400 MHz, DMSO-$d_6$) δ 9.19 (s, 1H), 8.95 (s, 1H), 8.42 (d, J=5.2 Hz, 1H), 8.11 (d, J=2.5 Hz, 1H), 7.69-7.58 (m, 2H), 7.58-7.50 (m, 2H), 7.13-7.05 (m, 3H), 6.44 (d, J=5.2 Hz, 1H), 4.39-4.29 (m, 4H), 4.20 (t, J=6.2 Hz, 2H), 2.69 (t, J=7.2 Hz, 2H), 2.18-2.06 (m, 2H). MS: 599[M+H]+.

Example 95: Preparation of 1-(4-((5-methoxy-2,3-dihydro-[1,4]dioxino[2,3-f]quinolin-10-yl)oxy)phenyl)-3-(2-methyl-5-(trifluoromethyl)phenyl)urea The preparation was carried out in a similar manner to Example 1, except that an equimolar equivalent of 2-methyl-5-(trifluoromethyl)aniline was used in place of 4-chloro-3-(trifluoromethyl)aniline in step 3) of Example 1. $^1$H NMR (400 MHz, DMSO-$d_6$) δ 9.32 (s, 1H), 8.43 (d, J=5.2 Hz, 1H), 8.37 (d, J=1.9 Hz, 1H), 8.20 (s, 1H), 7.62-7.53 (m, 2H), 7.41 (d, J=7.9 Hz, 1H), 7.31-7.23 (m, 1H), 7.13-7.03 (m, 3H), 6.44 (d, J=5.3 Hz, 1H), 4.38-4.28 (m, 4H), 3.92 (s, 3H), 2.34 (s, 3H). MS: 526[M+H]+.

Example 95

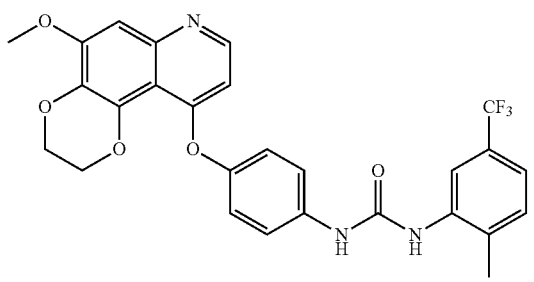

Example 96

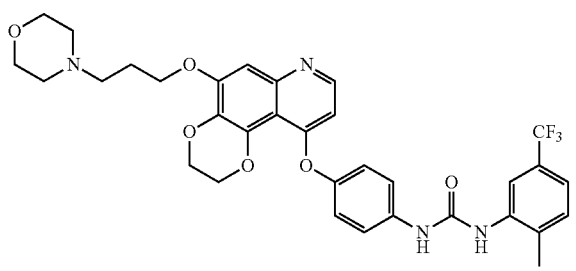

Example 96: Preparation of 1-(2-methyl-5-(trifluoromethyl)phenyl)-3-(4-((5-(3-morpholinopropoxy)-2,3-dihydro-[1,4]dioxino[2,3-f]quinolin-10-yl)oxy)phenyl)urea The preparation was carried out in a similar manner to Example 8, except that an equimolar equivalent of 4-(3-chloropropyl)morpholine hydrochloride was used in place of 1-bromo-2-methoxyethane in step 2) of Example 8, and an equimolar equivalent of 2-methyl-5-(trifluoromethyl)aniline was used in place of 4-chloro-3-(trifluoromethyl)aniline in step 5) of Example 8. $^1$H NMR (600 MHz, DMSO-d$_6$) δ 9.30 (s, 1H), 8.41 (d, J=5.2 Hz, 1H), 8.37 (d, J=1.9 Hz, 1H), 8.19 (s, 1H), 7.60-7.53 (m, 2H), 7.41 (d, J=7.9 Hz, 1H), 7.27 (dd, J=7.9, 1.8 Hz, 1H), 7.12-7.06 (m, 2H), 7.05 (s, 1H), 6.43 (d, J=5.2 Hz, 1H), 4.38-4.29 (m, 4H), 4.17 (t, J=6.4 Hz, 2H), 3.59 (t, J=4.5 Hz, 4H), 2.46 (t, J=7.1 Hz, 2H), 2.39 (s, 4H), 2.34 (s, 3H), 2.01-1.92 (m, 2H). MS: 639[M+H]$^+$.

Biological Example 1. Assay of Small Molecular Compounds for Inhibiting the Activity of RET Kinase The assay is based on the LANCE TR-FRET technology of Perkin Elmer Inc., and the assay method is as follows:
1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).
2. 2.5 μL of the gradient-diluted compounds were taken with a transfer pipette to a 384-well plate.
3. Addition of enzyme: 5 μL of 2× RET kinase solution (concentration was 0.8 nM) was taken with a transfer pipette to the corresponding reaction well of the 384-well plate, mixed well and pre-reacted at room temperature for 30 minutes.
4. 2.5 μL 4× Ultra ULight™-JAK-1 (Tyr1023) Peptide (concentration was 200 nM)/ATP (concentration was 40 μM) mixture was taken with a transfer pipette to the corresponding reaction well of the 384-well plate.
5. Negative control: 2.5 μL/well 4× substrate/ATP mixture and 7.5 μL 1× Kinase Assay Buffer were added to the wells of the 384-well plate.
Positive control: 2.5 μL/well 4× substrate/ATP mixture, 2.5 μL/well 1× Kinase Assay Buffer containing 16% DMSO, and 5 μL/well 2× RET kinase solution were added to the 384-well plate. The final concentration of DMSO in the reaction system was 4%.
6. The mixture was mixed well and then centrifuged and reacted at room temperature in dark for 60 min.
7. Termination of the enzymatic reaction: 5 μL of 4× stop solution was taken with a transfer pipette to the wells of the 384-well plate, mixed and then centrifuged, and reacted at room temperature for 5 min.
8. Development of the reaction: 5 μL of 4× detection solution was taken with a transfer pipette to the wells of the 384-well plate for color development, and the mixture was mixed and then centrifuged and reacted at room temperature for 60 min.
9. The 384-well plate was placed into the Envision plate reader and the signal was detected using the appropriate program.
10. Analysis and processing of the raw data:
The drug concentrations and the corresponding inhibition rates were input into GraphPad Prism5 for calculation, and the inhibition rate of the compounds were calculated as follows: inhibition rate (%)=(reading of positive well−reading of experimental well)/(reading of positive control well−reading of negative control well)×100%. Processing with GraphPad Prism5 software yielded the corresponding IC$_{50}$ values (the concentration of the compound at which 50% of the highest inhibition of the enzyme is achieved).
Table 1 lists the assay results of the inhibitory activity of the compounds disclosed herein on the RET tyrosine kinase, wherein A indicates that the IC$_{50}$ is less than or equal to 50 nM, B indicates that the IC$_{50}$ is greater than 50 nM but less than or equal to 500 nM, C indicates that the IC$_{50}$ is greater than 500 nM but less than or equal to 5000 nM, and D indicates that the IC$_{50}$ is greater than 5000 nM.

TABLE 1

Assay results of the inhibitory activity of the compounds disclosed herein on the RET tyrosine kinase

| Example No. | RET IC$_{50}$ (nM) |
|---|---|
| 1 | A |
| 2 | A |
| 3 | B |
| 4 | B |
| 5 | A |
| 6 | A |
| 7 | A |
| 8 | A |
| 9 | B |
| 10 | B |
| 11 | C |
| 12 | B |
| 13 | B |
| 14 | A |
| 15 | B |
| 16 | B |
| 17 | A |
| 18 | A |
| 19 | A |
| 20 | B |
| 21 | A |

TABLE 1-continued

Assay results of the inhibitory activity of the compounds disclosed herein on the RET tyrosine kinase

| Example No. | RET IC$_{50}$ (nM) |
| --- | --- |
| 22 | A |
| 23 | B |
| 24 | A |
| 25 | A |
| 26 | A |
| 27 | A |
| 28 | A |
| 29 | A |
| 30 | A |
| 31 | B |
| 32 | B |
| 33 | B |
| 34 | A |
| 35 | A |
| 36 | A |
| 37 | A |
| 38 | B |
| 39 | B |
| 40 | A |
| 41 | B |
| 42 | A |
| 43 | A |
| 44 | A |
| 45 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | A |
| 69 | A |
| 70 | A |
| 71 | A |
| 72 | A |
| 73 | B |
| 74 | A |
| 75 | A |
| 76 | A |
| 77 | A |
| 78 | A |
| 79 | A |
| 80 | A |
| 81 | A |
| 82 | A |
| 83 | B |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |

Biological Example 2. Assay of Small Molecular Compounds for Inhibiting the Activity of VEGFR-2 Kinase The assay is based on the LANCE TR-FRET technology of Perkin Elmer Inc., and the assay method is as follows:

1. Dilution of compounds: a total of 11 concentrations were obtained using a 3-fold gradient dilution from the highest concentration of 2500 nM (the maximum final concentration of the drug used in this assay was 2500 nM, and the minimum final concentration was 0.042 nM).

2. 2.5 μL of the gradient-diluted compounds were taken with a transfer pipette to a 384-well plate.

3. Addition of enzyme: 5 μL of 2× VEGFR2 kinase solution (concentration was 0.5 nM) was taken with a transfer pipette to the corresponding reaction well of the 384-well plate, mixed well and pre-reacted at room temperature for 30 minutes.

4. 2.5 μL 4× Ultra ULight™-JAK-1 (Tyr1023) Peptide (concentration was 200 nM)/ATP (concentration was 40 μMM) mixture was taken with a transfer pipette to the corresponding reaction well of the 384-well plate.

5. Negative control: 2.5 μL/well 4× substrate/ATP mixture and 7.5 μL 1× Kinase Assay Buffer were added to the wells of the 384-well plate.

6. Positive control: 2.5 μL/well 4× substrate/ATP mixture, 2.5 μL/well 1× Kinase Assay Buffer containing 16% DMSO, and 5 μL/well 2× VEGFR2 kinase solution were added to the 384-well plate. The final concentration of DMSO in the reaction system was 4%.

7. The mixture was mixed well and then centrifuged and reacted at room temperature in dark for 60 min.

8. Termination of the enzymatic reaction: 5 μL of 4× stop solution was taken with a transfer pipette to the wells of the 384-well plate, mixed and then centrifuged, and reacted at room temperature for 5 min.

9. Development of the reaction: 5 μL of 4× detection solution was taken with a transfer pipette to the wells of the 384-well plate for color development, and the mixture was mixed and then centrifuged and reacted at room temperature for 60 min.

10. The 384-well plate was placed into the Envision plate reader and the signal was detected using the appropriate program.

11. Analysis and processing of the raw data:
The drug concentrations and the corresponding inhibition rates were input into GraphPad Prism5 for calculation, and the inhibition rate of the compounds were calculated as follows: inhibition rate (%)=(reading of positive well−reading of experimental well)/(reading of positive control well−reading of negative control well)×100%. Processing with GraphPad Prism5 software yielded the corresponding IC$_{50}$ values (the concentration of the compound at which 50% of the highest inhibition of the enzyme is achieved).

Table 2 lists the assay results of the inhibitory activity of some of the compounds disclosed herein on the VEGFR2 tyrosine kinase, wherein A indicates that the $IC_{50}$ is less than or equal to 50 nM, B indicates that the $IC_{50}$ is greater than 50 nM but less than or equal to 500 nM, C indicates that the $IC_{50}$ is greater than 500 nM but less than or equal to 5000 nM, and D indicates that the $IC_{50}$ is greater than 5000 nM.

TABLE 2

Assay results of the inhibitory activity of some of the compounds disclosed herein on the VEGFR2 tyrosine kinase

| Example No. | VEGFR-2 $IC_{50}$ (nM) |
|---|---|
| 1 | A |
| 5 | B |
| 6 | B |
| 7 | A |
| 8 | B |
| 9 | B |
| 14 | A |
| 17 | A |
| 18 | A |
| 19 | A |
| 21 | A |
| 25 | A |
| 26 | A |
| 27 | B |
| 28 | A |
| 30 | B |
| 36 | B |
| 43 | A |
| 46 | A |
| 47 | A |
| 48 | A |
| 49 | A |
| 50 | A |
| 51 | A |
| 52 | A |
| 53 | A |
| 54 | A |
| 55 | A |
| 56 | A |
| 57 | A |
| 58 | A |
| 59 | A |
| 60 | A |
| 61 | A |
| 62 | A |
| 63 | A |
| 64 | A |
| 66 | A |
| 70 | A |
| 72 | A |
| 74 | A |
| 77 | A |
| 78 | A |
| 79 | A |
| 80 | A |
| 81 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | B |
| 95 | A |
| 96 | B |

The biological data provided by the present disclosure indicate that the compounds disclosed herein are useful for treating or preventing diseases caused by abnormalities of VEGFR-2 and RET kinase. Therefore, the compounds disclosed herein are useful in the treatment of cancer, including primary and metastatic cancers, including solid tumors. Such cancers include, but are not limited to, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic granulocytic leukemia, acute myeloid leukemia, non-Hodgkin's lymphoma, nasopharyngeal carcinoma, esophageal cancer, brain tumor, B-cell and T-cell lymphoma, lymphoma, multiple myeloma, biliary cancer and sarcoma, and cholangiocarcinoma. The compounds disclosed herein also treat cancers that are resistant to one or more other therapeutic methods. The compounds disclosed herein can also be used for other diseases (besides cancer) related to VEGFR-2 kinase and/or RET kinase, including but not limited to ocular fundus diseases, psoriasis, rheumatic arthritis, atherosclerosis, pulmonary fibrosis, and liver fibrosis. The compounds disclosed herein can be used as monotherapy or combination therapy, and can be used in combination with multiple compounds disclosed herein or in combination with other drugs than the present disclosure.

The above-mentioned embodiments are only preferred embodiments of the present disclosure and are not intended to limit the present disclosure. Any modification, equivalent replacement and improvement made within the spirit and principle of the present disclosure should be included within the protection scope of the present disclosure.

What is claimed is:
1. A compound represented by formula (I), or a pharmaceutically acceptable salt, an enantiomer, a diastereomer, a hydrate, or a solvate thereof,

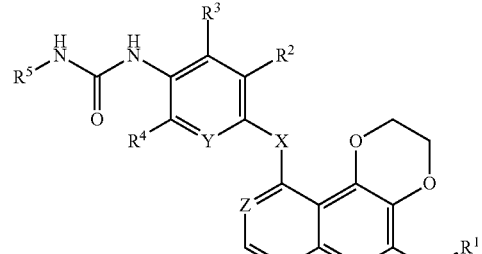

Formula (I)

in the formula (I),
X is O or NH;
Y is CH;
Z is CH;
$R^1$ is H, $C_1$-$C_9$ alkyl, $C_3$-$C_7$ cycloalkyl, 4- to 7-membered heterocyclyl, $C_1$-$C_6$ alkyl substituted with $C_3$-$C_7$ cycloalkyl, $C_1$-$C_6$ alkyl substituted with 4- to 7-membered heterocyclyl, or $C_1$-$C_9$ alkyl substituted with one or more of the following: hydroxyl, $C_1$-$C_6$ alkoxy, $C_1$-$C_6$ alkylthio, amino substituted with mono- or di-$C_1$-$C_6$ alkyl or unsubstituted amino,
the above 4- to 7-membered heterocyclyl is a 4- to 7-membered heterocyclyl containing 1 to 2 atoms selected from the group consisting of N, O, and S, which is unsubstituted, or substituted with $C_1$-$C_6$ alkyl, or $C_1$-$C_3$ acyl, or is oxidized by 1 to 2 oxygen atoms;
$R^2$ is H or halogen;
$R^3$ is H or halogen;
$R^4$ is H or halogen;

R⁵ is H, $C_1$-$C_9$ alkyl, $C_3$-$C_8$ cycloalkyl, $C_1$-$C_6$ alkyl substituted with $C_3$-$C_8$ cycloalkyl, unsubstituted aryl or heteroaryl, or an aryl or heteroaryl group substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, unsubstituted amino, halogen, trifluoromethyl, aryloxy and methylsulfonyl; and the heteroaryl group is a monocyclic or bicyclic group containing 5 to 10 ring atoms, which contains 1 to 3 atoms selected from the group consisting of N, O, and S in the ring.

2. The compound, or the pharmaceutically acceptable salt, the enantiomer, the diastereomer, the hydrate, or the solvate thereof according to claim 1, wherein $R^1$ is H, $C_1$-$C_6$ alkyl, $C_3$-$C_6$ cycloalkyl, 5- to 6-membered heterocyclyl, $C_1$-$C_3$ alkyl substituted with $C_3$-$C_6$ cycloalkyl, $C_1$-$C_3$ alkyl substituted with 5- to 6-membered heterocyclyl, or $C_1$-$C_6$ alkyl substituted with one or more of the following: hydroxyl, $C_1$-$C_3$ alkoxy, $C_1$-$C_3$ alkylthio, amino substituted with mono- or di-$C_1$-$C_3$ alkyl, or unsubstituted amino, and the above 5- to 6-membered heterocyclyl is a 5- to 6-membered heterocyclyl containing 1 to 2 atoms selected from the group consisting of N, O, and S, which is unsubstituted, or substituted with $C_1$-$C_3$ alkyl, or $C_1$-$C_3$ acyl, or is oxidized by 1 to 2 oxygen atoms.

3. The compound, or the pharmaceutically acceptable salt, the enantiomer, the diastereomer, the hydrate, or the solvate thereof according to claim 2, wherein $R^1$ is selected from the group consisting of H, methyl, ethyl, propyl, isopropyl, methoxyethyl, methoxypropyl, methoxybutyl, methoxypentyl, methoxyhexyl, tetrahydrofuran-3-yl, tetrahydro-2H-pyran-4-yl, tetrahydropyrrol-1-ylethyl, tetrahydropyrrol-1-ylpropyl, piperidin-1-ylethyl, piperidin-1-ylpropyl, piperazin-1-ylethyl, piperazin-1-ylpropyl, morpholin-4-ylethyl, morpholin-4-ylpropyl, methylpiperazin-4-ylethyl, methylpiperazin-4-ylpropyl, N-formylpiperazin-4-ylethyl, N-formylpiperazin-4-ylpropyl, N-acetylpiperazin-4-ylethyl, N-acetylpiperazin-4-ylpropyl, (1,1-dioxothiomorpholin)-4-ylethyl, (1,1-dioxothiomorpholin)-4-ylpropyl, methylthioethyl, methylthiopropyl, dimethylaminoethyl, dimethylaminopropyl, dimethylaminobutyl, diethylaminoethyl, diethylaminopropyl, hydroxyethyl, hydroxypropyl, hydroxybutyl, hydroxypentyl, hydroxyhexyl, aminoethyl, aminopropyl, aminobutyl, 2-methyl-2-hydroxypropyl, 3-methyl-3-hydroxybutyl, (3S)-3-aminobutyl, (3R)-3-aminobutyl, (3S)-3-hydroxybutyl and (3R)-3-hydroxybutyl.

4. The compound, or the pharmaceutically acceptable salt, the enantiomer, the diastereomer, the hydrate, or the solvate thereof according to claim 1, wherein $R^1$ is selected from the group consisting of butyl, isobutyl, pentyl, isopentyl, hexyl, cyclopropylmethyl, cyclopropylethyl, cyclopropylpropyl, cyclobutylmethyl, cyclobutylethyl, cyclobutylpropyl, 4,4-dimethylpiperidin-1-ylethyl, 4,4-dimethylpiperidin-1-ylpropyl, dimethylaminopentyl, dimethylaminohexyl, and oxetan-3-yl.

5. The compound, or the pharmaceutically acceptable salt, the enantiomer, the diastereomer, the hydrate, or the solvate thereof according to claim 1, wherein the halogen in $R^2$, $R^3$, and $R^4$ is F, Cl or Br.

6. The compound, or the pharmaceutically acceptable salt, the enantiomer, the diastereomer, the hydrate, or the solvate thereof according to claim 1, wherein $R^5$ is H, $C_1$-$C_6$ alkyl, $C_3$-$C_6$ cycloalkyl, $C_1$-$C_3$ alkyl substituted with $C_3$-$C_6$ cycloalkyl, unsubstituted aryl or heteroaryl, or an aryl or heteroaryl group substituted with one or more of the following: $C_1$-$C_3$ alkyl, $C_1$-$C_3$ alkoxy, $C_1$-$C_3$ alkylthio, amino substituted with mono- or di-$C_1$-$C_3$ alkyl, unsubstituted amino, halogen, trifluoromethyl, aryloxy or methylsulfonyl; and the heteroaryl group is a monocyclic or bicyclic group containing 5 to 10 ring atoms, which contains 1 to 2 atoms selected from the group consisting of N, O, and S in the ring.

7. The compound, or the pharmaceutically acceptable salt, the enantiomer, the diastereomer, the hydrate, or the solvate thereof according to claim 1, wherein $R^5$ is H, $C_1$-$C_6$ alkyl, $C_3$-$C_6$ cycloalkyl, $C_1$-$C_3$ alkyl substituted with $C_3$-$C_6$ cycloalkyl, unsubstituted phenyl, naphthyl or heteroaryl, or a phenyl, naphthyl or heteroaryl group substituted with one or more of the following: methyl, ethyl, propyl, isopropyl, methoxy, ethoxy, propoxy, isopropoxy, methylthio, ethylthio, propylthio, isopropylthio, amino, methylamino, ethylamino, dimethylamino, diethylamino, fluorine, chlorine, bromine, trifluoromethyl, phenoxy or methylsulfonyl; and the heteroaryl group is selected from the group consisting of pyridinyl, pyrimidinyl, quinolinyl, quinazolinyl, oxazolyl, isoxazolyl, thiazolyl, thiadiazolyl, pyrazolyl, imidazolyl, and pyrrolyl.

8. The compound, or the pharmaceutically acceptable salt, the enantiomer, the diastereomer, the hydrate, or the solvate thereof according to claim 1, wherein $R^5$ is selected from the group consisting of H, methyl, ethyl, propyl, isopropyl, isopenyl, cyclopropyl, cyclobutyl, cyclopentyl, cyclohexyl, phenyl, 2-methoxyphenyl, 3-methoxyphenyl, 4-methoxyphenyl, 2-fluorophenyl, 3-fluorophenyl, 4-fluorophenyl, 4-phenoxyphenyl, 3-(methyl sulfonyl)phenyl, 4-(methyl sulfonyl)phenyl, 2,4-difluorophenyl, 2,5-difluorophenyl, 3,4-difluorophenyl, 2,4-dichlorophenyl, 2,5-dichlorophenyl, 3,4-dichlorophenyl, 2-fluoro-4-(trifluoromethyl)phenyl, 2-fluoro-5-(trifluoromethyl)phenyl, 3-fluoro-4-(trifluoromethyl)phenyl, 3-fluoro-5-(trifluoromethyl)phenyl, 3-(trifluoromethyl)-4-fluorophenyl, 2-fluoro-4-chlorophenyl, 2-fluoro-5-chlorophenyl, 3-fluoro-4-chlorophenyl, 3-fluoro-5-chlorophenyl, 3-chloro-4-fluorophenyl, 2-chloro-4-(trifluoromethyl)phenyl, 2-chloro-5-(trifluoromethyl)phenyl, 3-chloro-4-(trifluoromethyl)phenyl, 3-chloro-5-(trifluoromethyl)phenyl, 3-(trifluoromethyl)-4-chlorophenyl, 2-chloro-4-fluorophenyl, 2-chloro-5-fluorophenyl, 3-chloro-4-fluorophenyl, pyridin-2-yl, pyridin-3-yl, pyridin-4-yl, 2-methoxypyridin-4-yl, 3-methyl-isoxazol-5-yl, and naphthalen-1-yl.

9. The compound, or the pharmaceutically acceptable salt, the enantiomer, the diastereomer, the hydrate, or the solvate thereof according to claim 1, wherein $R^5$ is selected from the group consisting of butyl, isobutyl, 2-methylphenyl, 3-methylphenyl, 4-methylphenyl, 2-methyl-5-(trifluoromethyl)phenyl, 2-methyl-4-(trifluoromethyl)phenyl, 3-methyl-4-(trifluoromethyl)phenyl, 3-methyl-5-(trifluoromethyl)phenyl, 2-chloro-4-methylphenyl, 2-chloro-5-methylphenyl, and 3-chloro-4-methylphenyl.

10. A compound represented by formula (I), or a pharmaceutically acceptable salt, an enantiomer, a diastereomer, a hydrate, or a solvate thereof, Formula (I)

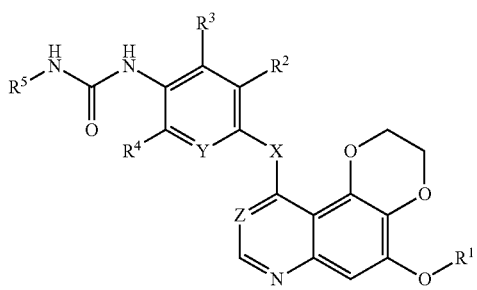

in the formula (I),
X is O or NH;
Y is CH;
Z is CH;
$R^1$ is $C_1$-$C_6$ alkyl substituted with 1 to 3 substituents selected from the group consisting of $C_1$-$C_3$ acyl, halogen, trifluoromethyl, cyano, —$CONH_2$, —$NR^a R^b$ and 4- to 7-membered heteroalicyclic group, wherein the 4- to 7-membered heteroalicyclic group is a 4- to 7-membered heteroalicyclic group containing 1 to 2 atoms selected from the group consisting of N, O, and S as ring atoms, and the 4- to 7-membered heteroalicyclic group is substituted with 1 to 3 substituents selected from the group consisting of halogen, $C_1$-$C_3$ alkyl, hydroxyl, —$NH_2$, and $C_1$-$C_3$ acyl,
$R^a$ and $R^b$ are each independently H, $C_1$-$C_6$ alkyl, $C_3$-$C_6$ cycloalkyl, $C_1$-$C_6$ alkyl substituted with $C_1$-$C_3$ alkoxy, $C_1$-$C_6$ alkyl substituted with $C_1$-$C_3$ alkylthio, or $C_1$-$C_6$ alkyl substituted with substituted amino or unsubstituted amino, wherein the substituted amino is substituted with mono- or di-$C_1$-$C_3$ alkyl;
$R^2$, $R^3$, and $R^4$ are each independently H or halogen;
$R^5$ is H, $C_1$-$C_9$ alkyl, $C_3$-$C_8$ cycloalkyl, $C_1$-$C_6$ alkyl substituted with $C_3$-$C_8$ cycloalkyl, unsubstituted aryl or heteroaryl, or an aryl or heteroaryl group substituted with 1 to 3 substituents —B, wherein the substituents —B are each independently hydroxyl, cyano, $C_1$-$C_3$ alkyl, $C_1$-$C_3$ alkoxy, $C_1$-$C_3$ alkylthio, amino substituted with mono- or di-$C_1$-$C_3$ alkyl, unsubstituted amino, halogen, trifluoromethyl, aryloxy or methylsulfonyl; and
the heteroaryl group is a monocyclic or bicyclic group containing 5 to 10 ring atoms, which contains 1 to 3 atoms selected from the group consisting of N, O, and S in the ring.

11. The compound, or the pharmaceutically acceptable salt, the enantiomer, the diastereomer, the hydrate, or the solvate thereof according to claim 10, wherein $R^1$ is $C_1$-$C_6$ alkyl substituted with 1 to 3 substituents selected from the group consisting of —F, trifluoromethyl, cyano, —$CONH_2$, —$NR^a R^b$, and 4- to 7-membered heteroalicyclic group, wherein the 4- to 7-membered heteroalicyclic group contains 1 to 2 atoms selected from the group consisting of N, O, and S as ring atoms, and the 4- to 7-membered heteroalicyclic group is substituted with 1 to 3 substituents selected from the group consisting of —F, $C_1$-$C_3$ alkyl, hydroxyl, —$NH_2$, and $C_1$-$C_3$ acyl,
$R^a$ and $R^b$ are each independently H, $C_1$-$C_3$ alkyl, $C_3$-$C_6$ cycloalkyl, $C_1$-$C_3$ alkyl substituted with $C_1$-$C_3$ alkoxy, $C_1$-$C_3$ alkyl substituted with $C_1$-$C_3$ alkylthio, or $C_1$-$C_3$ alkyl substituted with substituted amino or unsubstituted amino, wherein the substituted amino is substituted with mono- or di-$C_1$-$C_3$ alkyl;
$R^5$ is H, $C_1$-$C_6$ alkyl, $C_3$-$C_6$ cycloalkyl, $C_1$-$C_3$ alkyl substituted with $C_3$-$C_6$ cycloalkyl, unsubstituted phenyl, naphthyl or heteroaryl; or a phenyl, naphthyl or heteroaryl group substituted with 1 to 3 substituents —B, wherein the substituents —B are each independently methyl, ethyl, propyl, isopropyl, methoxy, ethoxy, propoxy, isopropoxy, methylthio, ethylthio, propylthio, isopropylthio, amino, methylamino, ethylamino, dimethylamino, diethylamino, fluorine, chlorine, bromine, trifluoromethyl, phenoxy or methylsulfonyl; and
the heteroaryl group is selected from the group consisting of pyridinyl, pyrimidinyl, quinolinyl, quinazolinyl, oxazolyl, isoxazolyl, thiazolyl, thiadiazolyl, pyrazolyl, imidazolyl, and pyrrolyl.

12. A pharmaceutical composition, comprising the compound of Formula (I) or the pharmaceutically acceptable salt, the hydrate, or the solvate thereof according to claim 1 as an active ingredient, optionally one or more other therapeutic agents, and one or more pharmaceutically acceptable carriers or excipients.

13. A method of treating a disease in a subject, comprising administering to the subject the compound of Formula (I) or the pharmaceutically acceptable salt, the enantiomer, the diastereomer, the hydrate, or the solvate thereof according to claim 1, wherein the disease includes ocular fundus disease, psoriasis, rheumatic arthritis, atherosclerosis, pulmonary fibrosis, liver fibrosis, non-small cell lung cancer, small cell lung cancer, breast cancer, pancreatic cancer, glioma, glioblastoma, ovarian cancer, cervical cancer, colorectal cancer, melanoma, endometrial cancer, prostate cancer, bladder cancer, leukemia, gastric cancer, liver cancer, gastrointestinal stromal tumor, thyroid cancer, chronic myeloid leukemia, acute myeloid leukemia, non-Hodgkin's lymphoma, nasopharyngeal cancer, esophageal cancer, brain tumor, B-cell and T-cell lymphoma, lymphoma, multiple myeloma, biliary cancer and sarcoma, and cholangiocarcinoma.

14. The compound, or the pharmaceutically acceptable salt, the enantiomer, the diastereomer, the hydrate, or the solvate thereof according to claim 1, wherein:
X is O;
Y is CH;
Z is CH;
$R^1$ is $C_1$-$C_6$ alkyl
$R^2$ is H or halogen;
$R^3$ is H or halogen;
$R^4$ is H or halogen;
$R^5$ is an aryl group substituted with one or more of the following: $C_1$-$C_3$ alkyl, halogen, and trifluoromethyl.

15. The compound, or the pharmaceutically acceptable salt, the enantiomer, the diastereomer, the hydrate, or the solvate thereof according to claim 14, wherein: $R^1$ is methyl, ethyl, propyl, or isopropyl, and $R^5$ is a phenyl substituted with one or more of the following: methyl, ethyl, propyl, isopropyl, fluorine, chlorine, bromine, and trifluoromethyl.

16. The compound, or a pharmaceutically acceptable salt, an enantiomer, a diastereomer, a hydrate, or a solvate thereof according to claim 1, wherein the compound is selected from the group consisting of:

| 79 | 80 |
|---|---|
| 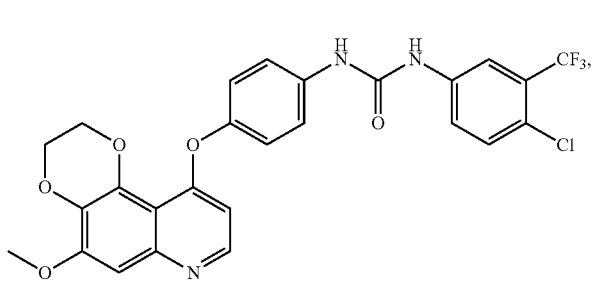 | 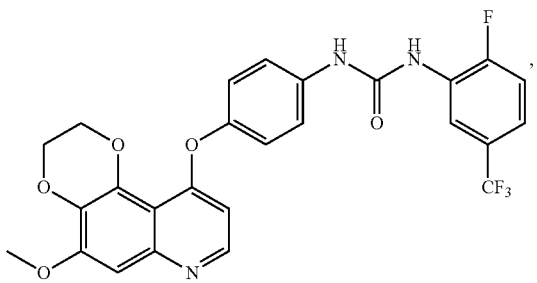 |
| 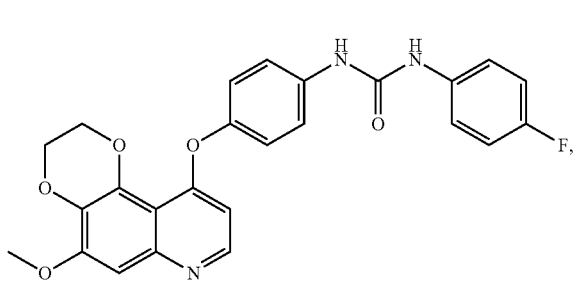 | 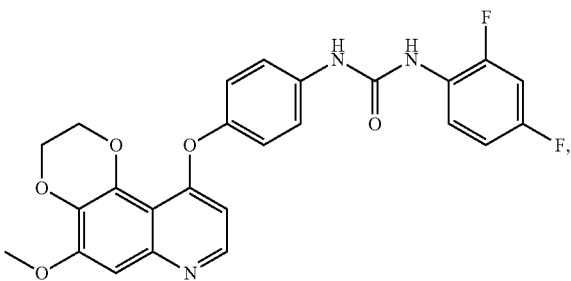 |
| 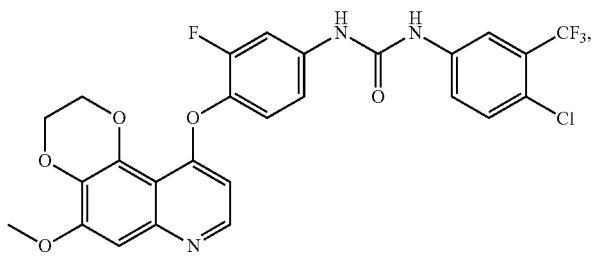 | 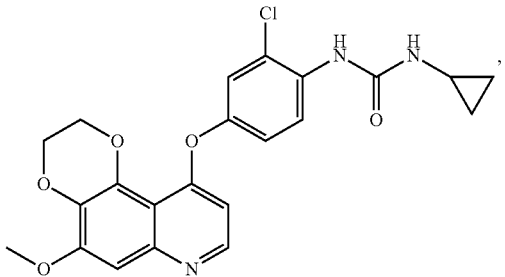 |
| 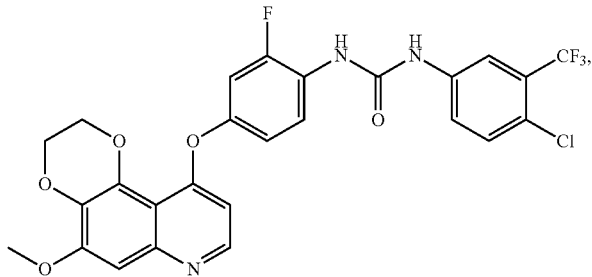 | |
| 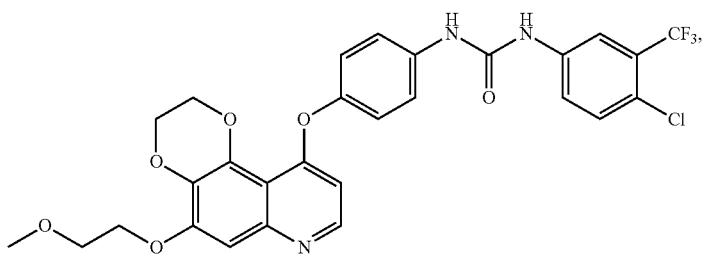 | |
| 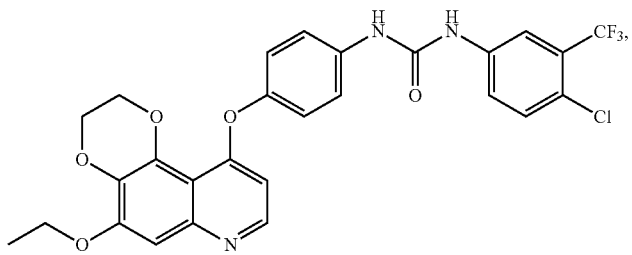 | |

-continued
| 81 | 82 |
|---|---|
| 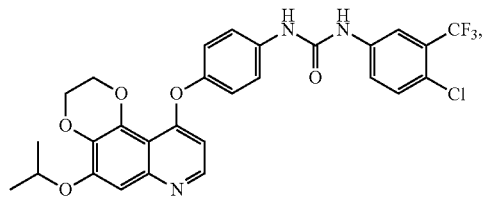 | 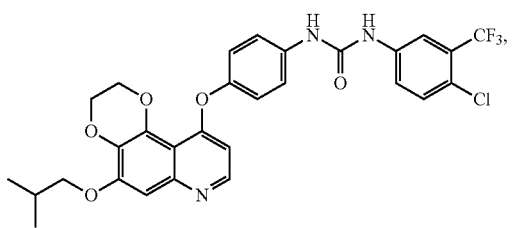 |
| 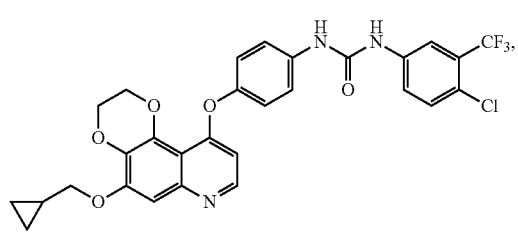 | 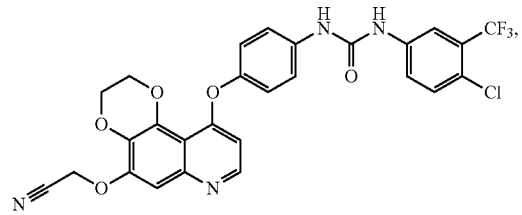 |
| 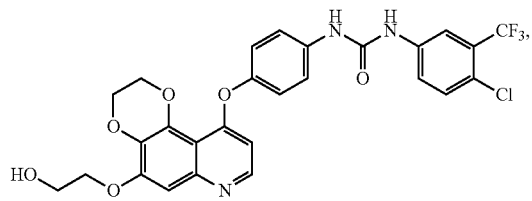 | 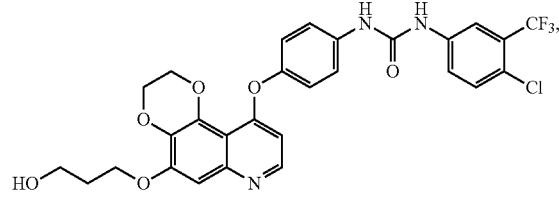 |
| 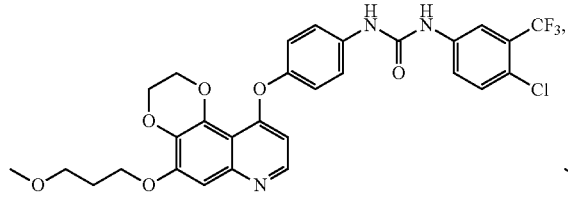 | 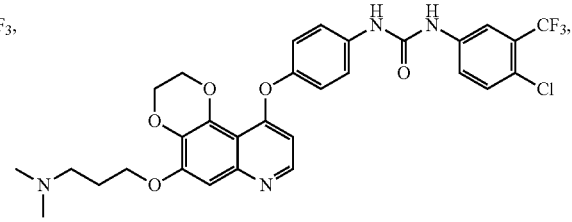 |
| 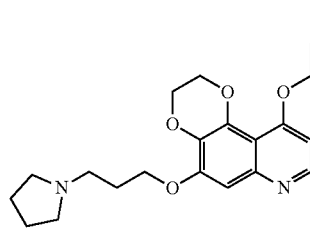 | 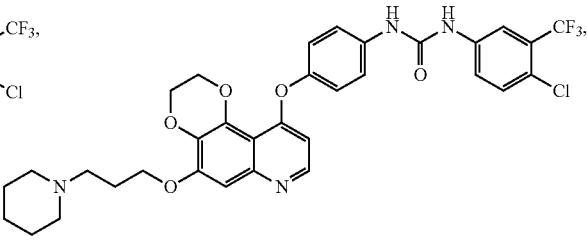 |
| 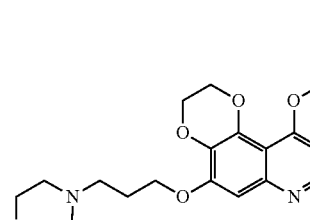 | 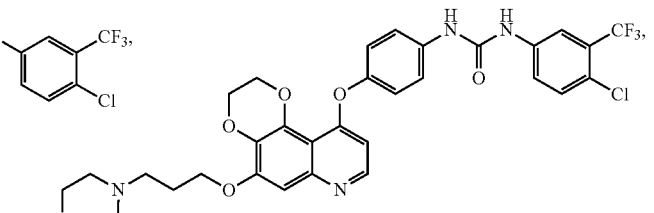 |
| 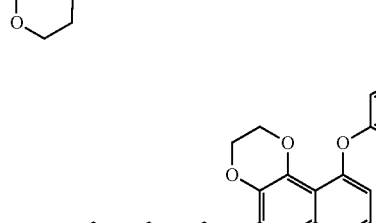 | 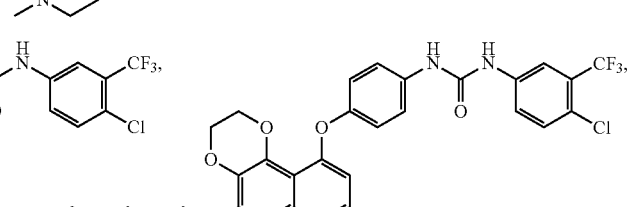 |
| 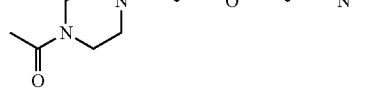 |  |

-continued
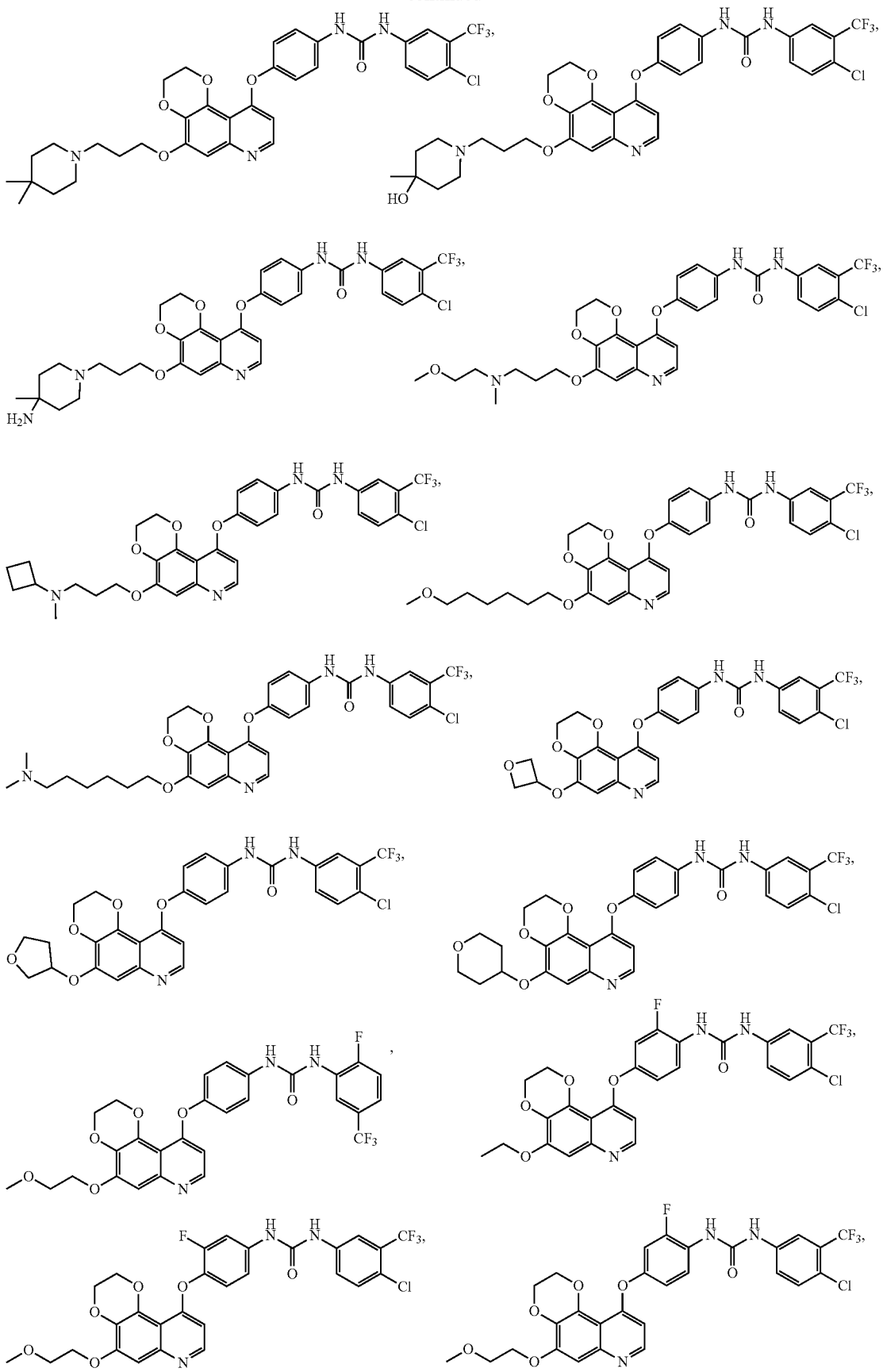

85 86
-continued
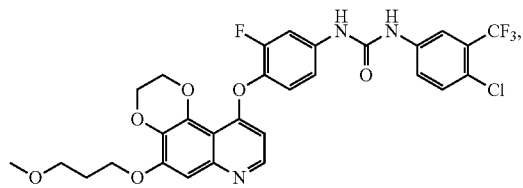
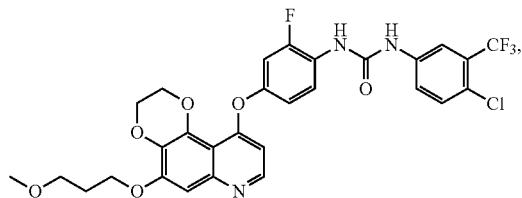
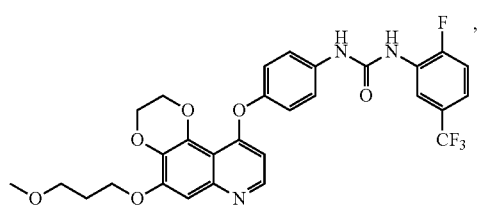
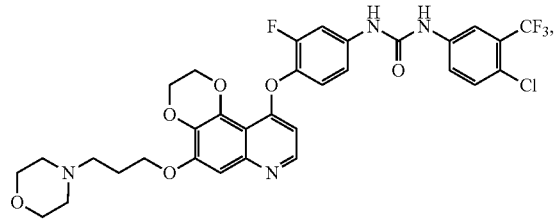
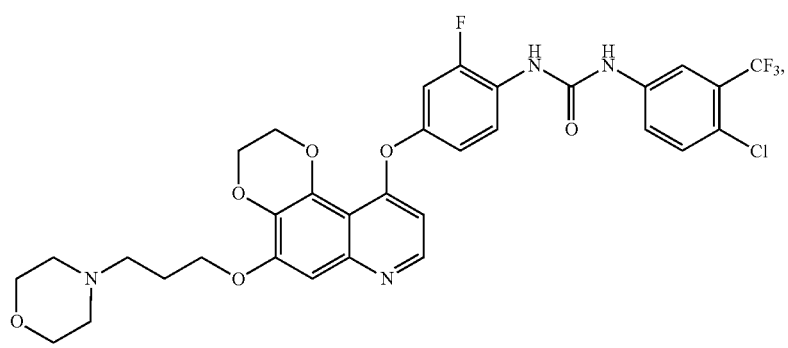
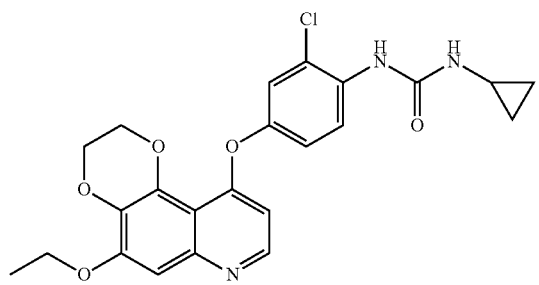
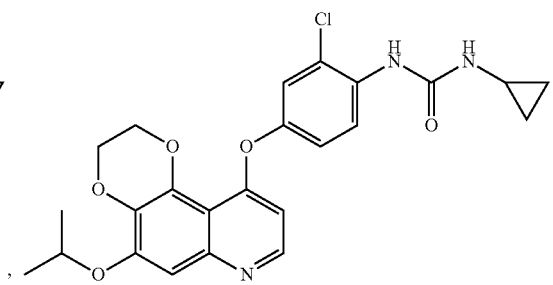
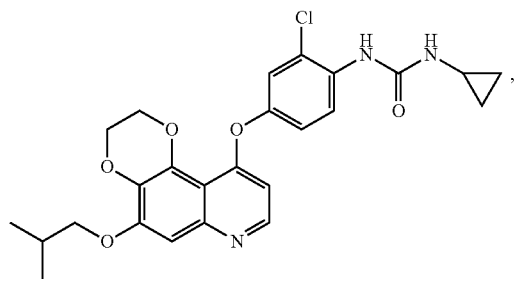
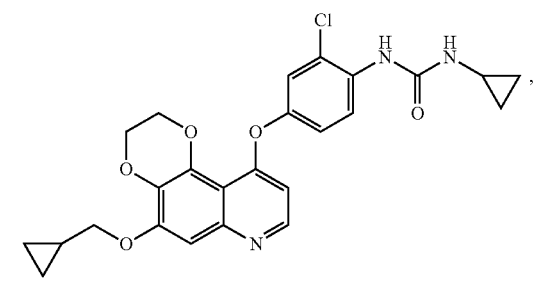
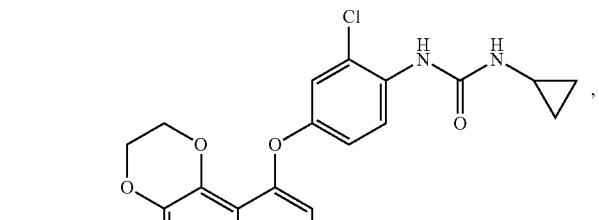
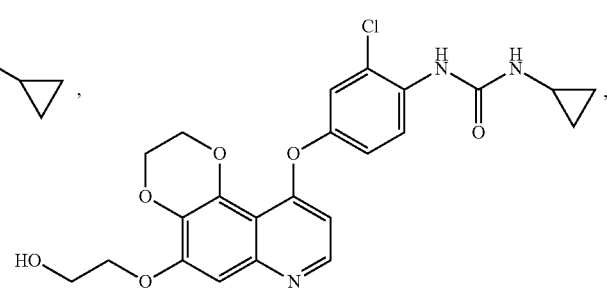

87
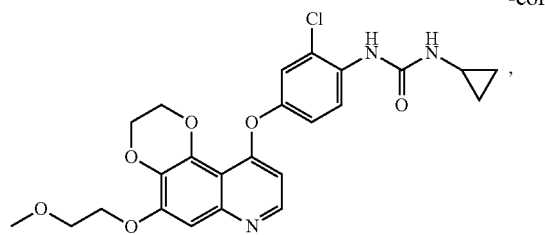
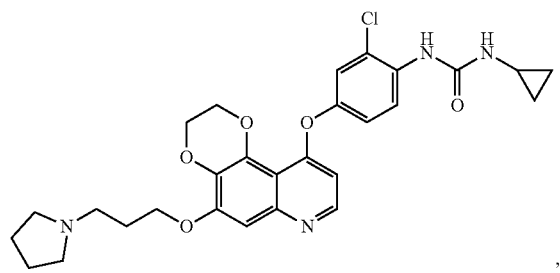
88
-continued
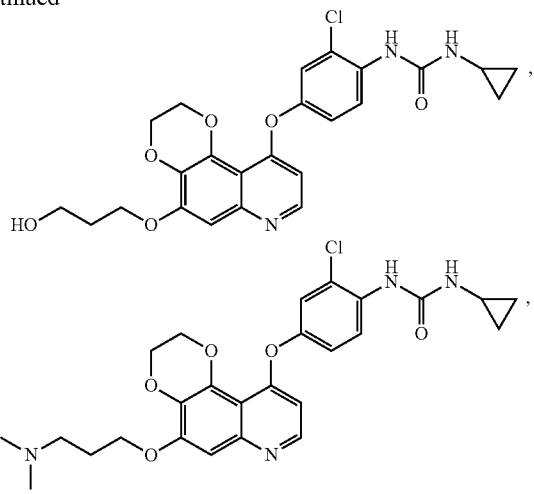
-continued
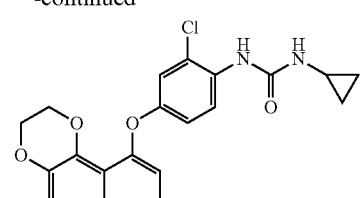
,
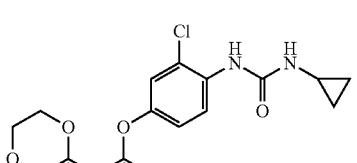
,
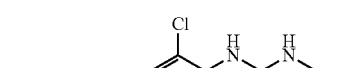
,
,

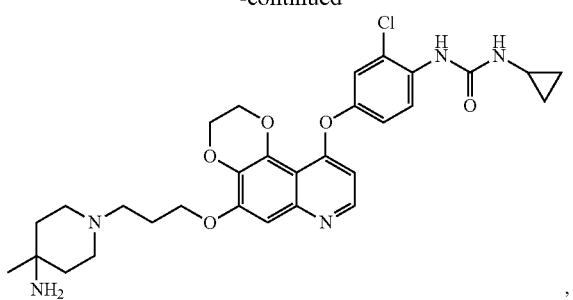
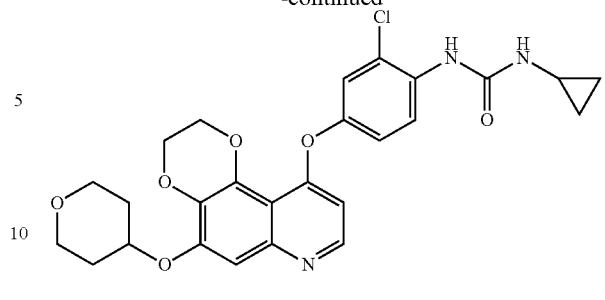
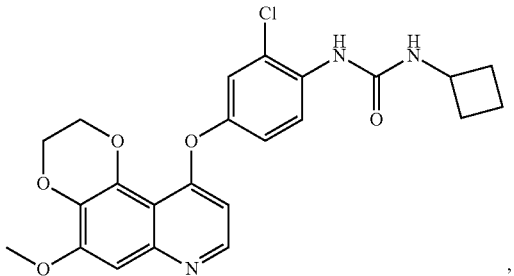
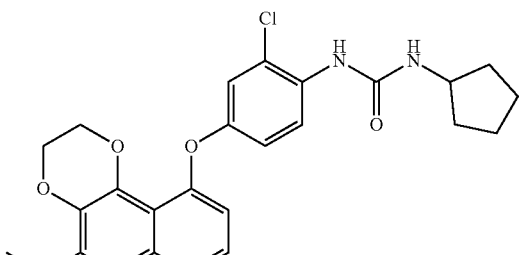
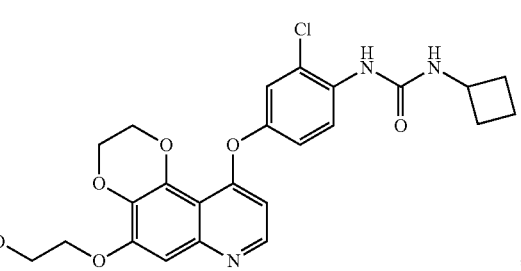
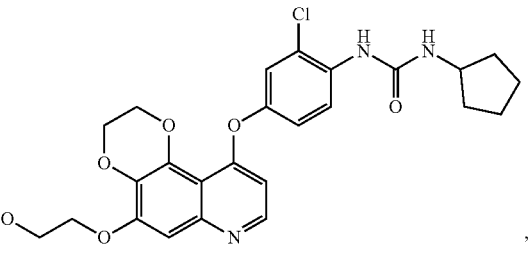
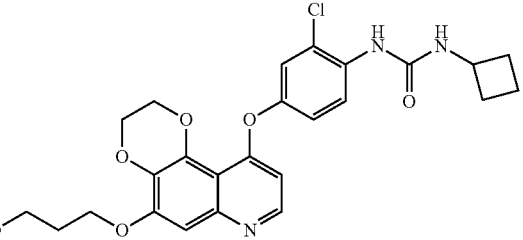

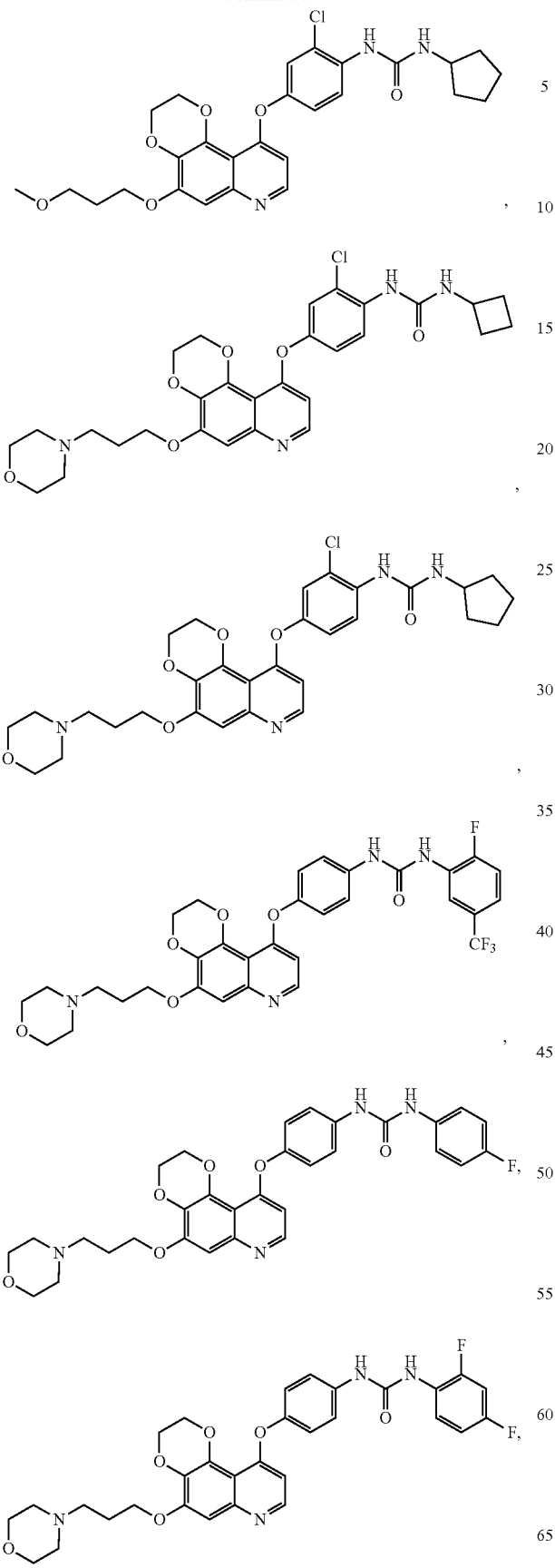
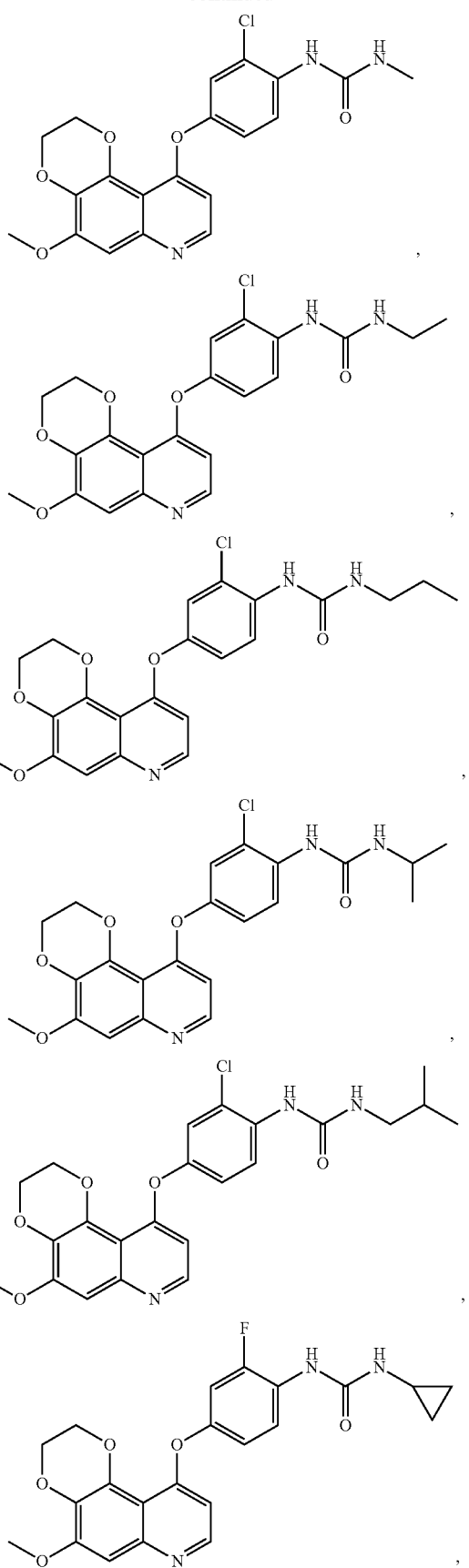

93
-continued
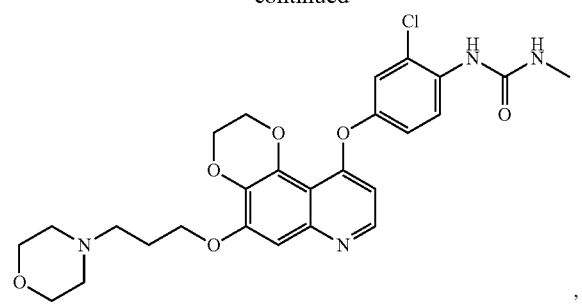
,
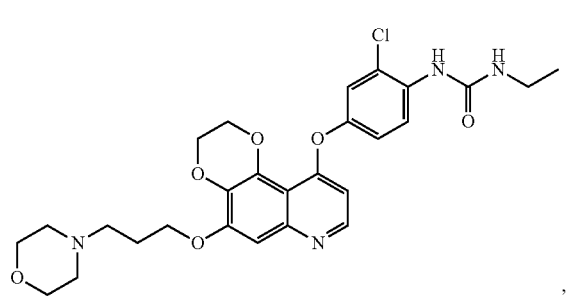
,
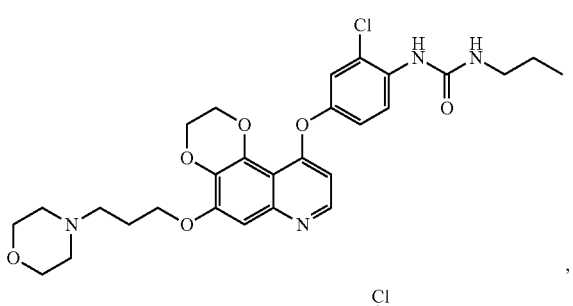
,
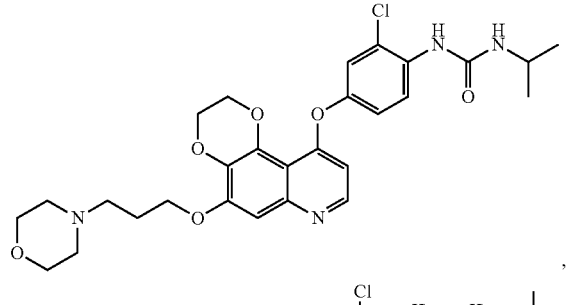
,
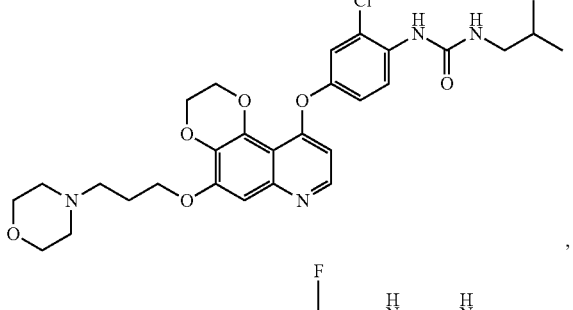
,
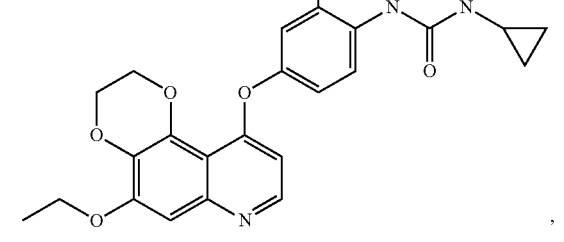
,
94
-continued
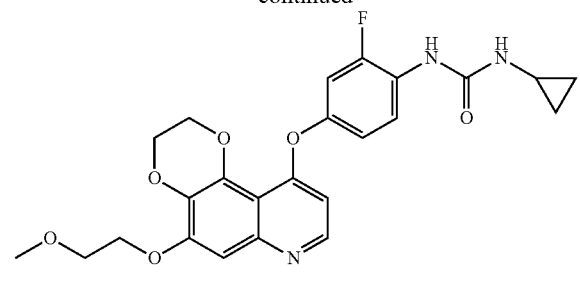
,
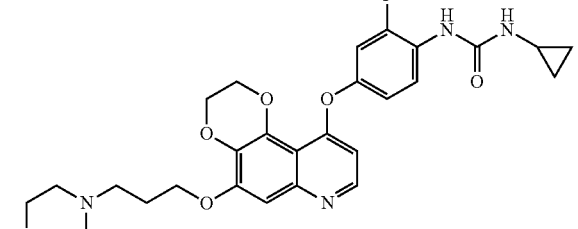
,
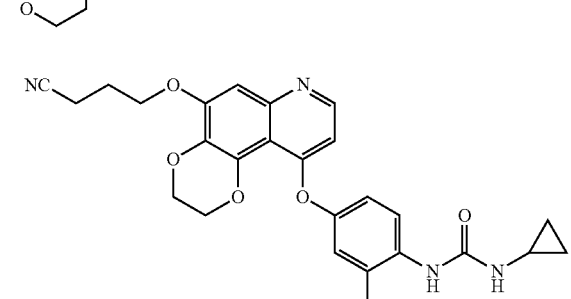
,
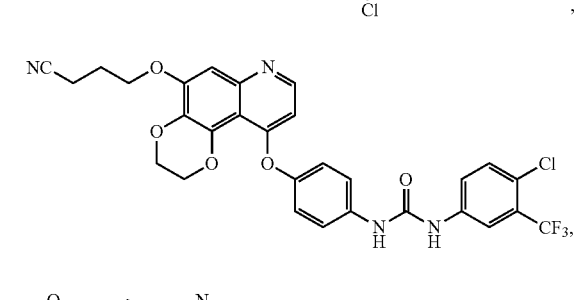
,
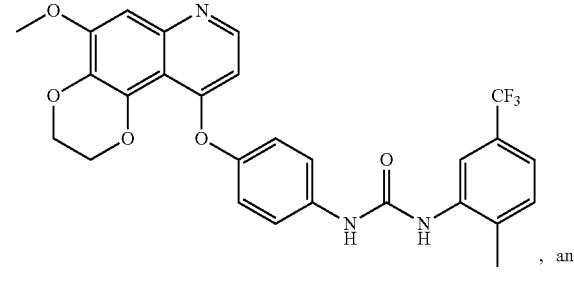
, and
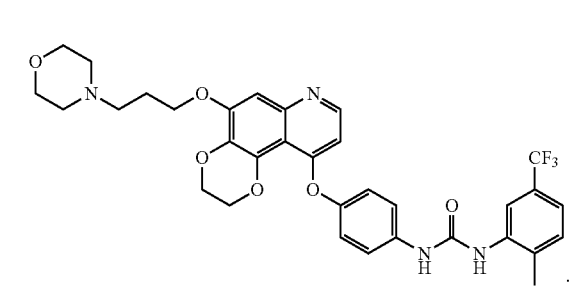
.

17. The compound according to claim 16 having the following structure:

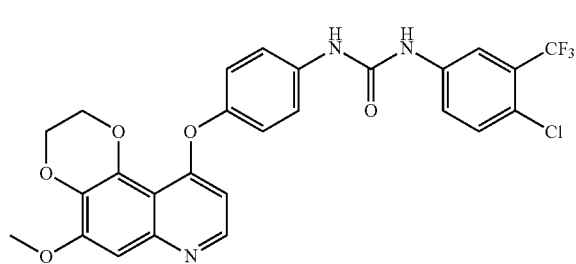 [SMILES: COc1cc2nccc(Oc3ccc(NC(=O)Nc4ccc(Cl)c(C(F)(F)F)c4)cc3)c2c2c1OCCO2]

or a pharmaceutically acceptable salt thereof.

18. The compound according to claim 16 having the following structure:

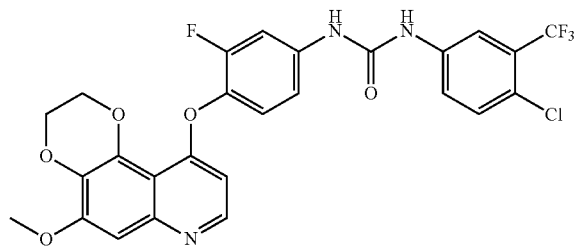 [SMILES: COc1cc2nccc(Oc3ccc(NC(=O)Nc4ccc(Cl)c(C(F)(F)F)c4)cc3F)c2c2c1OCCO2]

or a pharmaceutically acceptable salt thereof.

19. The compound according to claim 16 having the following structure:

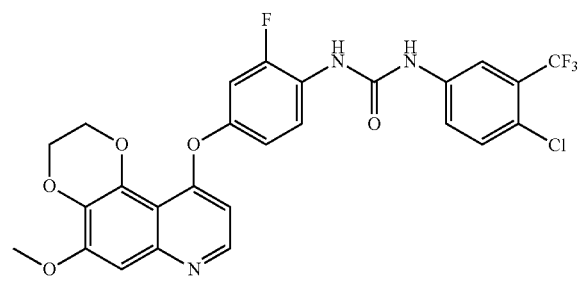 [SMILES: COc1cc2nccc(Oc3ccc(NC(=O)Nc4ccc(Cl)c(C(F)(F)F)c4)c(F)c3)c2c2c1OCCO2]

or a pharmaceutically acceptable salt thereof.

20. The compound according to claim 16 having the following structure:

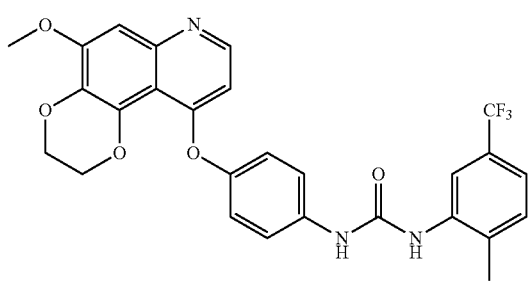 [SMILES: COc1cc2nccc(Oc3ccc(NC(=O)Nc4cc(C(F)(F)F)ccc4C)cc3)c2c2c1OCCO2]

or a pharmaceutically acceptable salt thereof.

* * * * *